(12) United States Patent
Choi

(10) Patent No.: US 9,682,059 B2
(45) Date of Patent: *Jun. 20, 2017

(54) PHENYL CARBAMATE COMPOUNDS FOR USE IN PREVENTING OR TREATING EPILEPSY OR EPILEPSY-RELATED SYNDROME

(71) Applicant: Bio-Pharm Solutions Co., Ltd., Gyeonggi-do (KR)

(72) Inventor: Yong Moon Choi, Pine Brook, NJ (US)

(73) Assignee: Bio-Pharm Solutions Co., Ltd., Gyeonggi-do (KR)

( * ) Notice: Subject to any disclaimer, the term of this patent is extended or adjusted under 35 U.S.C. 154(b) by 0 days.

This patent is subject to a terminal disclaimer.

(21) Appl. No.: 14/775,189

(22) PCT Filed: Mar. 11, 2014

(86) PCT No.: PCT/KR2014/002007
§ 371 (c)(1),
(2) Date: Sep. 11, 2015

(87) PCT Pub. No.: WO2014/142520
PCT Pub. Date: Sep. 18, 2014

(65) Prior Publication Data
US 2016/0030382 A1    Feb. 4, 2016

Related U.S. Application Data

(60) Provisional application No. 61/776,926, filed on Mar. 12, 2013.

(51) Int. Cl.
| *A61K 31/325* | (2006.01) |
| *C07C 271/12* | (2006.01) |
| *C07C 271/24* | (2006.01) |
| *A61K 31/03*  | (2006.01) |
| *A61K 31/27*  | (2006.01) |

(52) U.S. Cl.
CPC ............ *A61K 31/325* (2013.01); *A61K 31/03* (2013.01); *A61K 31/27* (2013.01); *C07C 271/12* (2013.01); *C07C 271/24* (2013.01); *C07C 2101/02* (2013.01); *C07C 2101/14* (2013.01); *C07C 2102/42* (2013.01)

(58) Field of Classification Search
CPC ...... A61K 31/325; A61K 31/27; A61K 31/03; C07C 271/24; C07C 271/12; C07C 2101/02; C07C 2101/14; C07C 2102/42
See application file for complete search history.

(56) References Cited

U.S. PATENT DOCUMENTS

| 3,265,728 | A | * | 8/1966 | Bossinger | ............... A61K 31/27 560/163 |
| 3,313,692 | A |   | 4/1967 | Bossinger | |
| 3,313,696 | A |   | 4/1967 | Bossinger et al. | |
| 3,313,700 | A |   | 4/1967 | Bossinger et al. | |
| 3,509,162 | A |   | 4/1970 | Besendorf | |
| 5,258,397 | A |   | 11/1993 | Lepage et al. | |
| 6,541,513 | B2 |   | 4/2003 | Plata-Salaman et al. | |
| 6,589,985 | B2 |   | 7/2003 | Plata-Salaman et al. | |
| 7,078,436 | B2 |   | 7/2006 | Plata-Salaman et al. | |
| 8,859,817 | B2 |   | 10/2014 | Choi | |
| 9,018,253 | B2 |   | 4/2015 | Choi | |
| 9,029,589 | B2 |   | 5/2015 | Choi | |
| 9,034,848 | B2 |   | 5/2015 | Choi | |
| 9,162,975 | B2 |   | 10/2015 | Choi | |
| 2001/0034365 | A1 | * | 10/2001 | Choi | ....................... A61K 31/27 514/483 |
| 2002/0165273 | A1 |   | 11/2002 | Plata-Salaman et al. | |
| 2004/0171679 | A1 |   | 9/2004 | Plata-Salaman et al. | |
| 2008/0090903 | A1 |   | 4/2008 | Pandey et al. | |
| 2009/0048213 | A1 |   | 2/2009 | Kimura et al. | |
| 2012/0184762 | A1 |   | 7/2012 | Choi | |
| 2013/0005801 | A1 |   | 1/2013 | Choi | |
| 2013/0184338 | A1 |   | 7/2013 | Choi | |
| 2013/0203846 | A1 |   | 8/2013 | Choi | |
| 2014/0275243 | A1 |   | 9/2014 | Choi | |
| 2015/0133541 | A1 |   | 5/2015 | Choi | |
| 2016/0015678 | A1 |   | 1/2016 | Choi | |
| 2016/0015679 | A1 |   | 1/2016 | Choi | |
| 2016/0015680 | A1 |   | 1/2016 | Choi | |

(Continued)

FOREIGN PATENT DOCUMENTS

| CN | 1208402 A | 2/1999 |
| JP | 61271992 | 12/1986 |

(Continued)

OTHER PUBLICATIONS

International Search Report dated Jun. 26, 2014 for International Application No. PCT/KR2014/002007 filed Mar. 11, 2014.
Office Actions mailed Nov. 25, 2015 and Apr. 27, 2016 for U.S. Appl. No. 14/774,884, filed Sep. 11, 2015.
International Search Report dated Jun. 27, 2014 for PCT International Application No. PCT/KR2014/002061 filed Mar. 12, 2014.
International Search Report dated Jun. 24, 2014 for PCT International Application No. PCT/KR2014/002062 filed Mar. 12, 2014.
Office Action mailed Feb. 2, 2016 for U.S. Appl. No. 14/774,891, filed Sep. 11, 2015.
Office Actions mailed Nov. 25, 2016 and Apr. 15, 2016 for U.S. Appl. No. 14/775,092, filed Sep. 11, 2015.
International Search Report for corresponding PCT application No. PCT/KR2014/002060, dated Jun. 27, 2014.

(Continued)

*Primary Examiner* — Sudhakar Katakam
(74) *Attorney, Agent, or Firm* — McDonnell Boehnen Hulbert & Berghoff LLP

(57) ABSTRACT

The present invention provides a pharmaceutical composition for preventing and/or treating a epilepsy or epilepsy-related syndrome, for example an intractable epilepsy or its related syndrome such as drug-resistant epilepsy, comprising the phenyl carbamate compound as an active ingredient, and a use of the phenyl carbamate compound for preventing and/or treating epilepsy or epilepsy-related syndrome.

10 Claims, 1 Drawing Sheet

(56) References Cited

U.S. PATENT DOCUMENTS

| | | |
|---|---|---|
| 2016/0016896 A1 | 1/2016 | Choi |
| 2016/0030382 A1 | 2/2016 | Choi |

FOREIGN PATENT DOCUMENTS

| | | |
|---|---|---|
| JP | 2002-515029 A1 | 5/2002 |
| JP | 2008-513466 A1 | 5/2008 |
| KR | 1020030078947 | 10/2003 |
| KR | 10-0467760 B1 | 4/2005 |
| KR | 100886578 | 3/2009 |
| KR | 1020090067210 | 6/2009 |
| KR | 1020090082213 | 7/2009 |
| KR | 100910928 | 8/2009 |
| KR | 1020090110889 | 10/2009 |
| KR | 10-0197901 B1 | 12/2016 |
| WO | 97/26241 A1 | 7/1997 |
| WO | 02/67925 A1 | 6/2002 |
| WO | 02051395 A1 | 7/2002 |
| WO | 02/067923 A1 | 9/2002 |
| WO | 2006033947 A2 | 3/2006 |
| WO | 2007/008551 A2 | 1/2007 |
| WO | 2008048801 | 4/2008 |
| WO | 2008048802 | 4/2008 |
| WO | 2008124848 | 10/2008 |
| WO | 2010137351 | 12/2010 |
| WO | 2012-002773 | 1/2012 |
| WO | 2012/096458 A2 | 7/2012 |
| WO | 2013/100570 A1 | 7/2013 |
| WO | 2013/100571 A1 | 7/2013 |

OTHER PUBLICATIONS

International Search Report for corresponding PCT application No. PCT/KR2014/002059, dated Jun. 27, 2014.
International Search Report for corresponding PCT application No. PCT/KR2014/002005, dated Jun. 24, 2014.
Jiao et al, A Sequential O-Nitrosoaldol and Grinard Addition Process: An Enantio and Diastereoselelctive entry to Chiral 1,.2-Diols, Angew. Chem. Int. Ed., 2009, 48 p. 3333-3336.
Girijavallabhan et al, Synthesis of the anti-fungal agent SCH 42427, SM 1964, Bioorganic & Medicinal Chemistry Letters, 1991, 1(7), p. 349-352, (Abstract, p. 1).
Supplementary European Search Report for corresponding PCT application No. PCT/KR2014/002007 dated Dec. 12, 2016.
Tasker, "Emergency treatment of acute seizures and status epilepticus", Arch Dis Child, 79:78-83 (1998).
Deshpande et al., "Carisbamate prevents the development and expression of spontaneous recurrent epileptiform discharges and is neuroprotective in cultured hippocampal neurons", Epilepsia, 49(10):1795-1802 (2008).

\* cited by examiner

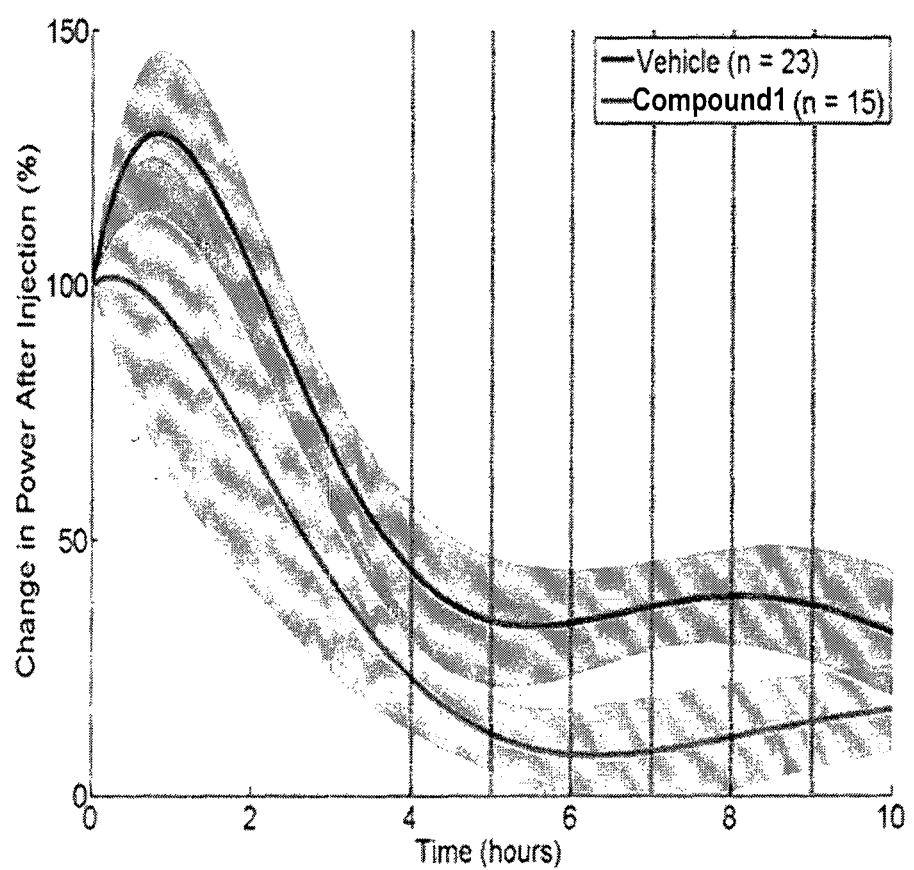

PHENYL CARBAMATE COMPOUNDS FOR USE IN PREVENTING OR TREATING EPILEPSY OR EPILEPSY-RELATED SYNDROME

CROSS-REFERENCE TO RELATED APPLICATIONS

This application is a US national phase application of International Patent Application No. PCT/KR2014/002007 filed on 11 Mar. 2014, which claims the benefit of the filing date of US Provisional Application Ser. No. 61/776,926 filed 12 Mar. 2013.

TECHNICAL FIELD

The present invention provides a pharmaceutical composition for preventing and/or treating a epilepsy or epilepsy-related syndrome, for example an intractable epilepsy or its related syndrome such as drug-resistant epilepsy, comprising the phenyl carbamate compound as an active ingredient, and a use of the phenyl carbamate compound for preventing and/or treating epilepsy or epilepsy-related syndrome.

RELATED ART

Epilepsy and its related syndromes may be classified according to whether the associated seizures are partial or generalized, and whether the etiology is idiopathic or symptomatic/cryptogenic. Several important syndromes can be further grouped according to age of onset and prognosis.

Epilepsy is a chronic brain disease in which epileptic seizures are the predominant feature. Generally, most epilepsies and diseases associated therewith are difficult to treat, since epilepsies are not etiologically elucidated. Thus, administration of an antiepileptic agent is a common approach toward suppressing epileptic seizures or inhibiting propagation of focal seizures to other portions.

The older established antiepileptic drugs (AEDs) such as phenytoin carbamazepine, clonazepam, ethosuximide, valproic acid and barbiturates are widely prescribed but suffer from a range of side effect. Furthermore, there is a significant group of patients (20-30%) that are resistant to the currently available therapeutic agents. Fifty million people in the world have epilepsy, and there are between 16 and 51 cases of new-onset epilepsy per 100,000 people every year. A community-based study in southern France estimated that up to 22.5% of patients with epilepsy have drug-resistant epilepsy. Patients with drug-resistant epilepsy have increased risks of premature death, injuries, psychosocial dysfunction, and a reduced quality of life.

One study showed that the use-dependent blockade of the fast sodium current in dentate granule cells by carbamazepine was lost in hippocampi resected from patients with carbamazepine-resistant temporal-lobe epilepsy, although this finding did not extend to lamotrigine, which has a pharmacologic action similar to that of carbamazepine. Altered expression of subtypes of the γ-aminobutyric acid type A (GABA$_A$) receptor has also been observed in patients with drug-resistant temporal-lobe epilepsy. Whether these changes result in reduced sensitivity to antiepileptic drugs that act on the receptor is unknown.

Since 1989 several new drugs have been launched, including felbamate, gabapentin, lamotrigine, oxcarbazepine, tiagabine, topimarate, vigabartrin, zonisamide and levetiracetam. While many of new drugs AEDs show improved efficacies and side-effect profiles, patients with intractable epilepsy remain untreated. Because of the need to individualize therapy, no rigid set of guidelines can be applied to determine medical intractability. There is still a need for improved medication.

SUMMARY OF THE INVENTION

An embodiment provides a pharmaceutical composition for the prevention and the treatment of an epilepsy or a epilepsy-related syndrome, for example an intractable epilepsy or its related syndrome such as drug-resistant epilepsy, comprising a phenyl carbamate compound of the following Chemical Formula 1, an enantiomer or a diastereomer thereof, or a mixture of enantiomers or diastereomers; or a pharmaceutically acceptable salt thereof.

Another embodiment is to provide a method of preventing and/or treating an epilepsy or a epilepsy-related syndrome in a subject comprising administering a pharmaceutically effective amount of a phenyl carbamate compound represented by Chemical Formula 1; a racemate, an enantiomer, a diastereomer, a mixture of enantiomers, or a mixture of diastereomers thereof; or a pharmaceutically acceptable salt thereof, to the subject in need.

Still other embodiment is to provide a phenyl carbamate compound represented by Chemical Formula 1; a racemate, an enantiomer, a diastereomer, a mixture of enantiomers, or a mixture of diastereomers thereof; or a pharmaceutically acceptable salt thereof, for use in the prevention and/or treatment of epilepsy or the manufacture of a pharmaceutical composition for preventing and/or treating an epilepsy or a epilepsy-related syndrome.

DETAILED DESCRIPTION OF THE EMBODIMENTS

Continuing its research work in the field of epilepsy, the present inventors, as results of studies on the development of the drugs useful for prevention and/or treatment of an epilepsy or a epilepsy-related syndrome, found that a substituted phenyl carbamate compounds of the following Chemical Formula 1 exhibits remarkably excellent anti-epilepsy activity in various emulation models and simultaneously has very low toxicity, and completed the invention.

Therefore, an embodiment provides a pharmaceutical composition for prevention and/or treatment of an epilepsy or a epilepsy-related syndrome, comprising an organic compound, i.e., phenyl carbamate derivatives, more particularly, a phenyl carbamate compound represented by following Chemical Formula 1; a racemate, an enantiomer, a diastereomer, a mixture of enantiomers, or a mixture of diastereomers thereof; or a pharmaceutically acceptable salt thereof:

[Chemical Formula 1]

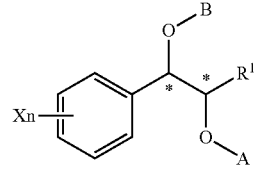

wherein,

X is a halogen, for example, chlorine, fluorine, iodine, or bromine, n, that means the number of substituent X, is an integer from 1 to 5, for example, 1 or 2, R1 is a linear or branched alkyl group of C1-C4, for example, methyl group, ethyl group, isopropyl group, or butyl group, A is hydrogen or a carbamoyl derivative represented by

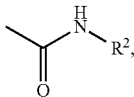

B is hydrogen, a carbamoyl derivative represented by

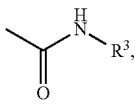

trialkyl silyl groups (e.g., a trimethyl silyl (TMS) group, a triethyl silyl (TES) group, a triisopropyl silyl (TIPS) group, t-butyl dimethyl silyl (TBDMS) group, and the like), trialkylaryl silyl groups (wherein the total number of alkyl and aryl groups is three; e.g., a t-butyl diphenyl silyl (TBDPS) group and the like), or a trialkyl silyl ether group, wherein each alkyl group may be independently selected from the group consisting of linear, branched, or cyclic C1-C4 alkyl groups, and each aryl group may be independently selected from the group consisting of C5-C8 aryl groups, preferably a phenyl group, A and B are not carbamoyl derivatives at same time, and R2 and R3 may be the same as or different from each other, and independently selected from the group consisting of hydrogen, a linear or branched alkyl group of C1-C4, for example C1-C3, a cycloalkyl group of C3-C8, for example C3-C7, and benzyl group, and more specifically, R2 and R3 may be the same as or different from each other, and independently selected from the group consisting of hydrogen, methyl group, propyl group, isopropyl group, cyclopropyl group, cyclohexyl group, bicycloheptane group, and benzyl group.

Preferably, in Chemical Formula 1, A is hydrogen and B is carbamoyl group, or A is a carbamoyl group and B is hydrogen.

In the embodiment, in Chemical Formula 1, if X is F or Br, A and B are not hydrogen at the same time, if X is chlorine and n is 1 and A and B are hydrogen at the same time, R1 is a C2-C4 linear or branched alkyl group, if X is chlorine and n is 1, R1 is methyl, isopropyl or butyl, and if X is bromine located at 4-postion of the aromatic ring and n is 1, R1 is methyl, propyl, isopropyl or butyl, and if A is the carbamoyl represented by, B is hydrogen, R1 is ethyl, and n is 2 at the same time, two X are located at 2 and 3 positions, 2 and 4 positions, 2 and 5 positions, or 3 and 5 positions of the aromatic ring.

In a concrete embodiment, the phenyl carbamate compound may be selected from the group consisting of:
1-(2-chlorophenyl)-1-hydroxypropyl-2-carbamate,
1-(2-chlorophenyl)-1-hydroxybutyl-2-carbamate,
1-(2-chlorophenyl)-1-hydroxy-3-methyl-butyl-2-carbamate,
1-(2-chlorophenyl)-1-hydroxyhexyl-2-carbamate,
1-(2-chlorophenyl)-1-hydroxypropyl-2-N-methylcarbamate,
1-(2-chlorophenyl)-1-hydroxypropyl-2-N-propylcarbamate,
1-(2-chlorophenyl)-1-hydroxypropyl-2-N-isopropylcarbamate,
1-(2-chlorophenyl)-1-hydroxypropyl-2-N-cyclopropylcarbamate,
1-(2-chlorophenyl)-1-hydroxypropyl-2-N-cyclohexylcarbamate,
1-(2-chlorophenyl)-1-hydroxypropyl-2-N-benzylcarbamate,
1-(2-chlorophenyl)-1-hydroxypropyl-2-N-bicyclo[2,2,1]heptanecarbamate,
1-(2,4-dichlorophenyl)-1-hydroxypropyl-2-carbamate,
1-(2,6-dichlorophenyl)-1-hydroxypropyl-2-carbamate,
1-(2,4-dichlorophenyl)-1-hydroxybutyl-2-carbamate,
1-(2,6-dichlorophenyl)-1-hydroxybutyl-2-carbamate
1-(2,4-dichlorophenyl)-1-hydroxy-3-methyl-butyl-2-carbamate,
1-(2,6-dichlorophenyl)-1-hydroxy-3-methyl-butyl-2-carbamate,
1-(2,4-dichlorophenyl)-1-hydroxyhexyl-2-carbamate,
1-(2,6-dichlorophenyl)-1-hydroxyhexyl-2-carbamate,
1-(2-chlorophenyl)-2-hydroxypropyl-1-carbamate,
1-(2-chlorophenyl)-2-hydroxypropyl-1-N-methylcarbamate,
1-(2-chlorophenyl)-2-hydroxypropyl-1-N-propylcarbamate,
1-(2-chlorophenyl)-2-hydroxypropyl-1-N-isopropylcarbamate,
1-(2-chlorophenyl)-2-hydroxypropyl-1-N-cyclopropylcarbamate,
1-(2-chlorophenyl)-2-hydroxypropyl-1-N-cyclohexylcarbamate,
1-(2-chlorophenyl)-2-hydroxypropyl-1-N-benzylcarbamate,
1-(2,4-dichlorophenyl)-2-hydroxypropyl-1-carbamate,
1-(2,6-dichlorophenyl)-2-hydroxypropyl-1-carbamate,
1-(2,4-dichlorophenyl)-2-hydroxybutyl-1-carbamate,
1-(2,6-dichlorophenyl)-2-hydroxybutyl-1-carbamate,
1-(2,4-dichlorophenyl)-2-hydroxy-3-methyl-butyl-1-carbamate,
1-(2,6-dichlorophenyl)-2-hydroxy-3-methyl-butyl-1-carbamate,
1-(2,4-dichlorophenyl)-2-hydroxyhexyl-1-carbamate,
1-(2,6-dichlorophenyl)-2-hydroxyhexyl-1-carbamate,
1-(2-fluorophenyl)-1-hydroxypropyl-2-carbamate,
1-(2-iodophenyl)-1-hydroxypropyl-2-carbamate,
1-(2-iodophenyl)-1-hydroxybutyl-2-carbamate,
1-(2,3-dichlorophenyl)-1-hydroxypropyl-2-carbamate, and
1-(2,3-dichlorophenyl)-2-hydroxypropyl-1-carbamate.

In another concrete embodiment, the compound may not include 1-(2-chlorophenyl)-1,2-propanediol, 1-(2-chlorophenyl)-1-hydroxybutyl-2-carbamate, and 1-(2,6-dichlorophenyl)-1-hydroxybutyl-2-carbamate.

In this compound, 2 chiral carbons exist at positions 1 and 2 from phenyl group substituted with X; thus, the compound may exist in the form of an enantiomer, a diastereomer, a mixture of enantiomers, or a mixture of diastereomers, as well as a racemate.

In an embodiment, the phenyl carbamate compound is selected from the group consisting of:
1-(2-chlorophenyl)-(S)-1-hydroxypropyl-(S)-2-carbamate, 1-(2-chlorophenyl)-(R)-1-hydroxypropyl-(R)-2-carbamate,
racemate of 1-(2-chlorophenyl)-(S)-1-hydroxypropyl-(S)-2-carbamate and 1-(2-chlorophenyl)-(R)-1-hydroxypropyl-(R)-2-carbamate,
1-(2-chlorophenyl)-(R)-1-hydroxypropyl-(S)-2-carbamate, 1-(2-chlorophenyl)-(S)-1-hydroxypropyl-(R)-2-carbamate,
1-(2-chlorophenyl)-(S)-1-hydroxybutyl-(S)-2-carbamate,
racemate of 1-(2-chlorophenyl)-(S)-1-hydroxybutyl-(S)-2-carbamate and 1-(2-chlorophenyl)-(R)-1-hydroxybutyl-(R)-2-carbamate,
1-(2-chlorophenyl)-(S)-1-hydroxy-3-methyl-butyl-(S)-2-carbamate,
racemate of 1-(2-chlorophenyl)-(S)-1-hydroxy-3-methyl-butyl-(S)-2-carbamate and 1-(2-chlorophenyl)-(R)-1-hydroxy-3-methyl-butyl-(R)-2-carbamate,
1-(2-chlorophenyl)-(S)-1-hydroxypropyl-(S)-2-N-methylcarbamate,
1-(2-chlorophenyl)-(S)-1-hydroxypropyl-(S)-2-N-propylcarbamate,
1-(2-chlorophenyl)-(S)-1-hydroxypropyl-(R)-2-N-isopropylcarbamate,
1-(2-chlorophenyl)-(S)-1-hydroxypropyl-(R)-2-N-cyclopropylcarbamate,
1-(2-chlorophenyl)-(S)-1-hydroxypropyl-(R)-2-N-cyclohexyl carbamate,
1-(2-chlorophenyl)-(R)-1-hydroxypropyl-(R)-2-N-methylcarbamate,
1-(2-chlorophenyl)-(R)-1-hydroxypropyl-(R)-2-N-propylcarbamate,
1-(2-chlorophenyl)-(R)-1-hydroxypropyl-(R)-2-N-isopropylcarbamate,
1-(2-chlorophenyl)-(R)-1-hydroxypropyl-(R)-2-N-cyclopropylcarbamate,
1-(2-chlorophenyl)-(R)-1-hydroxypropyl-(R)-2-N-cyclohexyl carbamate,
racemate of 1-(2-chlorophenyl)-(S)-1-hydroxypropyl-(S)-2-N-methylcarbamate and 1-(2-chlorophenyl)-(R)-1-hydroxypropyl-(R)-2-N-methylcarbamate
racemate of 1-(2-chlorophenyl)-(S)-1-hydroxypropyl-(S)-2-N-propylcarbamate and 1-(2-chlorophenyl)-(R)-1-hydroxypropyl-(R)-2-N-propylcarbamate,
racemate of 1-(2-chlorophenyl)-(S)-1-hydroxypropyl-(S)-2-N-isopropylcarbamate and 1-(2-chlorophenyl)-(R)-1-hydroxypropyl-(R)-2-N-isopropylcarbamate,
racemate of 1-(2-chlorophenyl)-(S)-1-hydroxypropyl-(S)-2-N-cyclopropylcarbamate and 1-(2-chlorophenyl)-(R)-1-hydroxypropyl-(R)-2-N-cyclopropylcarbamate,
racemate of 1-(2-chlorophenyl)-(S)-1-hydroxypropyl-(S)-2-N-cyclohexylcarbamate and 1-(2-chlorophenyl)-(R)-1-hydroxypropyl-(R)-2-N-cyclohexylcarbamate,
1-(2-fluorophenyl)-(S)-1-hydroxypropyl-(S)-2-carbamate,
1-(2-fluorophenyl)-(R)-1-hydroxypropyl-(R)-2-carbamate,
1-(2-iodophenyl)-(S)-1-hydroxypropyl-(S)-2-carbamate,
1-(2-iodophenyl)-(R)-1-hydroxypropyl-(R)-2-carbamate, and
1-(2-iodophenyl)-(S)-1-hydroxybutyl-(S)-2-carbamate.

Alternatively, the compound may be in the form of a pharmaceutically acceptable salt. The pharmaceutically acceptable salt may include an additional salt of acid or base, and its stereochemical isomer. For example, the compound may be in the form of an additional salt of an organic or inorganic acid. The salt may not be specially limited, and include any salts that maintain the activities of their parent compounds, with no undesirable effects, in the subject, when they are administered to the subject. Such salts may include inorganic and organic salts, such as salts of acetic acid, nitric acid, aspartic acid, sulfonic acid, sulfuric acid, maleic acid, glutamic acid, formic acid, succinic acid, phosphoric acid, phthalic acid, tannic acid, tartaric acid, hydrobromic acid, propionic acid, benzene sulfonic acid, benzoic acid, stearic acid, lactic acid, bicarbonic acid, bisulfuric acid, bitartaric acid, oxalic acid, butyric acid, calcium edetate, carbonic acid, chlorobezoic acid, citric acid, edetic acid, toluenesulfonic acid, fumaric acid, gluceptic acid, esilic acid, pamoic acid, gluconic acid, methyl nitric acid, malonic acid, hydrochloric acid, hydroiodic, hydroxynaphtholic acid, isethionic acid, lactobionic acid, mandelic acid, mucic acid, naphthylic acid, muconic acid, p-nitromethanesulfonic acid, hexamic acid, pantothenic acid, monohydrogen phosphoric acid, dihydrogen phosphoric acid, salicylic acid, sulfamic acid, sulfanilic acid, methane sulfonic acid, and the like.

The additional salts of base may include salts of akali metal or alkaline earth metal, such as salts of ammonium, lithium, sodium, potassium, magnesium, calcium, and the like; salts having an organic base, such as benzathine, N-methyl-D-glucamine, hydrabamine, and the like; and salts having an amino acid such as arginine, lysine, and the like. In addition, these salts may be converted to a released form by treating with a proper base or acid.

Reaction Formula I: Synthesis of Diol-1

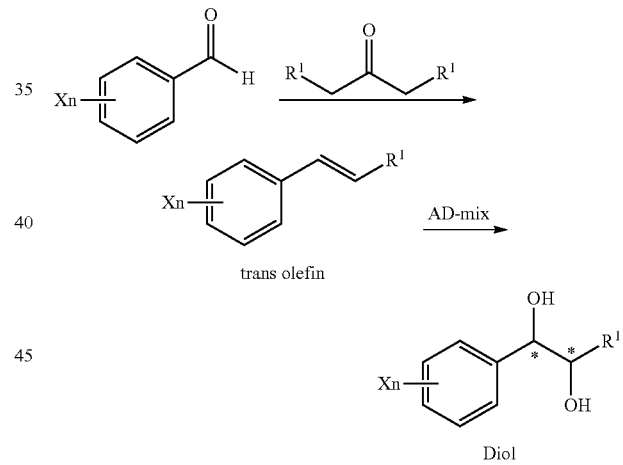

A diol compound used in the synthesis of the carbamate compound may be synthesized by dihydroxylation of a trans-olefin compound. A diol compound having optical activity may be synthesized using a sharpless asymmetric dihydroxylation catalyst.

Reaction Formula II: Synthesis of Diol-2

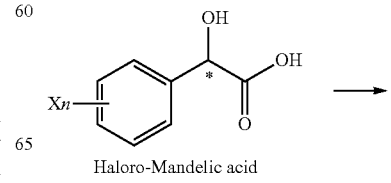

Haloro-Mandelic acid

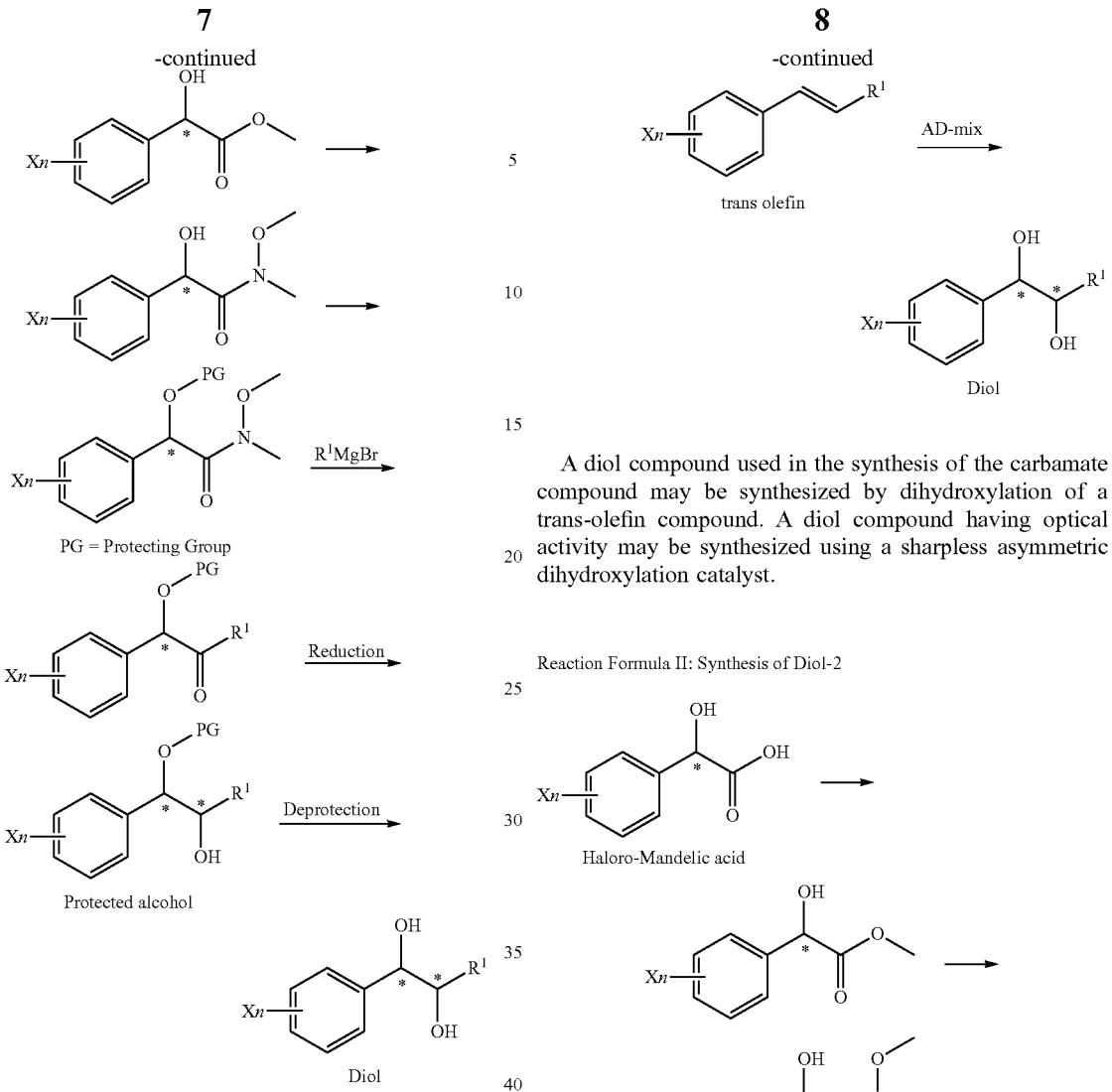

As indicated in the Reaction Formula II, the optically active substance of diol may also be synthesized using an reduction reagent after synthesizing a hydroxy-ketone compound using Haloro-Mandelic acid. In the Reaction Formula II, PG may be Trialkyl Silyl group (TMS, TES, TIPS, TBDMS, TBDPS), Ether group [MOM (Mothoxymethyl ether), MEM (2-Methoxyethoxymethyl ether), BOM (Benzyloxymethyl ether). MTM (Methylthiomethyl ether), SEM (2-(Trimethylsilyl)ethoxymethyl ether), PMBM (p-Methoxybenzyl ether), THP (Tetrahydropyranyl ether), Allyl ether, Trityl ether, Ester group [Ac (acetate), Bz (Benzoate), Pv (Pivaloate), Cbz (Benzyl carbonate), BOC (t-Butyl carbonate), Fmoc (9-Fulorenylmethyl)carbaonate, Alloc (Allyl Carbonate), Troc (Trichloroethyl carbonate), or p-Methoxybenzoate, Methyl carbonate, and so on.

Reaction Formula I: Synthesis of Diol-1

A diol compound used in the synthesis of the carbamate compound may be synthesized by dihydroxylation of a trans-olefin compound. A diol compound having optical activity may be synthesized using a sharpless asymmetric dihydroxylation catalyst.

Reaction Formula II: Synthesis of Diol-2

-continued

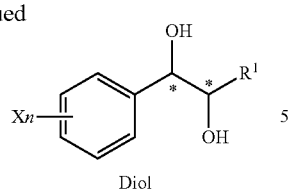
Diol

As indicated in the Reaction Formula II, the optically active substance of diol may also be synthesized using a reduction reagent after synthesizing a hydroxy-ketone compound using Haloro-Mandelic acid. In the Reaction Formula II, PG (protecting group) may be selected from the group consisting of trialkyl silyl group (e.g., a trimethyl silyl (TMS) group, a triethyl silyl (TES) group, a triisopropyl silyl (TIPS) group, t-butyl dimethyl silyl (TBDMS) group, and the like), trialkylaryl silyl groups (wherein the total number of alkyl and aryl groups is three; e.g., a t-butyl diphenyl silyl (TBDPS) group and the like), ester group [Ac (acetate), Bz (benzoate), Pv (pivaloate), Cbz (benzyl carbonate), BOC (t-butyl carbonate), Fmoc (9-fluoroenylmethyl)carbaonate, Alloc (allyl Carbonate), Troc (trichloroethyl carbonate), p-methoxybenzoate, methyl carbonate, and so on] and the like, wherein each alkyl group may be independently selected from the group consisting of linear, branched, or cyclic C1-C4 alkyl groups, and each aryl group may be independently selected from the group consisting of C5-C8 aryl groups, preferably a phenyl group.

Reaction Formula III: Carbamation reaction-1

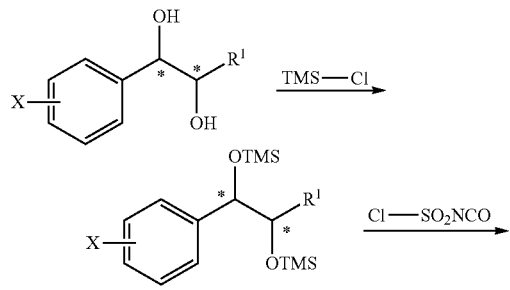

-continued

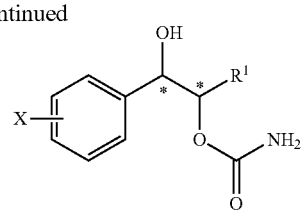

As a highly selectivity form of regioisomer of single carbamate of diol having halogen substituent at phenyl ring. (Example 1 to 14 and 36 to 67 are synthesized by reaction formula III)

Reaction Formula IV: Carbamation reaction-2

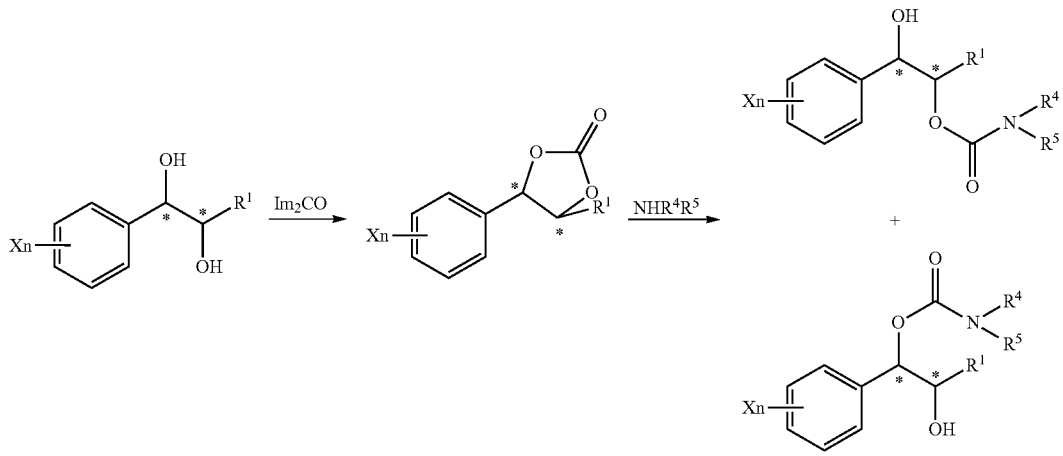

Two substances in the form of regioisomers of a single carbamate of diol having halogen substituent at phenyl ring may be separated by flash column chromatography to obtain two kinds of single carbamate compounds. (Example 15~35 and 68~115 are synthesized by reaction formula IV)

Reaction Formula V: Proection reaction

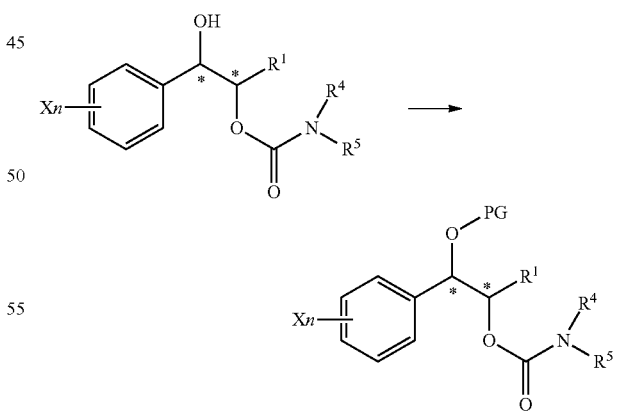

In the Reaction Formula V, PG (protecting group) may be selected from the group consisting of trialkyl silyl group (e.g., a trimethyl silyl (TMS) group, a triethyl silyl (TES) group, a triisopropyl silyl (TIPS) group, t-butyl dimethyl silyl (TBDMS) group, and the like), trialkylaryl silyl groups (wherein the total number of alkyl and aryl groups is three; e.g., a t-butyl diphenyl silyl (TBDPS) group and the like), ester group [Ac (acetate), Bz (benzoate), Pv (pivaloate), Cbz (benzyl carbonate), BOC (t-butyl carbonate), Fmoc (9-fluorenylmethyl)carbaonate, Alloc (allyl Carbonate), Troc (trichloroethyl carbonate), p-methoxybenzoate, methyl carbonate, and so on] and the like, wherein each alkyl group may be independently selected from the group consisting of linear, branched, or cyclic C1-C4 alkyl groups, and each aryl group may be independently selected from the group consisting of C5-C8 aryl groups, preferably a phenyl group.

In the Reaction Formula IV and V, R4 and R5 may be the same as or different from each other, and independently selected from the group consisting of hydrogen, a linear or branched alkyl group of C1-C4, for example C1-C3, a cycloalkyl group of C3-C8, for example C3-C7, and benzyl group, and more specifically, R4 and R5 may be the same as or different from each other, and independently selected from the group consisting of hydrogen, methyl group, propyl group, isopropyl group, cyclopropyl group, cyclohexyl group, bicycloheptane group, and benzyl group.

Two substances in the form of regioisomers of a single carbamate of diol having halogen substituent at phenyl ring may be separated by flash column chromatography to obtain two kinds of single carbamate compounds.

Another embodiment provides a method of prevention and/or treatment of a an epilepsy or a epilepsy-related syndrome, comprising administering a pharmaceutically effective amount of a phenyl carbamate compound represented by Chemical Formula 1; a racemate, an enantiomer, a diastereomer, a mixture of enantiomers, or a mixture of diastereomers thereof; or a pharmaceutically acceptable salt thereof, to a subject in need of preventing and/or treating drug-resistant epilepsy or drug-resistant epilepsy-related symptom. The method can be applied for preventing and/or treating drug-resistant epilepsy or drug-resistant epilepsy-related symptom.

The method may further comprise a step of identifying the subject in need of preventing and/or treating an epilepsy or a epilepsy-related syndrome, prior to the step of administering. Another embodiment provides a phenyl carbamate compound represented by Chemical Formula 1; a racemate, an enantiomer, a diastereomer, a mixture of enantiomers, or a mixture of diastereomers thereof; or a pharmaceutically acceptable salt thereof, for use in the prevention and/or treatment of an epilepsy or a epilepsy-related syndrome.

Another embodiment provides a use of a phenyl carbamate compound represented by Chemical Formula 1; a racemate, an enantiomer, a diastereomer, a mixture of enantiomers, or a mixture of diastereomers thereof; or a pharmaceutically acceptable salt thereof for the manufacture of a pharmaceutical composition for preventing and/or treating an epilepsy or a epilepsy-related syndrome.

In an embodiment, the present invention relates to a therapeutic or preventive agent for epilepsy and epilepsy-related syndrome, preferable an intractable epilepsy and its related syndrome.

The characteristics of intractable epilepsy include 1) high occurrence of partial seizure followed by a generalized seizure (particularly temporal lobe epilepsy); 2) high occurrence of symptomatic epilepsy caused by an organic lesion in the brain; 3) long-term absence of treatment from the onset to consultation of a specialist and high occurrence of seizures; and 4) high occurrence of status epilepticus in the anamnesis. In other words, the temporal lobe is likely to be a portion of the brain responsible for intractable epilepsy. It is indicated that epilepsy becomes more intractable by changing the nature thereof and evolving as acquired seizures are repeated.

Intractable epilepsy is categorized into three clinical types, i.e., (a) localization-related epilepsies and syndromes, (b) generalized epilepsies and syndromes, and (c) epilepsies and syndromes undetermined, whether focal or generalized.

Examples of (a) localization-related epilepsies and syndromes include temporal lobe epilepsies, frontal lobe epilepsies, and multi-lobe epilepsies. Temporal lobe epilepsies and frontal lobe epilepsies are typical examples of intractable epilepsy. Multi-lobe epilepsies are considered to be caused by two or more lobes.

Examples of (b) generalized epilepsies and syndromes include myoclonic epilepsy.

Examples of (c) epilepsies and syndromes undetermined, whether focal or generalized, include severe myoclonic epilepsy, which exhibits a variety of seizure types. In particular, tonic-clonic seizures frequently occur, to thereby often lead to status epilepticus. Thus, special treatment conducted by a specialist for epilepsy is strongly required (Masako WATANABE, et al., Igakuno Ayumi, 183(1):103-108, 1997).

Seizures associated with intractable epilepsy are categorized into a variety of types, e.g., tonic seizures, tonic-clonic seizures, atypical absence seizures, atonic seizures, myoclonic seizures, clonic seizures, simple partial seizures, complex partial seizures, and secondary generalized seizures. Of these, for tonic and atonic seizures, attention must be paid to injuries resulting from falls.

In addition, complex partial seizures may cause a behavior-caused accident during disturbance of consciousness. In intractable epilepsies, "complex partial seizures" associated with temporal lobe epilepsies and frontal lobe epilepsies occur at relatively high frequency in adults. Although said seizures occur at low frequency in children, the seizures are also intractable as in the case of adults (Progress of Epileptology, No. 2, Haruo AKIMOTO and Toshio YAMAUCHI, Iwanami Gakujutsu Shuppan, 1991, p 51-85).

In the present description, the term "intractable epilepsy" refers to epilepsies or seizures associated therewith corresponding to the following four epilepsies or seizures associated therewith:

(1) epilepsies difficult to treat in which suppression of seizures associated therewith cannot be controlled through a conventional pharmaceutical treatment (Masako WATANABE, et al., Igaku-no Ayumi, 183(1):103-108, 1997);

(2) epilepsies corresponding to the following (a) to (c): (a) localization-related epilepsies such as temporal lobe epilepsis and cortical epilepsis; (b) generalized epilepsies and myoclonic epilepsy; and (c) epilepsies and syndromes undetermined, whether focal or generalized, such as severe myoclonic epilepsy;

(3) seizures associated with the above-described intractable epilepsis including tonic seizures, tonic-clonic seizures, atypical absence seizures, atonic seizures, myoclonic seizures, clonic seizures, simple partial seizures, complex partial seizures, and secondary generalized seizures; and (4) epilepsies such as epilepsies following brain surgery, traumatic epilepsies, and relapsed epilepsies following surgery for epilepsy.

The antiepileptic agent of the present invention is effective for the above four types of intractable epilepsies. Of these, the antiepileptic agent of the present invention is particularly effective for localization-related epilepsies corresponding to (2) (a); seizures such as secondary generalized seizures, complex partial seizures and status epilepticus corresponding to (3) and status epilepticus; and epilepsies following brain surgery, traumatic epilepsies, and relapsed epilepsies following surgery for epilepsy corresponding to (4). The antiepileptic agent of the present invention has a possibly excellent effect to epilepsies such as localization-related epilepsies, temporal lobe epilepsies, and cortical epilepsies.

"Temporal lobe epilepsy," which is one type of intractable epilepsy, is an epilepsy having a seizure focus in the temporal lobe, and is categorized under symptomatic and localization-related epilepsies, which also include frontal lobe epilepsies, parietal lobe epilepsies, and occipital lobe epilepsies, based on the international classification of epilepsy.

The syndromes of temporal lobe epilepsy vary in accordance with a focus-localized site and type of seizure propagation, in that the temporal lobe has an anatomically complex structure including neocortex, allocortex, and paleocortex. Temporal lobe epilepsy, as previously defined as a psychomotor seizure, mostly causes complex partial seizures as clinically observed seizures, and also causes simple partial seizures, secondary generalized seizures, and combinations thereof.

Simple partial seizures include autonomic and mental symptoms and sensory symptoms such as olfaction, audition, or vision, sometimes concomitant with symptoms of experiences such as deja-vu and jamais-vu. Complex partial seizures often exhibit motion stopping followed by eating-function automatism, and are divided into amygdala-hippocampus seizures and lateral temporal lobe seizures according to localization. In the case of temporal lobe epilepsy, 70-80% of the seizures are hippocampus seizures, in which aura, motion stopping, lip automatism, and clouding of consciousness are successively developed to result in amnesia. When the focus is in the amygdala, there are caused autonomic symptoms such as dysphoria in the epigastrium; phobia; and olfactory hallucination. Lateral temporal lobe seizures include auditory illusion, hallucination, and a dreamy state, and disturbance of speech when the focus is in the dominant hemisphere. Temporal lobe epilepsy exhibits a long-term psychosis-like state in addition to other symptoms and recognition-and-memory disorder more frequently than do other epilepsies (Medical Dictionary, Nanzando). Treatment of temporal lobe epilepsy is carried out through pharmacotherapy employing a maximum dose of a combination of drugs, or through surgical treatment.

"Cortex epilepsy," which is one type of intractable epilepsy, is an epilepsy having a focus in the cerebral cortex, and is classified as symptomatic epilepsy belonging to localization-related (focal) epilepsies and syndromes in the international classification of epilepsy. In the international classification, seizures associated with cortex epilepsy are classified as simple partial seizures, which are partial seizures without reduction of consciousness. Accordingly, an electroencephalogram taken during a seizure associated with cortex epilepsy (not always recorded on the scalp) exhibits localized contralateral electric discharge from the corresponding cortical field. The cortex epilepsy is classified as temporal lobe epilepsy, parietal lobe epilepsy, or occipital lobe epilepsy.

"Traumatic epilepsy," which is one type of intractable epilepsy, in a broad sense, is divided into two epilepsies, i.e., "early epilepsy" and "late epilepsy." "Early epilepsy" is caused through stimulation of the brain induced by convulsion within a week after suffering a trauma, and is not a true epilepsy. In contrast, "late epilepsy" is a true epilepsy that is caused one or more weeks after suffering a trauma. Most of the traumatic epilepsies are caused by formation of a focus at a traumatically damaged portion of the cortex, and they are considered to be typical examples of partial epilepsies.

"A secondary generalized seizure," which is one of the symptoms associated with intractable epilepsy, is one type of partial seizure, which exhibit a clinical syndrome and an electrocephalogram feature observed as excitation of neurons that shows initiation of a seizure in a limited portion of one cerebral hemisphere. The secondary generalized seizure is initiated as a simple partial seizure (without impairment of consciousness) or a complex partial seizure (with impairment of consciousness), and develops to general convulsion induced through secondary generalization. The main symptom thereof is convulsion such as a tonic-clonic seizure, a tonic seizure, or a clonic seizure.

"A complex partial seizure," which is one of the symptoms associated with intractable epilepsy, refers to a partial seizure with impairment of consciousness, and is similar to a seizure that has conventionally been called a psycho-motor seizure or a seizure associated with temporal lobe epilepsy. In the international classification draft (1981), the complex partial seizure is defined as a seizure with impairment of consciousness exhibiting an electrocephalogram during a seizure in which unilateral or bilateral electric discharge attributed to a focus in a diffuse or a temporal or front-temporal portion.

Clinically, an epileptic seizure results from a sudden and abnormal electrical discharge originating from a collection of interconnected neurons in the brain or elsewhere in the nervous system. Depending on the type of epilepsy involved, the resulting nerve cell activity may be manifested by a wide variety of clinical symptoms such as uncontrollable motor movements, changes in the patient's level of consciousness and the like. Epilepsy and epileptic seizures and syndromes may be classified in a variety of ways (See, The Treatment of Epilepsy, Principles & Practice, Third Edition, Elaine Wyllie, M. D. Editor, Lippincott Williams & Wilkins, 2001). However, as used herein the terms; "epilepsy", "epileptic seizures" and "epileptic syndromes" are meant to include all known types of epileptic seizures and syndromes including; partial seizures, including simple, complex and partial seizures evolving to generalized tonic-clonic convulsions and generalized seizures, both convulsive and nonconvulsive and unclassified epileptic seizures.

Patients with epilepsy whose seizures do not successfully respond to antiepileptic drug (AED) therapy are considered to have drug-resistant epilepsy (DRE). This condition is also referred to as intractable, medically refractory, or pharmacoresistant epilepsy. The International League Against Epilepsy (ILAE) defines drug resistant epilepsy as a failure of adequate trials of two tolerated and appropriately chosen and used AED schedules (whether as monotherapies or in combination) to achieve sustained seizure freedom.

As used herein, the term "anti-epileptic drug(s)" or "AED(s)" generally encompasses pharmacological agents that reduce the frequency or likelihood of a seizure. There are many drug classes that comprise the set of antiepileptic drugs (AEDs), and many different mechanisms of action are represented. For example, some medications are believed to increase the seizure threshold, thereby making the brain less likely to initiate a seizure. Other medications retard the spread of neural bursting activity and tend to prevent the propagation or spread of seizure activity. Some AEDs, such as the Benzodiazepines, act via the GABA receptor and globally suppress neural activity. However, other AEDs may act by modulating a neuronal calcium channel, a neuronal potassium channel, a neuronal NMDA channel, a neuronal AMPA channel, a neuronal metabotropic type channel, a neuronal sodium channel, and/or a neuronal kainite channel. The phrase "Anti-epileptic drugs that block sodium channels", "sodium-channel-blocking AEDs" used herein refers to anti-epileptic drugs that block sodium channels. The sodium-channel-blocking AEDs can be selected from the group consisting of topiramate, carbamazepine, oxcarbazepine, phenytoin, lamotrigine, zonisamide, felbamate, ethosuximide, and valproate (valproic acid), as well as other existing or new AEDs which may be identified to block sodium channels in the future.

As used herein, the terms "subject" or "patient" are used herein interchangeably and as used herein, refer to a human being, who has been the object of treatment, observation or experiment.

The pharmaceutical composition may be formulated in various forms for oral or parenteral administration. For example, the pharmaceutical composition may be formulated in the oral administration form, such as a tablet, pill, soft or hard capsule, liquid, suspension, emulsion, syrup, granules, elixirs, and the like. In addition to the active ingredient, the oral administration form may further include pharmaceutically acceptable and conventional components, for example, a diluent such as lactose, dextrose, sucrose, mannitol, sorbitol, cellulose, glycine, and the like; a lubricant such as silica, talc, stearic acid, magnesium or calcium salt thereof, polyethyleneglycol, and the like. In the case that the oral administration form is a tablet, it may further include a binder such as magnesium aluminium silicate, starch paste, gelatin, tragacanth, methylcellulose, sodium carboxymethylcellulose, polyvinylpirrolidine, and the like; and optionally include one or more additives selected from the group consisting of a disintegrant such as starch, agar, arginic acid or sodium salt thereof, an absorbent, a colorant, a flavoring, a sweetener, and the like. Alternatively, the pharmaceutical composition may also be formulated in a parenteral administration form, which can be administered by subcutaneous injection, intravenous injection, intramuscular injection, injection into thoracic cavity, and the like. In order to formulate the parenteral administration form, the pharmaceutical composition may be prepared as a solution or suspension wherein the active ingredient is dissolved in water together with a stabilizer and/or a buffering agent, and such solution or suspension formulation may be prepared as a dosage form in ample or vial.

The pharmaceutical composition may be sterilized, and/or include further additives such as a preservative, a stabilizer, a hydrating agent, an emulsification accelerator, a salt and/or buffering agent for osmoregulation, and the like, and/or further therapeutically effective ingredients. The pharmaceutical composition may be formulated by any conventional method for mixing, granulating, coating, and the like.

The pharmaceutical composition may be administered to a mammal including human, in the pharmaceutically effective amount of 0.01 to 750 mg/kg (body weight), preferably 0.1 to 500 mg/kg (body weight) per one day, based on the active ingredient. The pharmaceutically effective amount may refers to an amount capable of exhibiting a desired effect, i.e., an effect of treating and/or preventing epilepsy. The pharmaceutically effective amount may be administered through oral or parenteral pathway (e.g., an intravenous injection, an intramusclular injection, etc.), one or two or more times per one day.

The pharmaceutically effective amount and the administration pathway of the present pharmaceutical composition may be properly adjusted by a person skilled in the relevant field considering the conditions of the subject (patient), desired effects, and the like. The subject may be a mammal including human or cells and/or tissues obtained therefrom.

BRIEF DESCRIPTION OF DRAWINGS

FIG. 1 is a graph showing the measurement results of benzodiazepine-resistant electrographic status epilepsy model of 1-(2-chlorophenyl)-(S)-1-hydroxypropyl-(S)-2-carbamate (compound 1) in the test (Rats).

EXAMPLE

The present invention is further explained in more detail with reference to the following examples. These examples, however, should not be interpreted as limiting the scope of the present invention in any manner.

Preparation Example 1

Synthesis of 1-(2-chlorophenyl)-trans-1-propene

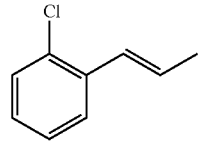

48 ml of 2-chlorobenzenaldehyde (0.42 mol) and 49.7 ml of 3-pentanone (0.47 mol) were dissolved in 600 mL of hexane in flask, and then stirred with raising the temperature. 53.6 ml of Boron trifluoride etherate ($BF_3OEt_2$, 0.42 mol) was added to the resultant under reflux conditions. When the reaction was completed, water was added thereto. After layer separation, the obtained organic layer was washed twice with 1M sodium hydroxide solution (1M NaOH), and then the separated organic layer was washed with water. The separated organic layer was dehydrated with anhydrous magnesium sulfate ($MgSO_4$) and concentrated. The concentrated residue was purified by a silica gel column chromatography to produce the title compound (38 g, yield 58%). $^1$H NMR (400 MHz, $CDCl_3$) δ 1.94(d, J=4.8 Hz, 3H), 6.24(m, 1H), 6.78(d, J=14 Hz, 1H), 7.11~7.51(m, 4H)

Preparation Example 2

Synthesis of 1-(2-chlorophenyl)-trans-1-butene

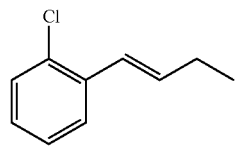

The substantially same method as described in Preparation Example 1 was conducted, except that 3-heptanone was used instead of 3-pentanone, to obtain the title compound (2.9 g, yield 83%).
$^1$H NMR (400 MHz, $CDCl_3$) δ 1.14(d, J=7.6 Hz, 3H), 2.29~2.33(m, 2H), 6.28(dt, J=16 Hz, 6.4 Hz, 1H), 6.78(d, J=15.6 Hz, 1H), 7.13~7.54(m, 4H)

Preparation Example 3

Synthesis of 1-(2-chlorophenyl)-3-methyl-trans-1-butene

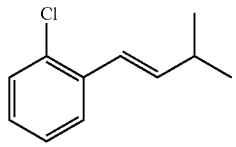

The substantially same method as described in Preparation Example 1 was conducted, except that 2,6-dimethylheptan-4-one was used instead of 3-pentanone, to obtain the title compound (8.0 g, yield 50~90%).

$^1$H NMR (400 MHz, CDCl$_3$) δ 1.14(d, J=6.8 Hz, 6H), 2.25~2.57(m, 1H), 6.20(dd, J=16 Hz, 7.2 Hz, 1H), 7.64(d, J=16 Hz, 1H), 7.12~7.54(m, 4H)

Preparation Example 4

Synthesis of 1-(2-chlorophenyl)-trans-1-hexene

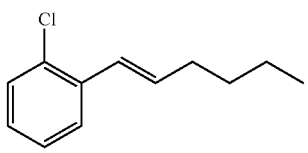

The substantially same method as described in Preparation Example 1 was conducted, except that 6-undecanone was used instead of 3-pentanone, to obtain the title compound (10 g, yield 85%).

$^1$H NMR (400 MHz, CDCl$_3$) δ 0.96(t, J=7.2 Hz, 3H), 1.33~1.56(m, 4H), 2.26~2.32(m, 4H), 6.24(dt, J=15.6 Hz, 7 Hz, 1H), 6.78(d, J=16 Hz, 1H), 7.13~7.54(m, 4H)

Preparation Example 5

Synthesis of 1-(2,4-dichlorophenyl)-trans-1-propene

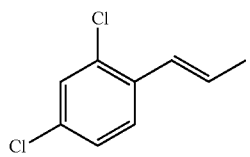

The substantially same method as described in Preparation Example 1 was conducted, except that 2,4-dichlorobenzenaldehyde was used instead of 2-chlorobenzenaldehyde, to obtain the title compound (2.4 g, yield 57%).

$^1$H NMR (400 MHz, CDCl$_3$) δ 1.95(dd, J=6.8 Hz, 1.6 Hz, 3H), 6.24(m, 1H), 6.72(d, J=15.6 Hz, 1H), 7.18~7.44(m, 3H)

Preparation Example 6

Synthesis of 1-(2,4-dichlorophenyl)-trans-1-butene

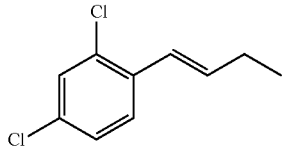

The substantially same method as described in Preparation Example 5 was conducted, except that 3-heptanone was used instead of 3-pentanone, to obtain the title compound (2.1 g, yield 90%).

$^1$H NMR (400 MHz, CDCl$_3$) δ 1.14(d, J=7.6 Hz, 3H), 2.20~2.33(m, 2H), 6.26(dt, J=16 Hz, 6.8 Hz, 1H), 6.70(d, J=15.6 Hz, 1H), 7.18~7.46(m, 3H)

Preparation Example 7

Synthesis of 1-(2,6-dichlorophenyl)-3-methyl-trans-1-butene

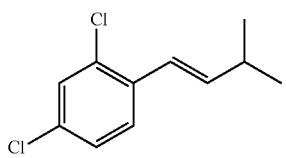

The substantially same method as described in Preparation Example 5 was conducted, except that 2,6-dimethylheptan-4-one was used instead of 3-pentanone, to obtain the title compound (0.23 g, yield 10~40%).

$^1$H NMR (400 MHz, CDCl$_3$) δ 1.15(d, J=6.8 Hz, 6H), 2.53~2.58(m, 1H), 6.19(dd, J=16.4 Hz, 6.8 Hz, 1H), 6.31(d, J=16.4 Hz, 1H), 7.18~7.46(m, 3H)

Preparation Example 8

Synthesis of 1-(2,4-dichlorophenyl)-trans-1-hexene

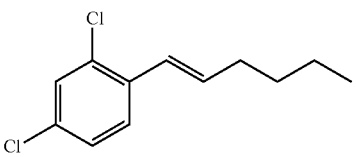

The substantially same method as described in Preparation Example 5 was conducted, except that 6-undecanone was used instead of 3-pentanone, to obtain the title compound (3.2 g, yield 40~80%).

$^1$H NMR (400 MHz, CDCl$_3$) δ 0.96(t, J=7.2 Hz, 3H), 1.38~1.52(m, 4H), 2.25~2.31(m, 2H), 6.22(dt, J=15.6 Hz, 6.8 Hz, 1H), 6.70(d, J=15.6 Hz, 1H), 7.18~7.46(m, 3H)

Preparation Example 9

Synthesis of 1-(2,6-dichlorophenyl)-trans-1-propene

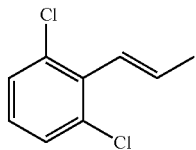

The substantially same method as described in Preparation Example 1 was conducted, except that 2,6-dichlorobenzenaldehyde was used instead of 2-chlorobenzenaldehyde, to obtain the title compound (0.4 g, yield 10~40%).

$^1$H NMR (400 MHz, CDCl$_3$) δ 1.98(d, J=8 Hz, 3H), 6.23~6.31(m, 1H), 6.40(d, J=16 Hz, 1H), 7.05~7.32(m, 3H)

Preparation Example 10

Synthesis of 1-(2,6-dichlorophenyl)-trans-1-butene

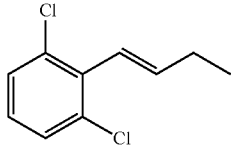

The substantially same method as described in Preparation Example 9 was conducted, except that 3-heptanone was used instead of 3-pentanone, to obtain the title compound (1.2 g, yield 10~40%).

$^1$H NMR (400 MHz, CDCl$_3$) δ 1.17(t, J=7.6 Hz, 3H), 2.30~2.37(m, 2H), 6.29(dt, J=16.4 Hz, 6 Hz, 1H), 6.37(d, J=16.4 Hz, 1H), 7.05~7.32(m, 3H)

Preparation Example 11

Synthesis of 1-(2,6-dichlorophenyl)-3-methyl-trans-1-butene

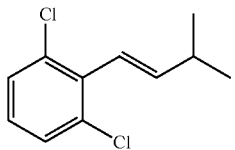

The substantially same method as described in Preparation Example 9 was conducted, except that 2,6-dimethylheptan-4-one was used instead of 3-pentanone, to obtain the title compound (0.23 g, yield 10~40%).

$^1$H NMR (400 MHz, CDCl$_3$) δ 1.15(d, J=6.8 Hz, 6H), 2.53~2.58(m, 1H), 6.19(dd, J=16.4 Hz, 6.8 Hz, 1H), 6.31(d, J=16.4 Hz, 1H), 7.05~7.32(m, 3H)

Preparation Example 12

Synthesis of 1-(2,6-dichlorophenyl)-trans-1-hexene

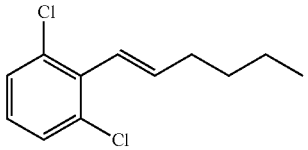

The substantially same method as described in Preparation Example 9 was conducted, except that 6-undecanone was used instead of 3-pentanone, to obtain the title compound (0.2 g, yield 10~40%).

$^1$H NMR (400 MHz, CDCl$_3$) δ 0.99(t, J=7.2 Hz, 3H), 1.14~1.59(m, 4H), 2.30~2.36(m, 2H), 6.24(dt, J=16 Hz, 6.6 Hz, 1H), 6.38(d, J=16.4 Hz, 1H), 7.05~7.33(m, 3H)

Preparation Example 13

Synthesis of 1-(2,3-dichlorophenyl)-trans-1-propene

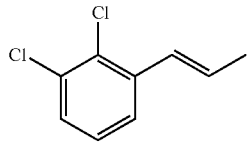

The substantially same method as described in Preparation Example 1 was conducted, except that 2,3-dichlorobenzenaldehyde was used instead of 2-chlorobenzenaldehyde, to obtain the title compound (0.2 g, yield 10~40%).

$^1$H NMR (400 MHz, CDCl$_3$) δ 1.94(d, J=4.8 Hz, 3H), 6.24(m, 1H), 6.78(d, J=14 Hz, 1H), 7.11~7.51(m, 3H)

Preparation Example 14

Synthesis of 1-(2-chlorophenyl)-(S,S)-1,2-propanediol

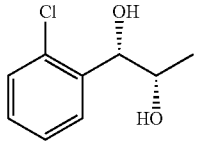

1-(2-chlorophenyl)-trans-1-propene (1.5 g, Preparation Example 1) was dissolved in 30 mL of the mixture of t-BuOH/H$_2$O (1:1(V/V)). At 0° C., AD-mix-α (Aldrich, U.S.A.) (13.7 g) and methane sulfone amide (CH$_3$SO$_2$NH$_2$, 0.76 g, 0.0080 mol) were added thereto and stirred for overnight. When the reaction was completed, the obtained product was washed with an aqueous solution of sodium sulfite (Na$_2$SO$_3$) and ethylacetate (EA). Then, the organic layer was dehydrated with anhydrous magnesium sulfate (MgSO$_4$), filtrated, and concented under reduced pressure. The concentrated residue was purified by a silica gel column chromatography to produce the title compound (1.65 g, yield 90%).

¹H NMR (400 MHz, CDCl₃) δ 1.20(d, J=6.4 Hz, 3H), 2.48(d, J=4.0 Hz, 1H), 2.92(d, J=4.4 Hz, 1H), 3.93~3.97(m, 1H), 4.97(t, J=4.8 Hz, 1H), 7.22~7.51(m, 4H)
¹³CNMR (100 MHz, CDCl₃) δ 18.8, 71.5, 74.4, 127.1, 128.1, 128.9, 129.5, 132.6, 138.9

Preparation Example 15

Synthesis of 1-(2-chlorophenyl)-(R,R)-1,2-propanediol

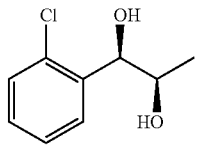

1-(2-chlorophenyl)-trans-1-propene (2.5 g, Preparation Example 1) was dissolved in 50 mL of the mixture of t-BuOH/H₂O (1:1(V/V)). At 0° C., AD-mix-α (Aldrich, U.S.A.) (23.5 g) and methane sulfone amide (CH₃SO₂NH₂, 1.27 g, 0.013 mol) were added thereto and stirred for overnight. When the reaction was completed, the obtained product was washed with an aqueous solution of sodium sulfite (Na₂SO₃) and ethylacetate (EA). Then, the organic layer was dehydrated with anhydrous magnesium sulfate (MgSO₄), filtrated, and concented under reduced pressure. The concentrated residue was purified by a silica gel column chromatography to produce the title compound (2.96 g, yield 90%).
¹H NMR (400 MHz, CDCl₃) δ1.20(d, J=6.4 Hz, 3H), 2.48(d, J=4.0 Hz, 1H), 2.92(d, J=4.4 Hz, 1H), 3.93~3.97(m, 1H), 4.97(t, J=4.8 Hz, 1H), 7.22~7.51(m, 4H)

Preparation Example 16

Synthesis of the mixture of 1-(2-chlorophenyl)-(S,S)-1,2-pronanediol and 1-(2-chlorophenyl)-(R,R)-1,2-propanediol

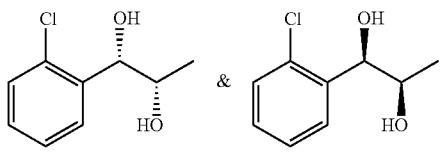

1-(2-chlorophenyl)-trans-1-propene (6.53 g, Preparation Example 1) was dissolved in 45 mL of the mixture of acetone/t-BuOH/H₂O (5:1:1 V/V). At the room temperature, N-methylmorpholine-N-oxide (7.51 g) and OsO₄(0.54 g) were added thereto and stirred for 2-3 hours. When the reaction was completed, the obtained product was washed with water and methylenechloride (MC). Then, the organic layer was dehydrated with anhydrous magnesium sulfate (MgSO₄), filtrated, and concented under reduced pressure. The concentrated residue was purified by a silica gel column chromatography to produce the title compound (6.42 g, yield 80%).
¹H NMR (400 MHz, CDCl₃)δ1.20(d, J=6.4 Hz, 3H), 2.48(d, J=4.0 Hz, 1H), 2.92(d, J=4.4 Hz, 1H), 3.93~3.97(m, 1H), 4.97(t, J=4.8 Hz, 1H), 7.22~7.51(m, 4H)

Preparation Example 17

Synthesis of 1-(2-chlorophenyl)-(S,S)-1,2-butanediol

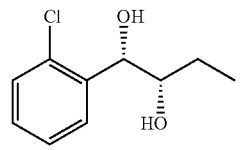

The substantially same method as described in Preparation Example 14 was conducted, except that 1-(2-chlorophenyl)-trans-1-butene (Preparation Example 2) was used instead of 1-(2-chlorophenyl)-trans-1-propene (Preparation Example 1), to obtain the title compound (0.36 g, yield 95%).
¹H NMR(400 MHz, CDCl₃)δ1.01(t, J=7.4 Hz, 3H), 1.52~1.65(m, 2H), 2.01(d, J=4.4 Hz, 1H), 2.74(d, J=5.2 Hz, 1H), 3.69~3.75(m, 1H), 5.05(t, J=5.0 Hz, 1H), 7.23~7.54(m, 4H)

Preparation Example 18

Synthesis of 1-(2-chlorophenyl)-(R,R)-1,2-butanediol

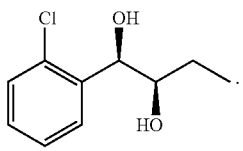

The substantially same method as described in Preparation Example 15 was conducted, except that 1-(2-chlorophenyl)-trans-1-butene (Preparation Example 2) was used instead of 1-(2-chlorophenyl)-trans-1-propene (Preparation Example 1), to obtain the title compound (0.84 g, yield 60~95%).
¹H NMR(400 MHz, CDCl₃)δ1.01(t, J=7.4 Hz, 3H), 1.52~1.65(m, 2H), 2.01(d, J=4.4 Hz, 1H), 2.74(d, J=5.2 Hz, 1H), 3.69~3.75(m, 1H), 5.05(t, J=5.0 Hz, 1H), 7.23~7.54(m, 4H)

Preparation Example 19

Synthesis of the mixture of 1-(2-chlorophenyl)-(S,S)-1,2-butanediol and 1-(2-chlorophenyl)-(R,R)-1,2-butanediol

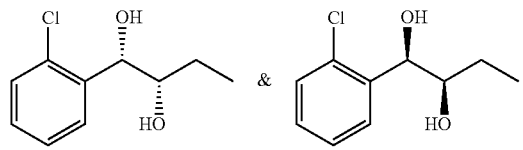

The substantially same method as described in Preparation Example 16 was conducted, except that 1-(2-chlorophenyl)-trans-1-butene (Preparation Example 2) was used instead of 1-(2-chlorophenyl)-trans-1-propene (Preparation Example 1), to obtain the title compound (5.1 g, yield 60~90%).
¹H NMR(400 MHz, CDCl₃) δ1.01(t, J=7.4 Hz, 3H), 1.52~1.65(m, 2H), 2.01(d, J=4.4 Hz, 1H), 2.74(d, J=5.2 Hz, 1H), 3.69~3.75(m, 1H), 5.05(t, J=5.0 Hz, 1H), 7.23~7.54(m, 4H)

Preparation Example 20

Synthesis, of 1-(2-chlorophenyl)-3-methyl-(S,S)-1,2-butanediol

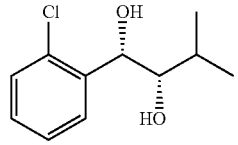

The substantially same method as described in Preparation Example 14 was conducted, except that 1-(2-chlorophenyl)-3-methyl-trans-1-butene (Preparation Example 3) was used instead of 1-(2-chlorophenyl)-trans-1-propene (Preparation Example 1), to obtain the title compound (0.96 g, yield 60~90%).
¹H NMR(400 MHz, CDCl₃)δ1.07(t, J=7.2 Hz, 6H), 1.83~1.89(m, 1H), 1.92(d, J=5.6 Hz, 1H), 2.69(d, J=6.4 Hz, 1H), 3.53~3.56(m, 1H), 5.22~5.25(m, 1H), 7.23~7.55(m, 4H)

Preparation Example 21

Synthesis of 1-(2-chlorophenyl)-3-methyl-(R,R)-1,2-butanediol

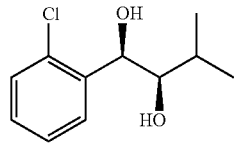

The substantially same method as described in Preparation Example 15 was conducted, except that 1-(2-chlorophenyl)-3-methyl-trans-1-butene (Preparation Example 3) was used instead of 1-(2-chlorophenyl)-trans-1-propene (Preparation Example 1), to obtain the title compound (4.2 g, yield 60~90%).
¹H NMR(400 MHz, CDCl₃)δ1.07(t, J=7.2 Hz, 6H), 1.82~1.90(m, 1H), 1.93(d, J=5.6 Hz, 1H), 2.79(d, J=6 Hz, 1H), 3.53~3.57(m, 1H), 5.23~5.25(m, 1H), 7.23~7.54(m, 4H)

Preparation Example 22

Synthesis of the mixture of 1-(2-chlorophenyl)-3-methyl-(S,S)-1,2-butanediol and 1-(2-chlorophenyl)-3-methyl-(R,R)-1,2-butanediol

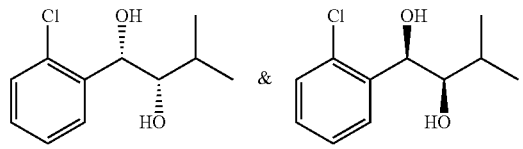

The substantially same method as described in Preparation Example 16 was conducted, except that 1-(2-chlorophenyl)-3-methyl-trans-1-butene (Preparation Example 3)

was used instead of 1-(2-chlorophenyl)-trans-1-propene (Preparation Example 1), to obtain the title compound (0.8 g, yield 60~90%).
¹H NMR(400 MHz, CDCl₃) δ 1.07(t, J=7.2 Hz, 6H), 1.83~1.90(m, 1H), 1.92(d, J=5.6 Hz, 1H), 2.69(d, J=6.4 Hz, 1H), 3.53~3.56(m, 1H), 5.22~5.25(m, 1H), 7.23~7.55(m, 4H)

Preparation Example 23

Synthesis of 1-(2-chlorophenyl)-(S,S)-1,2-hexanediol

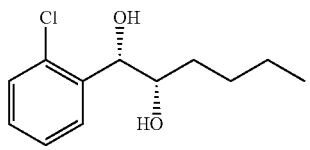

The substantially same method as described in Preparation Example 14 was conducted, except that 1-(2-chlorophenyl)-trans-1-hexene (Preparation Example 4) was used instead of 1-(2-chlorophenyl)-trans-1-propene (Preparation Example 1), to obtain the title compound (0.37 g, yield 90%).
¹H NMR(400 MHz, CDCl₃)δ0.90(t, J=7.2 Hz, 3H), 1.35~1.65(m, 6H), 2.08(d, J=4.4 Hz, 1H), 2.71(d, J=5.2 Hz, 1H), 3.78~3.83(m, 1H), 5.04(t, J=5.0 Hz, 1H), 7.23~7.53(m, 4H)

Preparation Example 24

Synthesis of 1-(2-chlorophenyl)-(R,R)-1,2-hexanediol

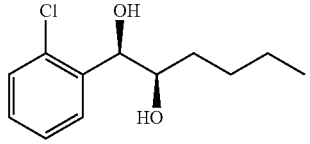

The substantially same method as described in Preparation Example 15 was conducted, except that 1-(2-chlorophenyl)-trans-1-hexene (Preparation Example 4) was used instead of 1-(2-chlorophenyl)-trans-1-propene (Preparation Example 1), to obtain the title compound (4.2 g, yield 60~90%).
¹H NMR(400 MHz, CDCl₃)δ0.91(t, J=6.6 Hz, 3H), 1.35~1.65(m, 6H), 2.08(d, J=4.8 Hz, 1H), 2.70(d, J=5.2 Hz, 1H), 3.80~3.83(m, 1H), 5.05(t, J=5.0 Hz, 1H), 7.24~7.56(m, 4H)

Preparation Example 25

Synthesis of the mixture of 1-(2-chlorophenyl)-(S,S)-1,2-hexanediol and 1-(2-chlorophenyl)-(R,R)-1,2-hexanediol

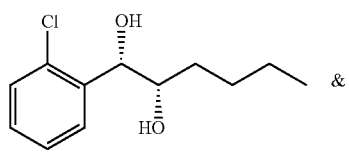

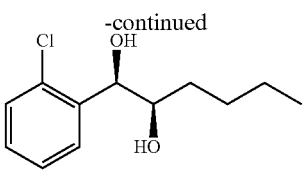

The substantially same method as described in Preparation Example 16 was conducted, except that 1-(2-chlorophenyl)-trans-1-hexene (Preparation Example 4) was used instead of 1-(2-chlorophenyl)-trans-1-propene (Preparation Example 1), to obtain the title compound (7.9 g, yield 60~90%).

$^1$H NMR(400 MHz, CDCl$_3$)δ0.90(t, J=7.2 Hz, 3H), 1.26~1.55(m, 6H), 2.08(d, J=4.4 Hz, 1H), 2.71(d, J=5.6 Hz, 1H), 3.78~3.84(m, 1H), 5.04(t, J=3.2 Hz, 1H), 7.24~7.55(m, 4H)

Preparation Example 26

Synthesis of
1-(2,4-dichlorophenyl)-(S,S)-1,2-propanediol

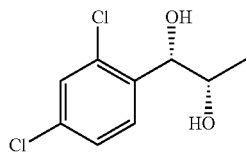

The substantially same method as described in Preparation Example 14 was conducted, except that 1-(2,4-ichlorophenyl)-trans-1-propene (Preparation Example 5) was used instead of 1-(2-chlorophenyl)-trans-1-propene (Preparation Example 1), to obtain the title compound (0.33 g, yield 60~95%).

$^1$H NMR(400 MHz, CDCl$_3$)δ1.22(d, J=6.4 Hz, 3H), 2.10 (d, J=4.4 Hz, 1H), 2.71(d, J=4.8 Hz, 1H), 3.90~3.95(m, 1H), 4.94(t, J=5.0 Hz, 1H), 7.31(dd, J=2.0 Hz, J=8.0 Hz, 1H), 7.40(d, J=2.0 Hz, 1H), 7.49(d, J=8.4 Hz, 1H)

Preparation Example 27

Synthesis of
1-(2,4-dichlorophenyl)-(R,R)-1,2-propanediol

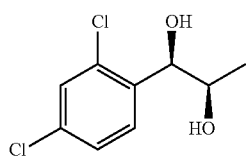

The substantially same method as described in Preparation Example 15 was conducted, except that 1-(2,4-ichlorophenyl)-trans-1-propene (Preparation Example 5) was used instead of 1-(2-chlorophenyl)-trans-1-propene (Preparation Example 1), to obtain the title compound (0.45 g, yield 60~95%).

$^1$H NMR(400 MHz, CDCl$_3$)δ1.22(d, J=6.4 Hz, 3H), 2.10 (d, J=4.4 Hz, 1H), 2.71(d, J=4.8 Hz, 1H), 3.90~3.95(m, 1H), 4.94(t, J=5.0 Hz, 1H), 7.31~7.49(m, 3H)

Preparation Example 28

Synthesis of the mixture of 1-(2,4-dichlorophenyl)-(S,S)-1,2-propanediol and 1-(2,4-dichlorophenyl)-(R,R)-1,2-propanediol

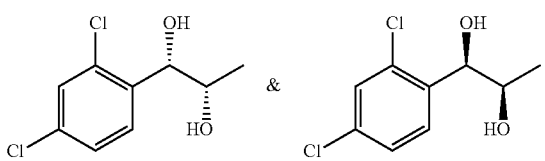

The substantially same method as described in Preparation Example 16 was conducted, except that 1-(2,4-ichlorophenyl)-trans-1-propene (Preparation Example 5) was used instead of 1-(2-chlorophenyl)-trans-1-propene (Preparation Example 1), to obtain the title compound (0.45 g, yield 60~95%).

$^1$H NMR(400 MHz, CDCl$_3$)δ1.22(d, J=6.4 Hz, 3H), 2.10 (d, J=4.4 Hz, 1H), 2.71(d, J=4.8 Hz, 1H), 3.90~3.95(m, 1H), 4.94(t, J=5.0 Hz, 1H), 7.31~7.49(m, 3H)

Preparation Example 29

Synthesis of
1-(2,4-dichlorophenyl)-(S,S)-1,2-butanediol

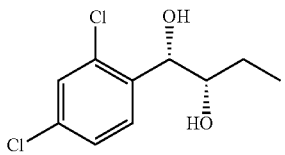

The substantially same method as described in Preparation Example 14 was conducted, except that 1-(2,4-dichlorophenyl)-trans-1-butene (Preparation Example 6) was used instead of 1-(2-chlorophenyl)-trans-1-propene (Preparation Example 1), to obtain the title compound (0.32 g, yield 90%).

$^1$H NMR(400 MHz, CDCl$_3$)δ1.02(t, J=7.4 Hz, 3H), 1.54~1.61(m, 2H), 2.07(d, J=4.8 Hz, 1H), 2.74(d, J=4.8 Hz, 1H), 3.65~3.68(m, 1H), 5.01(t, J=5.0 Hz, 1H), 7.31~7.49(m, 3H)

Preparation Example 30

Synthesis of
1-(2,4-dichlorophenyl)-(R,R)-1,2-butanediol

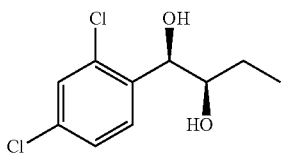

The substantially same method as described in Preparation Example 15 was conducted, except that 1-(2,4-dichlorophenyl)-trans-1-butene (Preparation Example 6) was used instead of 1-(2-chlorophenyl)-trans-1-propene (Preparation Example 1), to obtain the title compound (0.43 g, yield 60~90%).

$^1$H NMR(400 MHz, CDCl$_3$)δ1.02(t, J=7.4 Hz, 3H), 1.54=1.61(m, 2H), 2.07(d, J=4.8 Hz, 1H), 2.74(d, J=4.8 Hz, 1H), 3.65~3.68(m, 1H), 5.01(t, J=5.0 Hz, 1H), 7.31~7.49(m, 3H)

Preparation Example 31

Synthesis of the mixture of 1-(2,4-dichlorophenyl)-(S,S)-1,2-butanediol and 1-(2,4-dichlorophenyl)-(R,R)-1,2-butanediol

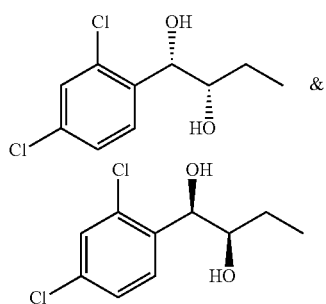

The substantially same method as described in Preparation Example 16 was conducted, except that 1-(2,4-dichlorophenyl)-trans-1-butene (Preparation Example 6) was used instead of 1-(2-chlorophenyl)-trans-1-propene (Preparation Example 1), to obtain the title compound (0.33 g, yield 60~90%).

$^1$H NMR(400 MHz, CDCl$_3$)δ1.02(t, J=7.4 Hz, 3H), 1.54~1.61(m, 2H), 2.07(d, J=4.8 Hz, 1H), 2.74(d, J=4.8 Hz, 1H), 3.65~3.68(m, 1H), 5.01(t, J=5.0 Hz, 1H), 77.31~7.49 (m, 3H)

Preparation Example 32

Synthesis of 1-(2,4-dichlorophenyl)-3-methyl-(S,S)-1,2-butanediol

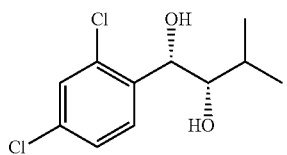

The substantially same method as described in Preparation Example 14 was conducted, except that 1-(2,4-dichlorophenyl)-3-methyl-trans-1-butene (Preparation Example 7) was used instead of 1-(2-chlorophenyl)-trans-1-propene (Preparation Example 1), to obtain the title compound (0.25 g, yield 60~95%).

$^1$H NMR(400 MHz, CDCl$_3$)δ1.00(d, J=6.8 Hz, 6H), 1.60~1.65(m, 1H), 2.35(d, J=4.0 Hz, 1H), 3.12(d, J=8.4 Hz, 1H), 4.13~4.18(m, 1H), 5.36(t, J=7.6 Hz, 1H), 7.17~7.35(m, 3H)

Preparation Example 33

Synthesis of 1-(2,4-dichlorophenyl)-3-methyl-(R,R)-1,2-butanediol

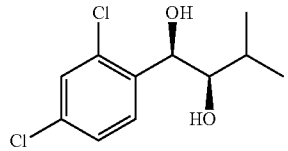

The substantially same method as described in Preparation Example 15 was conducted, except that 1-(2,4-dichlorophenyl)-3-methyl-trans-1-butene (Preparation Example 7) was used instead of 1-(2-chlorophenyl)-trans-1-propene (Preparation Example 1), to obtain the title compound (0.36 g, yield 60~95%).

$^1$H NMR(400 MHz, CDCl$_3$) δ1.00(d, J=6.8 Hz, 6H), 1.60~1.65(m, 1H), 2.35(d, J=4.0 Hz, 1H), 3.12(d, J=8.4 Hz, 1H), 4.13~4.18(m, 1H), 5.36(t, J=7.6 Hz, 1H), 7.17~7.35(m, 3H)

Preparation Example 34

Synthesis of the mixture of 1-(2,4-dichlorophenyl)-3-methyl-(S,S)-1,2-butanediol and 1-(2,4-dichlorophenyl)-3-methyl-(R,R)-1,2-butanediol

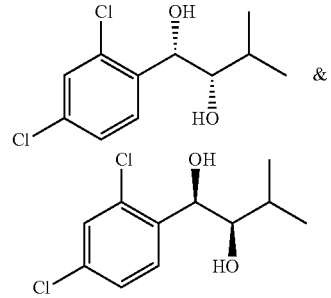

The substantially same method as described in Preparation Example 16 was conducted, except that 1-(2,4-dichlorophenyl)-3-methyl-trans-1-butene (Preparation Example 7) was used instead of 1-(2-chlorophenyl)-trans-1-propene (Preparation Example 1), to obtain the title compound (0.26 g, yield 60~95%).

$^1$H NMR(400 MHz, CDCl$_3$) δ1.00(d, J=6.8 Hz, 6H), 1.60~1.65(m, 1H), 2.35(d, J=4.0 Hz, 1H), 3.12(d, J=8.4 Hz, 1H), 4.13~4.18(m, 1H), 5.36(t, J=7.6 Hz, 1H), 7.17~7.35(m, 3H)

Preparation Example 35

Synthesis of 1-(2,4-dichlorophenyl)-(S,S)-1,2-hexanediol

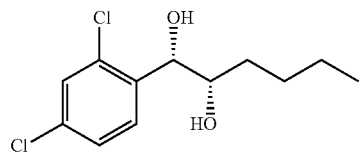 [SMILES: CCCC[C@H](O)[C@@H](O)c1ccc(Cl)cc1Cl]

The substantially same method as described in Preparation Example 14 was conducted, except that 1-(2,4-dichlorophenyl)-trans-1-hexene (Preparation Example 8) was used instead of 1-(2-chlorophenyl)-trans-1-propene (Preparation Example 1), to obtain the title compound (1.1 g, yield 60~90%).

$^1$H NMR(400 MHz, CDCl$_3$) δ0.89~0.93(m, 3H), 1.30~1.39(m, 2H), 1.49~1.52(m, 2H), 1.56~1.62(m, 2H), 2.05(d, J=5.2 Hz, 1H), 2.74(d, J=5.2 Hz, 1H), 3.72~3.77(m, 1H), 4.98(t, J=4.8 Hz, 1H), 7.28~7.50(m, 3H)

Preparation Example 36

Synthesis of
1-(2,4-dichlorophenyl)-(R,R)-1,2-hexanediol

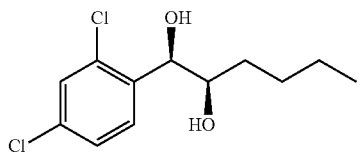 [SMILES: CCCC[C@@H](O)[C@H](O)c1ccc(Cl)cc1Cl]

The substantially same method as described in Preparation Example 15 was conducted, except that 1-(2,4-dichlorophenyl)-trans-1-hexene (Preparation Example 8) was used instead of 1-(2-chlorophenyl)-trans-1-propene (Preparation Example 1), to obtain the title compound (1.2 g, yield 60~95%).

$^1$H NMR(400 MHz, CDCl$_3$) δ0.89~0.93(m, 3H), 1.30~1.39(m, 2H), 1.49~1.52(m, 2H), 1.56~1.62(m, 2H), 2.05(d, J=5.2 Hz, 1H), 2.74(d, J=5.2 Hz, 1H), 3.72~3.77(m, 1H), 4.98(t, J=4.8 Hz, 1H), 7.28~7.50(m, 3H)

Preparation Example 37

Synthesis of the mixture of 1-(2,4-dichlorophenyl)-(S,S)-1,2-hexanediol and 1-(2,4-dichlorophenyl)-(R,R)-1,2-hexanediol

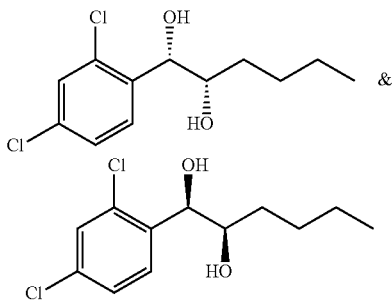

The substantially same method as described in Preparation Example 16 was conducted, except that 1-(2,4-dichlorophenyl)-trans-1-hexene (Preparation Example 8) was used instead of 1-(2-chlorophenyl)-trans-1-propene (Preparation Example 1), to obtain the title compound (0.67 g, yield 60~95%).

$^1$H NMR(400 MHz, CDCl$_3$) δ0.89~0.93(m, 3H), 1.30~1.39(m, 2H), 1.49~1.52(m, 2H), 1.56~1.62(m, 2H), 2.05(d, J=5.2 Hz, 1H), 2.74(d, J=5.2 Hz, 1H), 3.72~3.77(m, 1H), 4.98(t, J=4.8 Hz, 1H), 7.28~7.50(m, 3H)

Preparation Example 38

Synthesis of
1-(2,6-dichlorophenyl)-(S,S)-1,2-propanediol

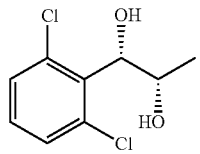

The substantially same method as described in Preparation Example 14 was conducted, except that 1-(2,6-dichlorophenyl)-trans-1-propene (Preparation Example 9) was used instead of 1-(2-chlorophenyl)-trans-1-propene (Preparation Example 1), to obtain the title compound (0.9 g, yield 60~90%).

$^1$H NMR(400 MHz, CDCl$_3$) δ1.10(d, J=6.4 Hz, 3H), 2.72(d, J=2.4 Hz, 1H), 3.10(d, J=8.4 Hz, 1H), 4.47~4.54(m, 1H), 5.24(t, J=8.8 Hz, 1H), 7.18~7.36(m, 3H)

Preparation Example 39

Synthesis of
1-(2,6-dichlorophenyl)-(R,R)-1,2-propanediol

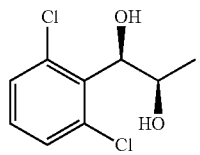

The substantially same method as described in Preparation Example 15 was conducted, except that 1-(2,6-dichlorophenyl)-trans-1-propene (Preparation Example 9) was used instead of 1-(2-chlorophenyl)-trans-1-propene (Preparation Example 1), to obtain the title compound (0.84 g, yield 60~90%).

$^1$H NM(400 MHz, CDCl$_3$) δ1.10(d, J=6.4 Hz, 3H), 2.72 (d, J=2.4 Hz, 1H), 3.10(d, J=8.4 Hz, 1H), 4.47~4.54(m, 1H), 5.24(t, J=8.8 Hz, 1H), 7.18~7.36(m, 3H)

Preparation Example 40

Synthesis of the mixture of 1-(2,6-dichlorophenyl)-(S,S)-1,2-propanediol and 1-(2,6-dichlorophenyl)-(R,R)-1,2-propanediol

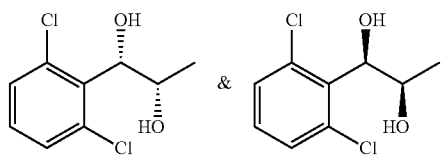

The substantially same method as described in Preparation Example 16 was conducted, except that 1-(2,6-dichlorophenyl)-trans-1-propene (Preparation Example 9) was used instead of 1-(2-chlorophenyl)-trans-1-propene (Preparation Example 1), to obtain the title compound (0.91 g, yield 60~90%).

¹H NMR(400 MHz, CDCl₃) δ1.10(d, J=6.4 Hz, 3H), 2.72(d, J=2.4 Hz, 1H), 3.10(d, J=8.4 Hz, 1H), 4.47~4.54(m, 1H), 5.24(t, J=8.8 Hz, 1H), 7.18~7.36(m, 3H)

Preparation Example 41

Synthesis of 1-(2,6-dichlorophenyl)-(S,S)-1,2-butanediol

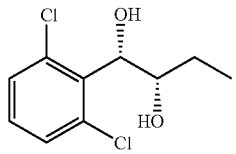

The substantially same method as described in Preparation Example 14 was conducted, except that 1-(2,6-dichlorophenyl)-trans-1-butene (Preparation Example 10) was used instead of 1-(2-chlorophenyl)-trans-1-propene (Preparation Example 1), to obtain the title compound (1.23 g, yield 60~95%).

¹H NMR(400 MHz, CDCl₃) δ0.97(t, J=7.6 Hz, 3H), 1.26~1.53(m, 2H), 2.64(dd, J=0.8 Hz, J=4.0 Hz, 1H), 3.14 (d, J=8.4 Hz, 1H), 4.22~4.26(m, 1H), 5.26(t, J=8.4 Hz, 1H), 7.17~7.35(m, 3H)

Preparation Example 42

Synthesis of 1-(2,6-dichlorophenyl)-(R,R)-1,2-butanediol

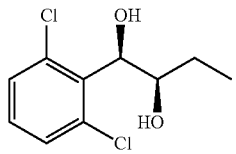

The substantially same method as described in Preparation Example 15 was conducted, except that 1-(2,6-dichlorophenyl)-trans-1-butene (Preparation Example 10) was used instead of 1-(2-chlorophenyl)-trans-1-propene (Preparation Example 1), to obtain the title compound (0.96 g, yield 60~95%).

¹H NMR(400 MHz, CDCl₃) δ0.97(t, J=7.6 Hz, 3H), 1.26~1.53(m, 2H), 2.64(dd, J=0.8 Hz, J=4.0 Hz, 1H), 3.14 (d, J=8.4 Hz, 1H), 4.22~4.26(m, 1H), 5.26(t, J=8.4 Hz, 1H), 7.17~7.35(m, 3H)

Preparation Example 43

Synthesis of the mixture of 1-(2,6-dichlorophenyl)-(S,S)-1,2-butanediol and 1-(2,6-dichlorophenyl)-(R,R)-1,2-butanediol

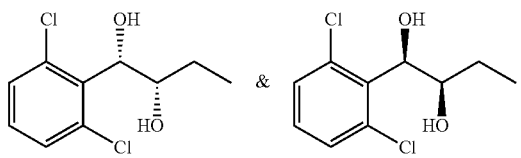

The substantially same method as described in Preparation Example 16 was conducted, except that 1-(2,6-dichlorophenyl)-trans-1-butene (Preparation Example 10) was used instead of 1-(2-chlorophenyl)-trans-1-propene (Preparation Example 1), to obtain the title compound (0.86 g, yield 60~95%).

¹H NMR(400 MHz, CDCl₃) δ0.97(t, J=7.6 Hz, 3H), 1.26~1.53(m, 2H), 2.64(dd, J=0.8 Hz, J=4.0 Hz, 1H), 3.14 (d, J=8.4 Hz, 1H), 4.22~4.26(m, 1H), 5.26(t, J=8.4 Hz, 1H), 7.17~7.35(m, 3H)

Preparation Example 44

Synthesis of 1-(2,6-dichlorophenyl)-3-methyl-(S,S)-1,2-butanediol

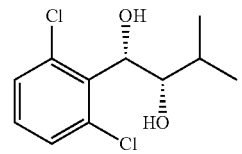

The substantially same method as described in Preparation Example 14 was conducted, except that 1-(2,6-dichlorophenyl)-3-methyl-trans-1-butene (Preparation Example 11) was used instead of 1-(2-chlorophenyl)-trans-1-propene (Preparation Example 1), to obtain the title compound (0.25 g, yield 60~95%).

¹H NMR(400 MHz, CDCl₃) δ1.00(d, J=6.8 Hz, 6H), 1.60~1.65(m, 1H), 2.35(d, J=4.0 Hz, 1H), 3.12(d, J=8.4 Hz, 1H), 4.13~4.18(m, 1H), 5.36(t, J=7.6 Hz, 1H), 7.17~7.35(m, 3H)

Preparation Example 45

Synthesis of 1-(2,6-dichlorophenyl)-3-methyl-(R,R)-1,2-butanediol

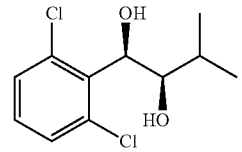

The substantially same method as described in Preparation Example 15 was conducted, except that 1-(2,6-dichlorophenyl)-3-methyl-trans-1-butene (Preparation Example 11) was used instead of 1-(2-chlorophenyl)-trans-1-propene (Preparation Example 1), to obtain the title compound (0.37 g, yield 60~95%).

¹H NMR(400 MHz, CDCl₃) δ1.00(d, J=6.8 Hz, 6H), 1.60~1.65(m, 1H), 2.35(d, J=4.0 Hz, 1H), 3.12(d, J=8.4 Hz, 1H), 4.13~4.18(m, 1H), 5.36(t, J=7.6 Hz, 1H), 7.17~7.35(m, 3H)

Preparation Example 46

Synthesis of the mixture of 1-(2,6-dichlorophenyl)-3-methyl-(S,S)-1,2-butanediol and 1-(2,6-dichlorophenyl)-3-methyl-(R,R)-1,2-butanediol

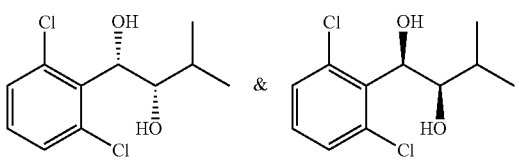

The substantially same method as described in Preparation Example 16 was conducted, except that 1-(2,6-dichlorophenyl)-3-methyl-trans-1-butene (Preparation Example 11) was used instead of 1-(2-chlorophenyl)-trans-1-propene (Preparation Example 1), to obtain the title compound (0.47 g, yield 60~95%).

¹H NMR(400 MHz, CDCl₃) δ1.00(d, J=6.8 Hz, 6H), 1.60~1.65(m, 1H), 2.35(d, J=4.0 Hz, 1H), 3.12(d, J=8.4 Hz, 1H), 4.13~4.18(m, 1H), 5.36(t, J=7.6 Hz, 1H), 7.17~7.35(m, 3H)

Preparation Example 47

Synthesis of 1-(2,6-dichlorophenyl)-(S,S)-1,2-hexanediol

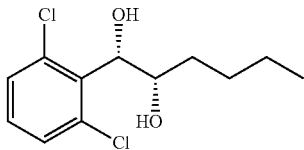 [SMILES: CCCC[C@H](O)[C@@H](O)c1c(Cl)cccc1Cl]

The substantially same method as described in Preparation Example 14 was conducted, except that 1-(2,6-dichlorophenyl)-trans-1-hexene (Preparation Example 12) was used instead of 1-(2-chlorophenyl)-trans-1-propene (Preparation Example 1), to obtain the title compound (0.36 g, yield 60~90%).

¹H NMR(400 MHz, CDCl₃) δ0.85(t, J=6.8 Hz, 3H), 1.20~1.31(m, 4H), 1.45~1.53(m, 2H), 2.61~2.62(m, 1H), 3.12(d, J=8.4 Hz, 1H), 4.28~4.33(m, 1H), 5.25(t, J=8.4 Hz, 1H), 7.18~7.35(m, 3H)

Preparation Example 48

Synthesis of 1-(2,6-dichlorophenyl)-(R,R)-1,2-hexanediol

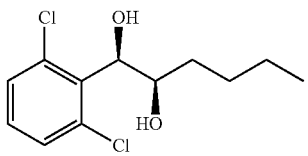 [SMILES: CCCC[C@@H](O)[C@H](O)c1c(Cl)cccc1Cl]

The substantially same method as described in Preparation Example 15 was conducted, except that 1-(2,6-dichlorophenyl)-trans-1-hexene (Preparation Example 12) was used instead of 1-(2-chlorophenyl)-trans-1-propene (Preparation Example 1), to obtain the title compound (0.58 g, yield 60~90%).

¹H NMR(400 MHz, CDCl₃) δ0.85(t, J=6.8 Hz, 3H), 1.20~1.31(m, 4H), 1.45~1.53(m, 2H), 2.61~2.62(m, 1H), 3.12(d, J=8.4 Hz, 1H), 4.28~4.33(m, 1H), 5.25(t, J=8.4 Hz, 1H), 7.18~7.35(m, 3H)

Preparation Example 49

Synthesis of the mixture of 1-(2,6-dichlorophenyl)-(S,S)-1,2-hexanediol and 1-(2,6-dichlorophenyl)-(R,R)-1,2-hexanediol

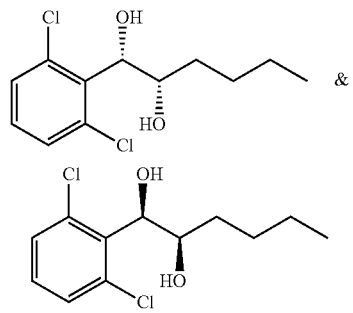

The substantially same method as described in Preparation Example 16 was conducted, except that 1-(2,6-dichlorophenyl)-trans-1-hexene (Preparation Example 12) was used instead of 1-(2-chlorophenyl)-trans-1-propene (Preparation Example 1), to obtain the title compound (0.62 g, yield 60~90%).

¹H NMR(400 MHz, CDCl₃) δ0.85(t, J=6.8 Hz, 3H), 1.20~1.31(m, 4H), 1.45~1.53(m, 2H), 2.61~2.62(m, 1H), 3.12(d, J=8.4 Hz, 1H), 4.28~4.33(m, 1H), 5.25(t, J=8.4 Hz, 1H), 7.18~7.35(m, 3H)

Preparation Example 50

Synthesis of methyl 2-(2-chlorophenyl)-(R)-2-hydroxyacetate

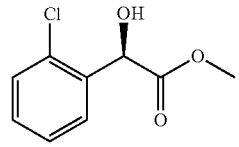

15 g of (R)-2-chloromandelic acid was mixed with methanol (CH₃OH, 150 ml) and phosphorus chloride oxide (POCl₃, 0.76 ml) in a flask by stirring using a magnetic stirrer at the room temperature for 6 hours. When the reaction was completed, the obtained product was washed with an aqueous solution of sodium sulfite (Na₂SO₃) and ethylacetate (EA). Then, the organic layer was dehydrated with anhydrous magnesium sulfate (MgSO₄), filtrated, and concented under reduced pressure. The concentrated residue was purified by a silica gel column chromatography to produce the title compound (15.64 g, yield 95%).

¹H NMR(400 MHz, CDCl₃) δ 3.59(d, J=5.2, 1H), 3.79(t, J=6.0, 3H), 5.59(d, J=5.2, 1H), 7.28~7.43(m, 4H)

Preparation Example 51

Synthesis of 2-(2-chlorophenyl)-(R)-2-hydroxy-N-methoxy-N-methylacetamide

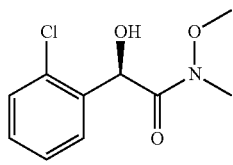

N,O-dimethylhydroxylamine hydrochloride (N,O-dimethylhydroxylamine.HCl, 15.2 g) was dissolved in dichloromethane (DCM, 150 ml), and cooled to 0° C. using an ice-bath. Then, 77.7 ml of 2.0M trimethylaluminium in hexane was slowly added thereto in drop-wise manner for 30 minutes. Thereafter, the ice-bath was removed, and the obtained product was stirred at the room temperature for 2 hours. Methyl-2-(2-chlorophenyl)-(R)-2-hydroxyacetate (15.64 g) dissolved in dichloromethane (DCM, 150 ml) was added in drop-wise manner thereto at the room temperature for 30 minutes, and subjected to reflux for 12 hours. When the reaction was completed, the obtained product was cooled to 0° C., and washed by a slow drop-wise addition of hydrochloric acid (HCl, 200 ml). The obtained organic layer was washed with distilled water and brine, dehydrated with anhydrous magnesium sulfate (MgSO$_4$), filtrated, and concented under reduced pressure. The concentrated residue was purified by a silica gel column chromatography to produce the title compound (14.68 g, yield 82%).

$^1$H NMR(400 MHz, CDCl$_3$) δ3.23(s, 3H), 3.28(s, 3H), 4.33(d, J=6.0 Hz, 1H), 5.81(d, J=5.6 Hz, 1H), 7.23~7.42(m, 4H)

Preparation Example 52

Synthesis of 2-(2-chlorophenyl)-N-methoxy-(R)-2-(t-butyl dimethlysiloxy)-N-methylacetamide

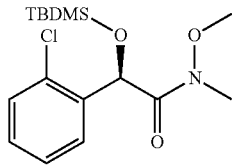

2-(2-chlorophenyl)-(R)-2-hydroxy-N-methoxy-N-methylacetamide (0.81 g, 3.52 mmol) obtained in Preparation Example 51 was dissolved in dichloromethane (DCM), and cooled to 0° C. Imedazole (0.36 g, 5.28 mmol) was slowly added, and stirred. TBDMS-Cl (t-butyldimethylsily chloride, 0.79 g, 5.28 mmol) was slowly added. When the reaction was completed, the reaction mixture was quenched with H$_2$O. The organic layer was separated and collected. The aqueous layer was extracted with CH$_2$Cl$_2$(300 mL), dried over MgSO$_4$. Concentration under vacuum provided a title compound. (0.97 g, 80~95%).

$^1$H NMR(400 MHz, CDCl$_3$) δ–0.03(s, 3H), 0.14(s, 3H), 0.94(s, 9H), 2.97(s, 3H), 3.02(s, 3H), 5.83(s, 1H), 7.25~7.60 (m, 4H)

Preparation Example 53

Synthesis of 1-(2-chlorophenyl)-(R)-1-(t-butyldimethyl-siloxy)propane-2-on

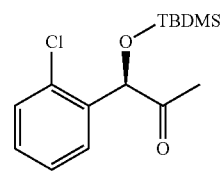

2-(2-chlorophenyl)-N-methoxy-(R)-2-(t-butyldimethylsiloxy)-N-methylacetamide(0.9 g) obtained in Preparation Example 52 was dissolved in tetrahydrofuran (THF), and cooled to 0° C. 3.0M methyl magnesium bromide (MeMgBr, 2.18 ml) solution in ether was added thereto in drop-wise manner for 30 minutes, and the obtained product was stirred at 0° C. When the reaction was completed, diethylether was added thereto. The obtained product was washed with 10% (w/v) potassium hydrogen sulfate (KHSO$_4$, 100 ml) and then, washed again with brine. The obtained organic layer was dehydrated with anhydrous magnesium sulfate (MgSO$_4$), filtrated, and concentrated under reduced pressure. The concentrated residue was purified by a silica gel column chromatography to produce the title compound (0.69 g, yield 85~95%).

$^1$H NMR(400 MHz, CDCl$_3$) δ–0.3(s, 3H), 0.14(s, 3H), 0.94(s, 9H), 2.18(s, 3H), 5.50(s, 1H), 7.27~7.56(m, 4H)

Preparation Example 54

Synthesis of 1-(2-chlorophenyl)-(R)-1-(t-butyldimethyl-siloxy)-(S)-2-propanol

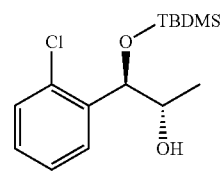

1-(2-chlorophenyl)-(R)-1-(t-butyldimethyl-siloxy)propane-2-on (0.14 g) obtained in Preparation Example 53 was dissolved in ether, and cooled to −78° C. Zinc borohydride (Zn(BH$_4$)$_2$) was slowly added thereto and the obtained product was stirred. When the reaction was completed, the obtained product was washed by H$_2$O. The obtained organic layer was washed with H$_2$O, dehydrated with anhydrous magnesium sulfate (MgSO$_4$), filtrated, and concentrated under reduced pressure. The concentrated residue was purified by a silica gel column chromatography to produce the title compound (0.04 g, yield 25~33%, cis:trans=2:1).

$^1$H NMR(400 MHz, CDCl$_3$) δ −0.11(s, 3H), 0.11(s, 3H), 0.93(S, 9H), 1.07(d, J=6.4, 3H), 2.05(d, J=6.4, 1H), 4.01~4.05(m, 1H), 5.18(d, J=4.0, 1H), 7.20~7.56(m, 4H))

Preparation Example 55

Synthesis of
1-(2-chlorophenyl)-(R,S)-1,2-propanediol

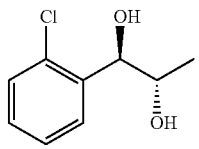

1-(2-chlorophenyl)-(R)-1-(t-butyldimethyl-siloxy)-(S)-2-propanol (10.38 g) obtained in Preparation Example 54 was dissolved in methanol (CH$_3$OH, 100 ml), and then, cooled to 0° C. 8M hydrochloric acid (HCl, 56.2 ml) was slowly added in drop-wise manner to the obtained product, and then, the obtained product was warmed to the room temperature, and stirred for 15 hours. When the reaction was completed, the obtained product was cooled to 0° C. 5N sodium hydroxide (NaOH, 30 ml) was slowly added thereto, and the obtained product was subjected to vacuum concentration. The obtained product was diluted with ethylacetate. The obtained organic layer was washed with distilled water, dehydrated with anhydrous magnesium sulfate (MgSO$_4$), filtrated, and concented under reduced pressure. The concentrated residue was purified by a silica gel column chromatography to produce the title compound (7.05 g, yield 60~90%).

$^1$H NMR(400 MHz, CDCl$_3$) δ1.07(d, J=6.8, 3H), 2.01(d, J=5.6, 1H), 2.61(s, 1H), 4.21~4.27(m, 1H), 5.24(d, J=3.6, 1H), 7.22~7.64(m, 4H)

Preparation Example 56

Synthesis of
1-(2-chlorophenyl)-(S,R)-1,2-propanediol

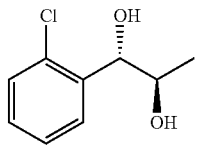

The substantially same method as described in Preparation Example 50~55 was conducted, except that (S)-2-chloromandelic acid was used instead of (R)-2-chloromandelic acid, to obtain the title compound (5.04 g, yield 84%).

$^1$H NMR(400 MHz, CDCl$_3$) δ1.07(d, J=6.8, 3H), 2.00(d, J=5.6, 1H), 2.54(d, J=3.6, 1H), 4.22~4.26(m, 1H), 5.25(t, J=3.2, 1H), 7.22~7.65(m, 4H)

Preparation Example 57

Synthesis of
1-(2,3-dichlorophenyl)-(S,S)-1,2-propanediol

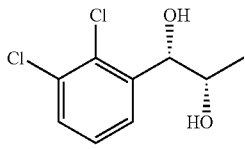

The substantially same method as described in Preparation Example 14 was conducted, except that 1-(2,3-dichlorophenyl)-trans-1-propene (Preparation Example 13) was used instead of 1-(2-chlorophenyl)-trans-1-propene (Preparation Example 1), to obtain the title compound (0.9 g, yield 60~90%).

$^1$H NMR(400 MHz, CDCl$_3$) δ1.10(d, J=6.4 Hz, 3H), 2.72(d, J=2.4 Hz, 1H), 3.10(d, J=8.4 Hz, 1H), 4.47~4.54(m, 1H), 5.24(t, J=8.8 Hz, 1H), 7.18~(m, 3H)

Preparation Example 58

Synthesis of
1-(2,3-dichlorophenyl)-(R,R)-1,2-propanediol

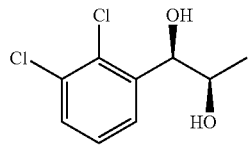

The substantially same method as described in Preparation Example 15 was conducted, except that 1-(2,3-dichlorophenyl)-trans-1-propene (Preparation Example 13) was used instead of 1-(2-chlorophenyl)-trans-1-propene (Preparation Example 1), to obtain the title compound (0.84 g, yield 60~90%).

$^1$H NMR(400 MHz, CDCl$_3$) δ1.10(d, J=6.4 Hz, 3H), 2.72(d, J=2.4 Hz, 1H), 3.10(d, J=8.4 Hz, 1H), 4.47~4.54(m, 1H), 5.24(t, J=8.8 Hz, 1H), 7.18~ (m, 3H)

Preparation Example 59

Synthesis of the mixture of 1-(2,3-dichlorophenyl)-(S,S)-1,2-propanediol and 1-(2,3-dichlorophenyl)-(R,R)-1,2-propanediol

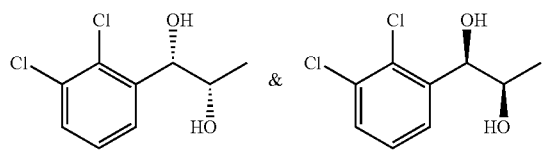

The substantially same method as described in Preparation Example 16 was conducted, except that 1-(2,3-dichlorophenyl)-trans-1-propene (Preparation Example 13) was used instead of 1-(2-chlorophenyl)-trans-1-propene (Preparation Example 1), to obtain the title compound (0.91 g, yield 60~90%).

$^1$H NMR(400 MHz, CDCl$_3$) δ1.10(d, J=6.4 Hz, 3H), 2.72(d, J=2.4 Hz, 1H), 3.10(d, J=8.4 Hz, 1H), 4.47~4.54(m, 1H), 5.24(t, J=8.8 Hz, 1H), 7.18~(m, 3H)

Preparation Example 60

Synthesis of 1-(2-fluorophenyl)-trans-1-propene

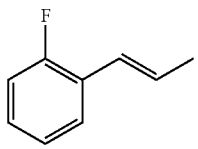

The substantially same method as described in Preparation Example 1 was conducted, except that 2-fluorobenzenaldehyde was used instead of 2-chlorobenzenealdehyde, to obtain the title compound (6.67 g, yield 61%).

¹H NMR(400 MHz, CDCl₃) δ1.94(d, J=6.8 Hz, 3H), 6.30~6.38(m, 1H), 6.57(d, J=16 Hz, 1H), 7.00~7.41(m, 4H)

Preparation Example 61

Synthesis of 1-(2-fluorophenyl)-(S,S)-1,2-propanediol

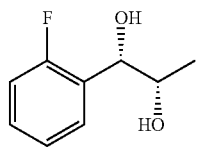

The substantially same method as described in Preparation Example 14 was conducted, except that 1-(2-fluorophenyl)-trans-1-propene (Preparation Example 60) was used instead of 1-(2-chlorophenyl)-trans-1-propene (Preparation Example 1), to obtain the title compound (6.46 g, yield 78%).

¹H NMR(400 MHz, CDCl₃) δ1.15(d, J=6.4 Hz, 3H), 2.43(d, J=3.6 Hz, 1H), 2.69(d, J=4.8 Hz, 1H), 3.90~3.98(m, 1H), 4.78(dd, J=4.4, 7.2 Hz, 1H), 7.04~7.50(m, 4H)

Preparation Example 62

Synthesis of 1-(2-fluorophenyl)-(R,R)-1,2-propanediol

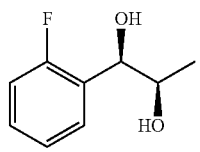

The substantially same method as described in Preparation Example 15 was conducted, except that 1-(2-fluorophenyl)-trans-1-propene (Preparation Example 60) was used instead of 1-(2-chlorophenyl)-trans-1-propene (Preparation Example 1), to obtain the title compound (3.29 g, yield 79%).

¹H NMR(400 MHz, CDCl₃) δ1.15(d, J=6.4 Hz, 3H), 2.43(d, J=3.6 Hz, 1H), 2.69(d, J=4.8 Hz, 1H), 3.90~3.98(m, 1H), 4.78(dd, J=4.4, 7.2 Hz, 1H), 7.04~7.50(m, 4H)

Preparation Example 63

Synthesis of 2-iodobenzenealdehyde

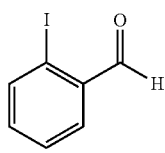

In a flask, 2-iodobenzyl alcohol (4 g, 17.09 mmol) was dissolved in dichloromethane (MC, 85 ml), and then, manganese oxide (MnO₂, 14.86 g, 170.92 mmol) was added thereto. The obtained reaction product was stirred under the reflux condition. When the reaction was completed, the obtained reaction product was cooled to the room temperature, and then, fiteated and concentrated using celite, to obtain the title compound (3.6 g, yield 91%).

¹H NMR(400 MHz, CDCl₃)δ7.30~7.99(m, 4H), 10.10(s, 1H)

Preparation Example 64

Synthesis of 1-(2-iodophenyl)-trans-1-propene

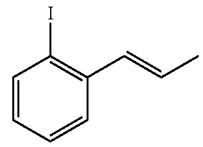

The substantially same method as described in Preparation Example 1 was conducted, except that 2-iodobenzenealdehyde (Preparation Example 63) was used instead of 2-chlorobenzenealdehyde, to obtain the title compound (3.4 g, yield 65%).

¹H NMR(400 MHz, CDCl₃)δ1.95(dd, J=6.8 Hz, 1.6 Hz, 3H), 6.09~6.18(m, 1H), 6.60(dd, J=15.66 Hz, 1.8 Hz, 1H), 6.89~7.84(m, 4H)

Preparation Example 65

Synthesis of 1-(2-iodophenyl)-trans-1-butene

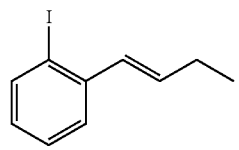

The substantially same method as described in Preparation Example 64 was conducted, except that 3-heptanone was used instead of 3-pentanone, to obtain the title compound (8.5 g, yield 75%).

¹H NMR(400 MHz, CDCl₃)δ1.46(t, J=7.6 Hz, 3H), 2.26~2.34(m, 2H), 6.17(dt, J=15.6 Hz, 6.6 Hz, 1H), 6.57(d, J=15.6 Hz, 1H), 6.89~7.85(m, 4H)

Preparation Example 66

Synthesis of 1-(2-iodophenyl)-(S,S)-1,2-propanediol

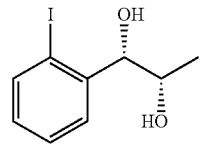

The substantially same method as described in Preparation Example 14 was conducted, except that 1-(2-iodophenyl)-trans-1-propene (Preparation Example 64) was used instead of 1-(2-chlorophenyl)-trans-1-propene (Preparation Example 1), to obtain the title compound (3.4 g, yield 88%).

¹H NMR(400 MHz, CDCl₃)δ1.27(d, J=6.4 Hz, 3H), 2.26 (br s, 1H), 2.74(br s, 1H), 3.99(t, J=6.0 Hz, 1H), 4.81(d, J=4.0 Hz, 1H), 7.01~7.87(m, 4H)

Preparation Example 67

Synthesis of 1-(2-iodophenyl)-(R,R)-1,2-propanediol

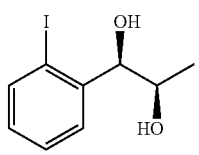

The substantially same method as described in Preparation Example 15 was conducted was conducted, except that 1-(2-iodophenyl)-trans-1-propene (Preparation Example 64) was used instead of 1-(2-chlorophenyl)-trans-1-propene (Preparation Example 1), to obtain the title compound (7.4 g, yield 84%).

¹H NMR(400 MHz, CDCl₃)δ1.26(d, J=6.4 Hz, 3H), 2.35 (br s, 1H), 2.85(br d, J=4.0 Hz, 1H), 3.98(t, J=6.2 Hz, 1H), 4.80(dd, J=5.0, 4.4 Hz, 1H), 7.00~7.87(m, 4H)

Preparation Example 68

Synthesis of 1-(2-iodophenyl)-(S,S)-1,2-butanediol

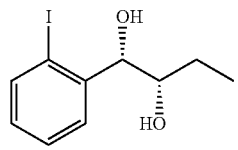

The substantially same method as described in Preparation Example 14 was conducted was conducted, except that 1-(2-iodophenyl)-trans-1-butene (Preparation Example 65) was used instead of 1-(2-chlorophenyl)-trans-1-propene (Preparation Example 1), to obtain the title compound (9.5 g, yield 84%).

¹H NMR(400 MHz, CDCl₃)δ1.04(t, J=7.6 Hz, 3H), 1.60~1.71(m, 2H), 2.07(br s, 1H), 2.74(br s, 1H), 3.71~3.76 (m, 1H), 4.87(d, J=4.8 Hz, 1H), 7.01~7.87(m, 4H)

Preparation Example 69

Preparation of 1-(2-chlorophenyl)-(S,S)-1,2-(Bis-trimethylsilanyloxy) propane

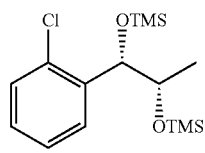

To a stirred solution of 1-(2-chlorophenyl)-(S,S)-1,2-propanediol (Preparation example 14, 67 g, 0.35 mol) in CH₂Cl₂(670 ml) was added Et₃N (200 mL, 1.43 mol) and TMSCl (113.9 mL, 0.89 mol) at 0° C. under N₂. The reaction mixture was allowed to stir at 0° C. for 3 hr. The reaction mixture was quenched with H₂O (650 mL) at 0° C. The organic layer was separated and collected. The aqueous layer was extracted with CH₂Cl₂(300 mL), dried over MgSO₄. Concentration under vacuum provided a crude product. 104.18 g (117.44%).

¹H NMR(400 MHz, CDCl₃)δ−0.053(s, 9H), 0.044(s, 9H), 1.15(d, J=5.6 Hz, 3H), 3.977~3.918(m, 1H), 4.973(d, J=6.4 Hz, 1H), 7.207~7.165(m, 1H), 7.321~7.245(m, 2H), 7.566~7.543(m, 1H)

Preparation Example 70

Preparation of 1-(2-chlorophenyl)-(R,R)-1,2-(Bis-trimethylsilanyloxy) propane

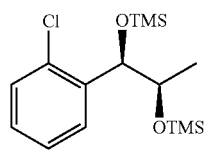

The substantially same method as described in Preparation Example 69 was conducted, except that 1-(2-chlorophenyl)-(R,R)-1,2-propanediol (Preparation example 15) was used instead of 1-(2-chlorophenyl)-(S,S)-1,2-propanediol (Preparation example 14) to obtain the title compound (8.5 g, yield 90~120%).

¹H NMR(400 MHz, CDCl₃)δ−0.053(s, 9H), 0.044(s, 9H), 1.15(d, J=5.6 Hz, 3H), 3.977~3.918(m, 1H), 4.973(d, J=6.4 Hz, 1H), 7.21~7.54(m, 4H)

Preparation Example 71

Preparation of 1-(2-chlorophenyl)-1,2-(Bis-trimethylsilanyloxy) propane

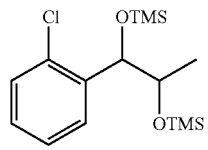

The substantially same method as described in Preparation Example 69 was conducted, except that 1-(2-chlorophenyl)propane-1,2-diol (Preparation example 16) was used instead of 1-(2-chlorophenyl)-(S,S)-1,2-propanediol (Preparation example 14) to obtain the title compound (5.2 g, yield 90~120%).

¹H NMR(400 MHz, CDCl₃)δ−0.053(s, 9H), 0.044(s, 9H), 1.15(d, J=5.6 Hz, 3H), 3.977~3.918(m, 1H), 4.973(d, J 6.4 Hz, 1H), 7.21~7.54(m, 4H)

Preparation Example 72

Preparation of 1-(2-chlorophenyl)-(S,R)-1,2-(Bis-trimethylsilanyloxy) propane

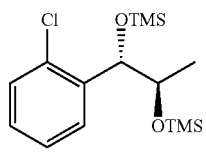

The substantially same method as described in Preparation Example 69 was conducted, except that 1-(2-chlorophenyl)-(S,R)-1,2-propanediol (Preparation example 56) was used instead of 1-(2-chlorophenyl)-(S,S)-1,2-propanediol (Preparation example 14) to obtain the title compound (3.4 g, yield 90~120%).
$^1$H NMR(400 MHz, CDCl$_3$)δ−0.053(s, 9H), 0.044(s, 9H), 1.15(d, J=5.6 Hz, 3H), 3.977~3.918(m, 1H), 4.973(d, J=6.4 Hz, 1H), 7.21~7.54(m, 4H)

Preparation Example 73

Preparation of 1-(2-chlorophenyl)-(R,S)-1,2-(Bis-trimethylsilanyloxy) propane

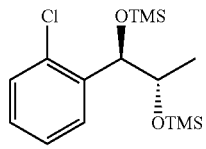

The substantially same method as described in Preparation Example 69 was conducted, except that 1-(2-chlorophenyl)-(R,S)-1,2-propanediol (Preparation example 55) was used instead of 1-(2-chlorophenyl)-(S,S)-1,2-propanediol (Preparation example 14) to obtain the title compound (3.2 g, yield 90~120%).
$^1$H NMR(400 MHz, CDCl$_3$)δ−0.053(s, 9H), 0.044(s, 9H), 1.15(d, J=5.6 Hz, 3H), 3.977~3.918(m, 1H), 4.973(d, J=6.4 Hz, 1H), 7.21~7.54(m, 4H)

Preparation Example 74

Preparation of 1-(2-chlorophenyl)-(S,S)-1,2-(Bis-trimethylsilanyloxy) butane

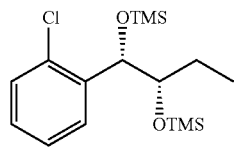

The substantially same method as described in Preparation Example 69 was conducted, except that 1-(2-chlorophenyl)-(S,S)-1,2-butanediol (Preparation example 17) was used instead of 1-(2-chlorophenyl)-(S,S)-1,2-propanediol (Preparation example 14) to obtain the title compound (3.6 g, yield 90~120%).
$^1$H NMR(400 MHz, CDCl$_3$)δ−0.053(s, 9H), 0.044(s, 9H), 1.01(t, J=7.4 Hz, 3H), 1.52~1.65(m, 2H), 3.69~3.75(m, 1H), 5.05(t, J=5.0 Hz, 1H), 7.23~7.54(m, 4H)

Preparation Example 75

Preparation of 1-(2-chlorophenyl)-(R,R)-1,2-(Bis-trimethylsilanyloxy) butane

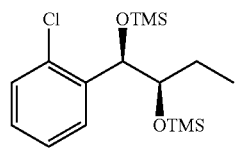

The substantially same method as described in Preparation Example 69 was conducted, except that 1-(2-chlorophenyl)-(R,R)-1,2-butanediol (Preparation example 18) was used instead of 1-(2-chlorophenyl)-(S,S)-1,2-propanediol (Preparation example 14) to obtain the title compound (3.5 g, yield 90~120%).
$^1$H NMR(400 MHz, CDCl$_3$)δ−0.053(s, 9H), 0.044(s, 9H), 1.01(t, J=7.4 Hz, 3H), 1.52~1.65(m, 2H), 3.69~3.75(m, 1H), 5.05(t, J=5.0 Hz, 1H), 7.23=7.54(m, 4H)

Preparation Example 76

Preparation of 1-(2-chlorophenyl)-1,2-(Bis-trimethylsilanyloxy) butane

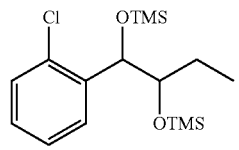

The substantially same method as described in Preparation Example 69 was conducted, except that 1-(2-chlorophenyl)-1,2-butanediol (Preparation example 19) was used instead of 1-(2-chlorophenyl)-(S,S)-1,2-propanediol (Preparation example 14) to obtain the title compound (3.0 g, yield 90~120%).
$^1$H NMR(400 MHz, CDCl$_3$)δ−0.053(s, 9H), 0.044(s, 9H), 1.01(t, J=7.4 Hz, 3H), 1.52~1.65(m, 2H), 3.69~3.75(m, 1H), 5.05(t, J=5.0 Hz, 1H), 7.23~7.54(m, 4H)

Preparation Example 77

Preparation of 1-(2-chlorophenyl)-3-methyl-(S,S)-1,2-(Bis-trimethylsilanyloxy)-butane

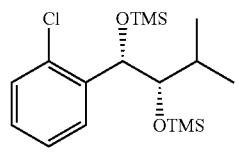

The substantially same method as described in Preparation Example 69 was conducted, except that 1-(2-chlorophenyl)-3-methyl-(S,S)-1,2-butanediol (Preparation example 20) was used instead of 1-(2-chlorophenyl)-(S,S)-1,2-propanediol (Preparation example 14) to obtain the title (2.7 g, yield 90~120%).
$^{1}$H NMR(400 MHz, CDCl$_3$)δ−0.053(s, 9H), 0.044(s, 9H), 1.07(t, J=7.2 Hz, 6H), 1.83~1.89(m, 1H), 3.53~3.56(m, 1H), 5.22~5.25(m, 1H), 7.23~7.55(m, 4H)

Preparation Example 78

Preparation of 1-(2-chlorophenyl)-3-methyl-(R,R)-1,2-(Bis-trimethylsilanyloxy)-butane

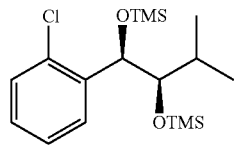

The substantially same method as described in Preparation Example 69 was conducted, except that 1-(2-chlorophenyl)-3-methyl-(R,R)-1,2-butanediol (Preparation example 21) was used instead of 1-(2-chlorophenyl)-(S,S)-1,2-propanediol (Preparation example 14) to obtain the title compound (2.4 g, yield 90~120%).
$^{1}$H NMR(400 MHz, CDCl$_3$)δ−0.053(s, 9H), 0.044(s, 9H), 1.07(t, J=7.2 Hz, 6H), 1.83~1.89(m, 1H), 3.53~3.56(m, 1H), 5.22~5.25(m, 1H), 7.23~7.55(m, 4H)

Preparation Example 79

Preparation of 1-(2-chlorophenyl)-3-methyl-1,2-(Bis-trimethylsilanyloxy)-butane

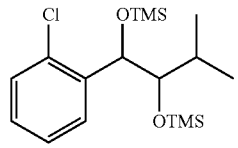

The substantially same method as described in Preparation Example 69 was conducted, except that 1-(2-chlorophenyl)-3-methyl-1,2-butanediol (Preparation example 22) was used instead of 1-(2-chlorophenyl)-(S,S)-1,2-propanediol (Preparation example 14) to obtain the title compound (2.8 g, yield 90~120%).
$^{1}$H NMR(400 MHz, CDCl$_3$)δ−0.053(s, 9H), 0.044(s, 9H), 1.07(t, J=7.2 Hz, 6H), 1.83~1.89(m, 1H), 3.53~3.56(m, 1H), 5.22~5.25(m, 1H), 7.23~7.55(m, 4H)

Preparation Example 80

Preparation of 1-(2-chlorophenyl)-(S,S)-1,2-(Bis-trimethylsilanyloxy)-hexane

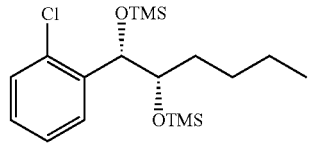

The substantially same method as described in Preparation Example 69 was conducted, except that 1-(2-chlorophenyl)-(S,S)-1,2-hexanediol (Preparation example 23) was used instead of 1-(2-chlorophenyl)-(S,S)-1,2-propanediol (Preparation example 14) to obtain the title compound (3.1 g, yield 90~120%).
$^{1}$H NMR(400 MHz, CDCl$_3$)δ−0.053(s, 9H), 0.044(s, 9H), 0.90(t, J=7.2 Hz, 3H), 1.35~1.65(m, 6H), 3.78~3.83(m, 1H), 5.04(t, J=5.0 Hz, 1H), 7.23~7.53(m, 4H)

Preparation Example 81

Preparation of 1-(2-chlorophenyl)-(S,S)-1,2-(Bis-trimethylsilanyloxy)-hexane

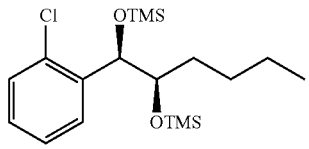

The substantially same method as described in Preparation Example 69 was conducted, except that 1-(2-chlorophenyl)-(R,R)-1,2-hexanediol (Preparation example 24) was used instead of 1-(2-chlorophenyl)-(S,S)-1,2-propanediol (Preparation example 14) to obtain the title compound (3.3 g, yield 90~120%).
$^{1}$H NMR(400 MHz, CDCl$_3$)δ−0.053(s, 9H), 0.044(s, 9H), 0.90(t, J=7.2 Hz, 3H), 1.35~1.65(m, 6H), 3.78~3.83(m, 1H), 5.04(t, J=5.0 Hz, 1H), 7.23~7.53(m, 4H)

Preparation Example 82

Preparation of 1-(2-chlorophenyl)-(S,S)-1,2-(Bis-trimethylsilanyloxy)-hexane

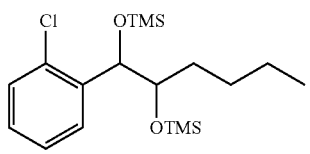

The substantially same method as described in Preparation Example 69 was conducted, except that 1-(2-chlorophenyl)-1,2-hexanediol (Preparation example 25) was used instead of 1-(2-chlorophenyl)-(S,S)-1,2-propanediol (Preparation example 14) to obtain the title compound (3.2 g, yield 90~120%).
$^{1}$H NMR(400 MHz, CDCl$_3$)δ−0.053(s, 9H), 0.044(s, 9H), 0.90(t, J=7.2 Hz, 3H), 1.35~1.65(m, 6H), 3.78~3.83(m, 1H), 5.04(t, J=5.0 Hz, 1H), 7.23~7.53(m, 4H)

Preparation Example 83

Preparation of 1-(2,4-dichlorophenyl)-(S,S)-1,2-(Bis-trimethylsilanyloxy)-propane

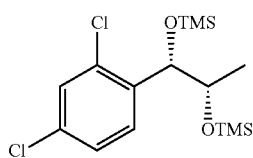

The substantially same method as described in Preparation Example 69 was conducted, except that 1-(2,4-dichlorophenyl)-(S,S)-1,2-propanediol (Preparation example 26) was used instead of 1-(2-chlorophenyl)-(S,S)-1,2-propanediol (Preparation example 14) to obtain the title compound (2.4 g, yield 90~120%).

¹H NMR(400 MHz, CDCl₃)δ–0.053(s, 9H), 0.044(s, 9H), 1.22(d, J=6.4 Hz, 3H), 3.90~3.95(m, 1H), 4.94(t, J=5.0 Hz, 1H), 7.31(dd, J=2.0 Hz, J=8.0 Hz, 1H), 7.40(d, J=2.0 Hz, 1H), 7.49(d, J=8.4 Hz, 1H)

Preparation Example 84

Preparation of 1-(2,6-dichlorophenyl)-(S,S)-1,2-(Bis-trimethylsilanyloxy)-propane

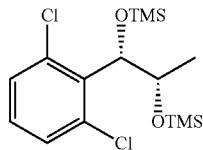

The substantially same method as described in Preparation Example 69 was conducted, except that 1-(2,6-dichlorophenyl)-(S,S)-1,2-propanediol (Preparation example 38) was used instead of 1-(2-chlorophenyl)-(S,S)-1,2-propanediol (Preparation example 14) to obtain the title compound (3.4 g, yield 90~120%).
¹H NMR(400 MHz, CDCl₃)δ–0.053(s, 9H), 0.044(s, 9H), 1.10(d, J=6.4 Hz, 3H), 4.47~4.54(m, 1H), 5.24(t, J=8.8 Hz, 1H), 7.13~7.36(m, 3H)

Preparation Example 85

Preparation of 1-(2,3-dichlorophenyl)-(S,S)-1,2-(Bis-trimethylsilanyloxy)-propane

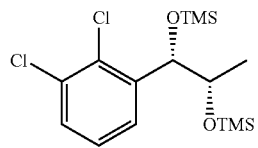

The substantially same method as described in Preparation Example 69 was conducted, except that 1-(2,3-dichlorophenyl)-(S,S)-1,2-propanediol (Preparation example 57) was used instead of 1-(2-chlorophenyl)-(S,S)-1,2-propanediol (Preparation example 14) to obtain the title compound (2.2 g, yield 90~120%).
¹H NMR(400 MHz, CDCl₃)δ–0.053(s, 9H), 0.044(s, 9H), 1.10(d, J=6.4 Hz, 3H), 4.47~4.54(m, 1H), 5.24(t, J=8.8 Hz, 1H), 7.18~7.22(m, 3H)

Preparation Example 86

Preparation of 1-(2,4-dichlorophenyl)-(S,S)-1,2-(Bis-trimethylsilanyloxy)-butane

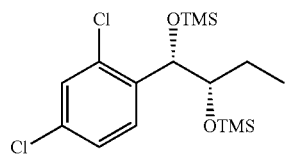

The substantially same method as described in Preparation Example 69 was conducted, except that 1-(2,4-dichlorophenyl)-(S,S)-1,2-butanediol (Preparation example 29) was used instead of 1-(2-chlorophenyl)-(S,S)-1,2-propanediol (Preparation example 14) to obtain the title compound (3.1 g, yield 90~120%).
¹H NMR(400 MHz, CDCl₃)δ–0.053(s, 9H), 0.044(s, 9H), 1.02(t, J=7.4 Hz, 3H), 1.54~1.61(m, 2H), 3.65~3.68(m, 1H), 5.01(t, J=5.0 Hz, 1H), 7.31~7.49(m, 3H)

Preparation Example 87

Preparation of 1-(2,6-dichlorophenyl)-(S,S)-1,2-(Bis-trimethylsilanyloxy)-butane

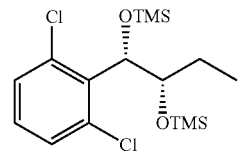

The substantially same method as described in Preparation Example 69 was conducted, except that 1-(2,6-dichlorophenyl)-(S,S)-1,2-butanediol (Preparation example 41) was used instead of 1-(2-chlorophenyl)-(S,S)-1,2-propanediol (Preparation example 14) to obtain the title compound (2.8 g, yield 90~120%).
¹H NMR(400 MHz, CDCl₃)δ–0.053(s, 9H), 0.044(s, 9H), 0.97(t, J=7.6 Hz, 3H), 1.26~1.53(m, 2H), 4.22~4.26(m, 1H), 5.26(t, J=8.4 Hz, 1H), 7.17~7.35(m, 3H)

Preparation Example 88

Preparation of 1-(2,4-dichlorophenyl)-3-methyl-(S,S)-1,2-(Bis-trimethylsilanyloxy)-butane

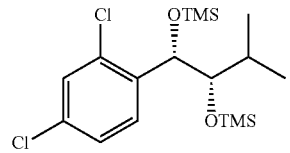

The substantially same method as described in Preparation Example 69 was conducted, except that 1-(2,4-dichlorophenyl)-3-methyl-(S,S)-1,2-butanediol (Preparation example 32) was used instead of 1-(2-chlorophenyl)-(S,S)-1,2-propanediol (Preparation example 14) to obtain the title compound (2.7 g, yield 90~120%).
¹H NMR(400 MHz, CDCl₃)δ–0.053(s, 9H), 0.044(s, 9H), 1.00(d, J=6.8 Hz, 6H), 1.60~1.65(m, 1H), 4.13~4.18(m, 1H), 5.36(t, J=7.6 Hz, 1H), 7.30~7.53(m, 3H)

Preparation Example 89

Preparation of 1-(2,6-dichlorophenyl)-3-methyl-(S,S)-1,2-(Bis-trimethylsilanyloxy)-butane

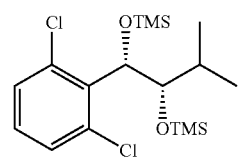

The substantially same method as described in Preparation Example 69 was conducted, except that 1-(2,6-dichlorophenyl)-3-methyl-(S,S)-1,2-butanediol (Preparation example 44) was used instead of 1-(2-chlorophenyl)-(S,S)-1,2-propanediol (Preparation example 14) to obtain the title compound (3.3 g, yield 90~120%).

$^1$H NMR(400 MHz, CDCl$_3$)δ−0.053(s, 9H), 0.044(s, 9H), 1.00(d, J=6.8 Hz, 6H), 1.60~1.65(m, 1H), 4.13~4.18(m, 1H), 5.36(t, J=7.6 Hz, 1H), 7.17~7.35(m, 3H)

Preparation Example 90

Preparation of 1-(2,4-dichlorophenyl)-(S,S)-1,2-(Bis-trimethylsilanyloxy)-hexane

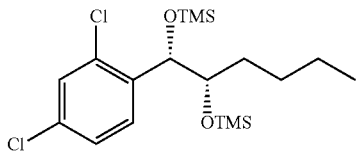

The substantially same method as described in Preparation Example 69 was conducted, except that 1-(2,4-dichlorophenyl)-(S,S)-1,2-hexanediol (Preparation example 90) was used instead of 1-(2-chlorophenyl)-(S,S)-1,2-propanediol (Preparation example 14) to obtain the title compound (3.6 g, yield 90~120%).

$^1$H NMR(400 MHz, CDCl$_3$)δ−0.053(s, 9H), 0.044(s, 9H), 0.89~0.93(m, 3H), 1.30~1.39(m, 2H), 1.49~1.52(m, 2H), 1.56~1.6(m, 2H), 3.72~3.77(m, 1H), 4.98(t, J=4.8 Hz, 1H), 7.28~7.50(m, 3H)

Preparation Example 91

Preparation of 1-(2,6-dichlorophenyl)-(S,S)-1,2-(Bis-trimethylsilanyloxy)-hexane

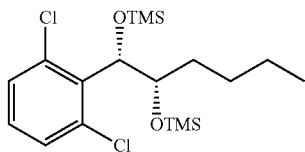

The substantially same method as described in Preparation Example 69 was conducted, except that 1-(2,6-dichlorophenyl)-(S,S)-1,2-hexanediol (Preparation example 47) was used instead of 1-(2-chlorophenyl)-(S,S)-1,2-propanediol (Preparation example 14) to obtain the title compound (2.8 g, yield 90~120%).

$^1$H NMR(400 MHz, CDCl$_3$)δ−0.053(s, 9H), 0.044(s, 9H), 0.85(t, J=6.7 Hz, 3H), 1.20~1.31(m, 4H), 1.45~1.53(m, 2H), 4.28~4.33(m, 1H), 5.25(t, J=8.4 Hz, 1H), 7.18~7.35(m, 3H)

Preparation Example 92

Preparation of 1-(2,4-dichlorophenyl)-(R,R)-1,2-(Bis-trimethylsilanyloxy)-propane

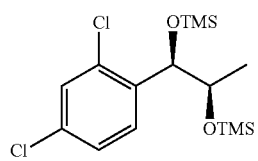

The substantially same method as described in Preparation Example 69 was conducted, except that 1-(2,4-dichlorophenyl)-(R,R)-1,2-propanediol (Preparation example 27) was used instead of 1-(2-chlorophenyl)-(S,S)-1,2-propanediol (Preparation example 14) to obtain the title compound (2.2 g, yield 90~120%).

$^1$H NMR(400 MHz, CDCl$_3$)δ−0.053(s, 9H), 0.044(s, 9H), 1.22(d, J=6.4 Hz, 3H), 3.90~3.95(m, 1H), 4.94(t, J=5.0 Hz, 1H), 7.31~7.49(m, 3H)

Preparation Example 93

Preparation of 1-(2,6-dichlorophenyl)-(R,R)-1,2-(Bis-trimethylsilanyloxy)-propane

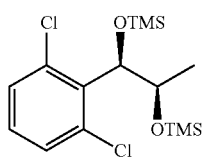

The substantially same method as described in Preparation Example 69 was conducted, except that 1-(2,6-dichlorophenyl)-(R,R)-1,2-propanediol (Preparation example 39) was used instead of 1-(2-chlorophenyl)-(S,S)-1,2-propanediol (Preparation example 14) to obtain the title compound (2.6 g, yield 90~120%).

$^1$H NMR(400 MHz, CDCl$_3$)δ−0.053(s, 9H), 0.044(s, 9H), 1.10(d, J=6.4 Hz, 3H), 4.47~4.54(m, 1H), 5.24(t, J=8.8 Hz, 1H), 7.18~7.36(m, 3H)

Preparation Example 94

Preparation of 1-(2,3-dichlorophenyl)-(R,R)-1,2-(Bis-trimethylsilanyloxy)-propane

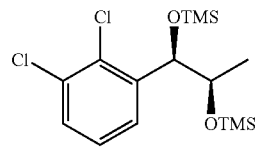

The substantially same method as described in Preparation Example 69 was conducted, except that 1-(2,3-dichlorophenyl)-(R,R)-1,2-propanediol (Preparation example 58) was used instead of 1-(2-chlorophenyl)-(S,S)-1,2-propanediol (Preparation example 14) to obtain the title compound (2.9 g, yield 90~120%).

$^1$H NMR(400 MHz, CDCl$_3$)δ−0.053(s, 9H), 0.044(s, 9H), 1.10(d, J=6.4 Hz, 3H), 4.47~4.54(m, 1H), 5.24(t, J=8.8 Hz, 1H), 7.18~7.22(m, 3H)

Preparation Example 95

Preparation of 1-(2,4-dichlorophenyl)-(R,R)-1,2-(Bis-trimethylsilanyloxy)-butane

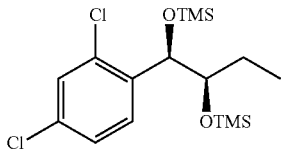

The substantially same method as described in Preparation Example 69 was conducted, except that 1-(2,4-dichlorophenyl)-(R,R)-1,2-butanediol (Preparation example 30) was used instead of 1-(2-chlorophenyl)-(S,S)-1,2-propanediol (Preparation example 14) to obtain the title compound (3.6 g, yield 90~120%).

¹H NMR(400 MHz, CDCl₃)δ−0.053(s, 9H), 0.044(s, 9H), 1.02(t, J=7.4 Hz, 3H), 1.54~1.61(m, 2H), 3.65~3.68(m, 1H), 5.01(t, J=5.0 Hz, 1H), 7.31~7.49(m, 3H)

Preparation Example 96

Preparation of 1-(2,6-dichlorophenyl)-(R,R)-1,2-(Bis-trimethylsilanyloxy)-butane

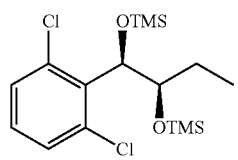

The substantially same method as described in Preparation Example 69 was conducted, except that 1-(2,6-dichlorophenyl)-(R,R)-1,2-butanediol (Preparation example 42) was used instead of 1-(2-chlorophenyl)-(S,S)-1,2-propanediol (Preparation example 14) to obtain the title compound (3.3 g, yield 90~120%).

¹H NMR(400 MHz, CDCl₃)δ−0.053(s, 9H), 0.044(s, 9H), 0.97(t, J=7.6 Hz, 3H), 1.26~1.53(m, 2H), 4.22~4.26(m, 1H), 5.26(t, J=8.4 Hz, 1H), 7.17~7.35(m, 3H)

Preparation Example 97

Preparation of 1-(2,4-dichlorophenyl)-3-methyl-(R,R)-1,2-(Bis-trimethylsilanyloxy)-butane

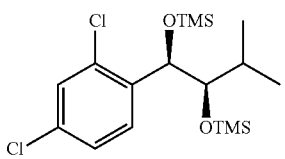

The substantially same method as described in Preparation Example 69 was conducted, except that 1-(2,4-dichlorophenyl)-3-methyl-(R,R)-1,2-butanediol (Preparation example 33) was used instead of 1-(2-chlorophenyl)-(S,S)-1,2-propanediol (Preparation example 14) to obtain the title compound (3.5 g, yield 90~120%).

¹H NMR(400 MHz, CDCl₃)δ−0.053(s, 9H), 0.044(s, 9H), 1.00(d, J=6.8 Hz, 6H), 1.60~1.65(m, 1H), 4.13~4.18(m, 1H), 5.36(t, J=7.6 Hz, 1H), 7.30~7.53(m, 3H)

Preparation Example 98

Preparation of 1-(2,6-dichlorophenyl)-3-methyl-(R,R)-1,2-(Bis-trimethylsilanyloxy)-butane

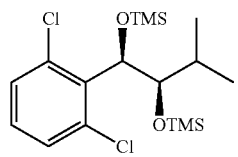

The substantially same method as described in Preparation Example 69 was conducted, except that 1-(2,6-dichlorophenyl)-3-methyl-(R,R)-1,2-butanediol (Preparation example 45) was used instead of 1-(2-chlorophenyl)-(S,S)-1,2-propanediol (Preparation example 14) to obtain the title compound (3.4 g, yield 90~120%).

¹H NMR(400 MHz, CDCl₃)δ−0.053(s, 9H), 0.044(s, 9H), 1.00(d, J=6.8 Hz, 6H), 1.60~1.65(m, 1H), 4.13~4.18(m, 1H), 5.36(t, J=7.6 Hz, 1H), 7.17~7.35(m, 3H)

Preparation Example 99

Preparation of 1-(2,4-dichlorophenyl)-(R,R)-1,2-(Bis-trimethylsilanyloxy)-hexane

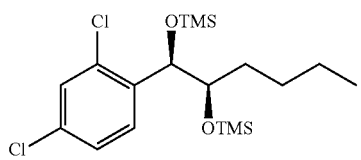

The substantially same method as described in Preparation Example 69 was conducted, except that 1-(2,4-dichlorophenyl)-(R,R)-1,2-hexanediol (Preparation example 36) was used instead of 1-(2-chlorophenyl)-(S,S)-1,2-propanediol (Preparation example 14) to obtain the title compound (3.6 g, yield 90~120%).

¹H NMR(400 MHz, CDCl₃)δ−0.053(s, 9H), 0.044(s, 9H), 0.89~0.93(m, 3H), 1.30~1.39(m, 2H), 1.49~1.52(m, 2H), 1.56~1.62(m, 2H), 3.72~3.77(m, 1H), 4.98(t, J=4.8 Hz, 1H), 7.28~7.50(m, 3H)

Preparation Example 100

Preparation of 1-(2,6-dichlorophenyl)-(R,R)-1,2-(Bis-trimethylsilanyloxy)-hexane

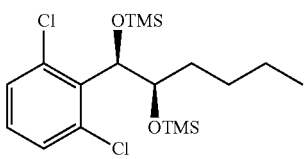

The substantially same method as described in Preparation Example 69 was conducted, except that 1-(2,6-dichlorophenyl)-(R,R)-1,2-hexanediol (Preparation example 48) was used instead of 1-(2-chlorophenyl)-(S,S)-1,2-propanediol (Preparation example 14) to obtain the title compound (3.3 g, yield 90~120%).

¹H NMR(400 MHz, CDCl₃)δ−0.053(s, 9H), 0.044(s, 9H), 0.85(t, J=6.7 Hz, 3H), 1.20~1.31(m, 4H), 1.45~1.53(m, 2H), 4.28~4.33(m, 1H), 5.25(t, J=8.4 Hz, 1H), 7.18~7.35(m, 3H)

Preparation Example 101

Preparation of 1-(2,4-dichlorophenyl)-1,2-(Bis-trimethylsilanyloxy)-propane

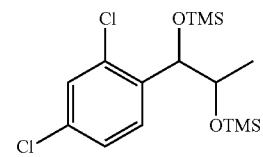

The substantially same method as described in Preparation Example 69 was conducted, except that 1-(2,4-dichlorophenyl)-1,2-propanediol (Preparation example 28) was used instead of 1-(2-chlorophenyl)-(S,S)-1,2-propanediol (Preparation example 14) to obtain the title compound (2.6 g, yield 90~120%).

¹H NMR(400 MHz, CDCl₃)δ−0.053(s, 9H), 0.044(s, 9H), 1.22(d, J=6.4 Hz, 3H), 3.90~3.95(m, 1H), 4.94(t, J=5.0 Hz, 1H), 7.31~7.49(m, 3H)

Preparation Example 102

Preparation of 1-(2,6-dichlorophenyl)-1,2-(Bis-trimethylsilanyloxy)-propane

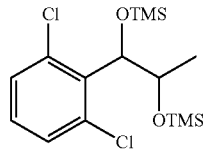

The substantially same method as described in Preparation Example 69 was conducted, except that 1-(2,6-dichlorophenyl)-1,2-propanediol (Preparation example 40) was used instead of 1-(2-chlorophenyl)-(S,S)-1,2-propanediol (Preparation example 14) to obtain the title compound (3.1 g, yield 90~120%).

¹H NMR(400 MHz, CDCl₃)δ−0.053(s, 9H), 0.044(s, 9H), 1.10(d, J=6.4 Hz, 3H), 4.47~4.54(m, 1H), 5.24(t, J=8.8 Hz, 1H), 7.18~7.36(m, 3H)

Preparation Example 103

Preparation of 1-(2,3-dichlorophenyl)-1,2-(Bis-trimethylsilanyloxy)-propane

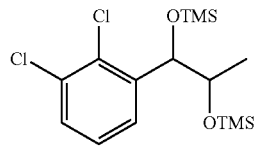

The substantially same method as described in Preparation Example 69 was conducted, except that 1-(2,3-dichlorophenyl)-1,2-propanediol (Preparation example 59) was used instead of 1-(2-chlorophenyl)-(S,S)-1,2-propanediol (Preparation example 14) to obtain the title compound (2.7 g, yield 90~120%).

¹H NMR(400 MHz, CDCl₃)δ−0.053(s, 9H), 0.044(s, 9H), 1.10(d, J=6.4 Hz, 3H), 4.47~4.54(m, 1H), 5.24(t, J=8.8 Hz, 1H), 7.18~7.22(m, 3H)

Preparation Example 104

Preparation of 1-(2,4-dichlorophenyl)-1,2-(Bis-trimethylsilanyloxy)-butane

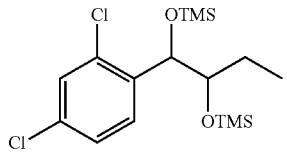

The substantially same method as described in Preparation Example 69 was conducted, except that 1-(2,4-dichlorophenyl)-1,2-butanediol (Preparation example 31) was used instead of 1-(2-chlorophenyl)-(S,S)-1,2-propanediol (Preparation example 14) to obtain the title compound (2.9 g, yield 90~120%).

¹H NMR(400 MHz, CDCl₃)δ−0.053(s, 9H), 0.044(s, 9H), 1.02(t, J=7.4 Hz, 3H), 1.54~1.61(m, 2H), 3.65~3.68(m, 1H), 5.01(t, J=5.0 Hz, 1H), 7.31~7.49(m, 3H)

Preparation Example 105

Preparation of 1-(2,6-dichlorophenyl)-1,2-(Bis-trimethylsilanyloxy)-butane

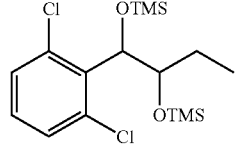

The substantially same method as described in Preparation Example 69 was conducted, except that 1-(2,6-dichlorophenyl)-1,2-butanediol (Preparation example 43) was used instead of 1-(2-chlorophenyl)-(S,S)-1,2-propanediol (Preparation example 14) to obtain the title compound (3.1 g, yield 90~120%).

¹H NMR(400 MHz, CDCl₃)δ−0.053(s, 9H), 0.044(s, 9H), 0.97(t, J=7.6 Hz, 3H), 1.26~1.53(m, 2H), 4.22~4.26(m, 1H), 5.26(t, J=8.4 Hz, 1H), 7.17~7.35(m, 3H)

Preparation Example 106

Preparation of 1-(2,4-dichlorophenyl)-3-methyl-1,2-(Bis-trimethylsilanyloxy)-butane

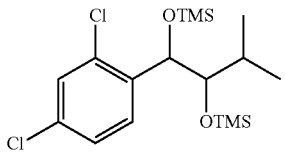

The substantially same method as described in Preparation Example 69 was conducted, except that 1-(2,4-dichlorophenyl)-3-methyl-1,2-butanediol (Preparation example 34) was used instead of 1-(2-chlorophenyl)-(S,S)-1,2-propanediol (Preparation example 14) to obtain the title compound (2.7 g, yield 90~120%).

¹H NMR(400 MHz, CDCl₃)δ−0.053(s, 9H), 0.044(s, 9H), 1.00(d, J=6.8 Hz, 6H), 1.60~1.65(m, 1H), 4.13~4.18(m, 1H), 5.36(t, J=7.6 Hz, 1H), 7.30~7.53(m, 3H)

Preparation Example 107

Preparation of 1-(2,6-dichlorophenyl)-3-methyl-1,2-(Bis-trimethylsilanyloxy)-butane

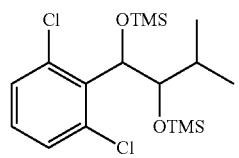

The substantially same method as described in Preparation Example 69 was conducted, except that 1-(2,6-dichlorophenyl)-3-methyl-1,2-butanediol (Preparation example 46) was used instead of 1-(2-chlorophenyl)-(S,S)-1,2-propanediol (Preparation example 14) to obtain the title compound (2.6 g, yield 90~120%).

$^1$H NMR(400 MHz, CDCl$_3$)δ−0.053(s, 9H), 0.044(s, 9H), 1.00(d, J=6.8 Hz, 6H), 1.60~1.65(m, 1H), 4.13~4.18(m, 1H), 5.36(t, J=7.6 Hz, 1H), 7.17~7.35(m, 3H)

Preparation Example 108

Preparation of 1-(2,4-dichlorophenyl)-1,2-(Bis-trimethylsilanyloxy)-hexane

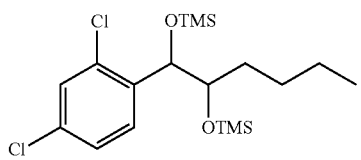

The substantially same method as described in Preparation Example 69 was conducted, except that 1-(2,4-dichlorophenyl)-1,2-hexanediol (Preparation example 37) was used instead of 1-(2-chlorophenyl)-(S,S)-1,2-propanediol (Preparation example 14) to obtain the title compound (3.7 g, yield 90~120%).

$^1$H NMR(400 MHz, CDCl$_3$)δ−0.053(s, 9H), 0.044(s, 9H), 0.89~0.93(m, 3H), 1.30~1.39(m, 2H), 1.49~1.52(m, 2H), 1.56~1.62(m, 2H), 3.72~3.77(m, 1H), 4.98(t, J=4.8 Hz, 1H), 7.28~7.50(m, 3H)

Preparation Example 109

Preparation of 1-(2,6-dichlorophenyl)-1,2-(Bis-trimethylsilanyloxy)-hexane

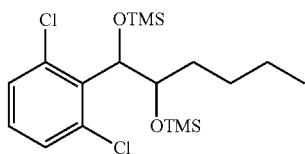

The substantially same method as described in Preparation Example 69 was conducted, except that 1-(2,6-dichlorophenyl)-1,2-hexanediol (Preparation example 49) was used instead of 1-(2-chlorophenyl)-(S,S)-1,2-propanediol (Preparation example 14) to obtain the title compound (3.2 g, yield 90~120%).

$^1$H NMR(400 MHz, CDCl$_3$)δ−0.053(s, 9H), 0.044(s, 9H), 0.85(t, J=6.7 Hz, 3H), 1.20~1.31(m, 4H), 1.45~1.53(m, 2H), 4.28~4.33(m, 1H), 5.25(t, J=8.4 Hz, 1H), 7.18~7.35(m, 3H)

Preparation Example 110

Preparation of 1-(2-fluorophenyl)-(S,S)-1,2-(Bis-trimethylsilanyloxy)-propane

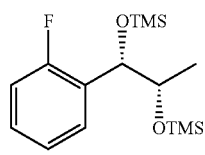

The substantially same method as described in Preparation Example 69 was conducted, except that 1-(2-fluorophenyl)-(S,S)-1,2-propanediol (Preparation example 61) was used instead of 1-(2-chlorophenyl)-(S,S)-1,2-propanediol (Preparation example 14) to obtain the title compound (2.8 g, yield 90~120%).

$^1$H NMR(400 MHz, CDCl$_3$)δ−0.053(s, 9H), 0.044(s, 9H), 1.15(d, J=6.4 Hz, 3H), 3.90~3.98(m, 1H), 4.78(dd, J=4.4, 7.2 Hz, 1H), 7.04~7.50(m, 4H)

Preparation Example 111

Preparation of 1-(2-fluorophenyl)-(R,R)-1,2-(Bis-trimethylsilanyloxy)-propane

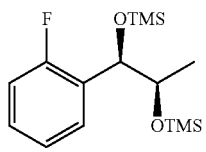

The substantially same method as described in Preparation Example 69 was conducted, except that 1-(2-fluorophenyl)-(R,R)-1,2-propanediol (Preparation example 62) was used instead of 1-(2-chlorophenyl)-(S,S)-1,2-propanediol (Preparation example 14) to obtain the title compound (2.5 g, yield 90~120%).

$^1$H NMR(400 MHz, CDCl$_3$)δ−0.053(s, 9H), 0.044(s, 9H), 1.15(d, J=6.4 Hz, 3H), 3.90~3.98(m, 1H), 4.78(dd, J=4.4, 7.2 Hz, 1H), 7.04~7.50(m, 4H)

Preparation Example 112

Preparation of 1-(2-iodophenyl)-(S,S)-1,2-(Bis-trimethylsilanyloxy)-propane

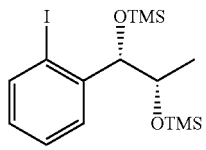

The substantially same method as described in Preparation Example 69 was conducted, except that 1-(2-iodophenyl)-(S,S)-1,2-propanediol (Preparation example 66) was used instead of 1-(2-chlorophenyl)-(S,S)-1,2-propanediol (Preparation example 14) to obtain the title compound (3.1 g, yield 90~120%).

$^1$H NMR(400 MHz, CDCl$_3$)δ−0.053(s, 9H), 0.044(s, 9H), 1.27(d, J=6.4 Hz, 3H), 3.99(t, J=6.0 Hz, 1H), 4.81(d, J=4.0 Hz, 1H), 7.01~7.87(m, 4H)

Preparation Example 113

Preparation of 1-(2-iodophenyl)-(R,R)-1,2-(Bis-trimethylsilanyloxy)-propane

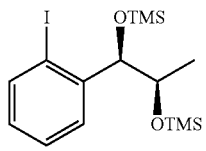

The substantially same method as described in Preparation Example 69 was conducted, except that 1-(2-iodophenyl)-(R,R)-1,2-propanediol (Preparation example 67) was used instead of 1-(2-chlorophenyl)-(S,S)-1,2-propanediol (Preparation example 14) to obtain the title compound (2.8 g, yield 90~120%).

$^1$H NMR(400 MHz, CDCl$_3$)δ−0.053(s, 9H), 0.044(s, 9H), 1.26(d, J=6.4 Hz, 3H), 3.98(t, J=6.2 Hz, 1H), 4.88(d, J=4.4 Hz, 1H), 7.00~7.87(m, 4H)

Preparation Example 114

Preparation of 1-(2-iodophenyl)-(S,S)-1,2-(Bis-trimethylsilanyloxy)-butane

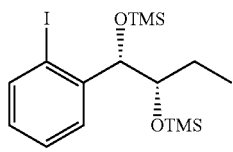

The substantially same method as described in Preparation Example 69 was conducted, except that 1-(2-iodophenyl)-(S,S)-1,2-butanediol (Preparation example 68) was used instead of 1-(2-chlorophenyl)-(S,S)-1,2-propanediol (Preparation example 14) to obtain the title compound (3.3 g, yield 90~120%).

$^1$H NMR(400 MHz, CDCl$_3$)δ−0.053(s, 9H), 0.044(s, 9H), 1.04(t, J=7.6 Hz, 3H), 1.60~1.71(m, 2H), 3.71~3.76(m, 1H), 4.87(d, J=4.8 Hz, 1H), 7.01~7.87(m, 4H)

Example 1

Preparation of 1-(2-chlorophenyl)-(S)-1-hydroxypropyl-(S)-2-carbamate(1)

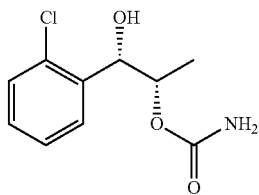

To a stirred solution of crude 1-(2-chlorophenyl)-(S,S)-1,2-(Bis-trimethylsilanyloxy) propane (preparation example 69, 104 g, 0.31 mol) in toluene (670 mL) was added by Chlorosulfonyl isocyanate (62.5 mL, 0.71 mol) at 0° C. The reaction mixture was stirred for 2 hr. The reaction mixture was quenched with ice water and then was stirred by additional cold H$_2$O (500 mL) for 2 hr. After separation of organic layer, the aqueous was adjusted pH2=3 with sat. NaHCO$_3$(400 mL) and extracted with EtOAc (300 mL×3). The EtOAc layer was washed with sat. NaHCO$_3$(500 mL) and H$_2$O (500 mL). The organic phase was treated with Charcol for 1.5 hr. The organic phase was filtered with Cellite, dried over MgSO$_4$. Filterion and concentration under vacuum provided the title compound of white solid (yield 85% (71.1 g), ee=99.9% MP=83~84° C., [α]$_D$=+57.8 (c=0.25, MeOH))

$^1$H NMR(400 MHz, CDCl$_3$) δ1.24(d, J=6.4, 3H), 2.91(d, J=4.8, 1H), 4.68(br s, 2H), 5.06~5.09(m, 1H), 5.18~5.21(m, 1H), 7.23~7.39(m, 3H), 7.55(dd, J=1.6, J=7.8, 1H)

$^{13}$C NMR (100 MHz, CDCl$_3$) δ16.4, 73.1, 75.0, 127.0, 128.4, 129.1, 129.5, 132.7, 138.0, 156.6

Example 2

Preparation of 1-(2-chlorophenyl)-(R)-1-hydroxypropyl-(R)-2-carbamate(2)

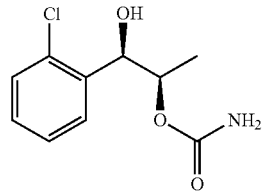

The substantially same method as described in Example 1 was conducted, except that 1-(2-chlorophenyl)-(R,R)-1,2-(Bis-trimethylsilanyloxy) propane (Preparation example 70) was used instead of 1-(2-chlorophenyl)-(S,S)-1,2-(Bis-trimethylsilanyloxy) propane (Preparation example 69) to obtain the title compound (5.7 g, yield 60~90%).

$^1$H NMR(400 MHz, CDCl$_3$) δ1.24(d, J=6.4, 3H), 2.91(d, J=4.8, 1H), 4.68(br s, 2H), 5.06~5.09(m, 1H), 5.18~5.21(m, 1H), 7.23~7.39(m, 3H), 7.55(dd, J=1.6, J=7.8, 1H)

Example 3

Preparation of 1-(2-chlorophenyl)-1-hydroxypropyl-2-carbamate(3)

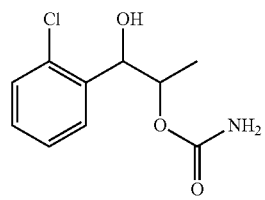

The substantially same method as described in Example 1 was conducted, except that 1-(2-chlorophenyl)-1,2-(Bis-trimethylsilanyloxy) propane (Preparation example 71) was used instead of 1-(2-chlorophenyl)-(S,S)-1,2-(Bis-trimethylsilanyloxy) propane (Preparation example 69) to obtain the title compound (3.8 g, yield 60~90%).

$^1$H NMR(400 MHz, CDCl$_3$) δ1.24(d, J=6.4, 3H), 2.91(d, J=4.8, 1H), 4.68(br s, 2H), 5.06~5.09(m, 1H), 5.18~5.21(m, 1H), 7.23~7.39(m, 3H), 7.55(dd, J=1.6, J=7.8, 1H)

Example 4

Preparation of 1-(2-chlorophenyl)-(S)-1-hydroxypropyl-(R)-2-carbamate(4)

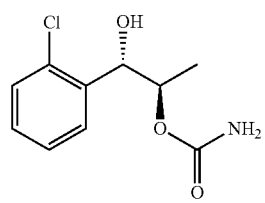

The substantially same method as described in Example 1 was conducted, except that 1-(2-chlorophenyl)-(S,R)-1,2-(Bis-trimethylsilanyloxy) propane (Preparation example 72) was used instead of 1-(2-chlorophenyl)-(S,S)-1,2-(Bis-trimethylsilanyloxy) propane (Preparation example 69) to obtain the title compound (2.4 g, yield 60~90%).

¹H NMR(400 MHz, CDCl₃) δ1.24(d, J=6.4, 3H), 2.91(d, J=4.8, 1H), 4.68(br s, 2H), 5.06~5.09(m, 1H), 5.18~5.21(m, 1H), 7.23~7.39(m, 3H), 7.55(dd, J=1.6, J=7.8, 1H)

Example 5

Preparation of 1-(2-chlorophenyl)-(R)-1-hydroxypropyl-(S)-2-carbamate(5)

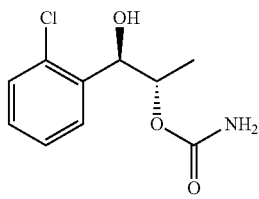

The substantially same method as described in Example 1 was conducted, except that 1-(2-chlorophenyl)-(R,S)-1,2-(Bis-trimethylsilanyloxy) propane (Preparation example 73) was used instead of 1-(2-chlorophenyl)-(S,S)-1,2-(Bis-trimethylsilanyloxy) propane (Preparation example 69) to obtain the title compound (2.3 g, yield 60~90%).

¹H NMR(400 MHz, CDCl₃) δ1.24(d, J=6.4, 3H), 2.91(d, J=4.8, 1H), 4.68(br s, 2H), 5.06~5.09(m, 1H), 5.18~5.21(m, 1H), 7.23~7.39(m, 3H), 7.55(dd, J=1.6, J=7.8, 1H)

Example 6

Preparation of 1-(2-chlorophenyl)-(S)-1-hydroxybutyl-(S)-2-carbamate(6)

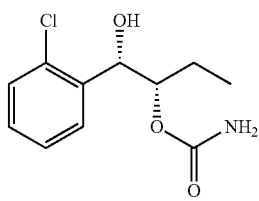 [SMILES: CC[C@H](OC(N)=O)[C@@H](O)c1ccccc1Cl]

The substantially same method as described in Example 1 was conducted, except that 1-(2-chlorophenyl)-(S,S)-1,2-(Bis-trimethylsilanyloxy)butane (Preparation example 74) was used instead of 1-(2-chlorophenyl)-(S,S)-1,2-(Bis-trimethylsilanyloxy) propane (Preparation example 69) to obtain the title compound (2.6 g, yield 60~90%).

¹H NMR(400 MHz, CDCl₃) δ0.96(t, J=7.4 Hz, 3H), 1.57~1.73(m, 2H), 3.01(d, J=5.6 Hz, 1H), 4.74(br s, 2H), 4.95(dt, J=7.2, 8.8 Hz, 1H), 5.23(t, J=5.6 Hz, 1H), 7.22~7.54(m, 4H)

Example 7

Synthesis of 1-(2-chlorophenyl)-(R)-1-hydroxybutyl-(R)-2-carbamate(7)

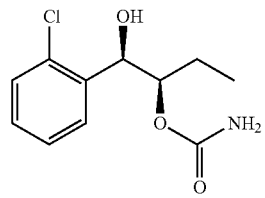 [SMILES: CC[C@@H](OC(N)=O)[C@H](O)c1ccccc1Cl]

The substantially same method as described in Example 1 was conducted, except that 1-(2-chlorophenyl)-(R,R)-1,2-(Bis-trimethylsilanyloxy)butane (Preparation Example 75) was used instead of 1-(2-chlorophenyl)-(S,S)-1,2-(Bis-trimethylsilanyloxy) propane (Preparation example 69) to obtain the title compound (2.5 g, yield 60~90%).

¹H NMR(400 MHz, CDCl₃) δ0.94(t, J=7.4 Hz, 3H), 1.53~1.73(m, 2H), 2.92(s, 1H), 4.78(br s, 2H), 4.91~4.96(m, 1H), 5.22(d, J=5.5 Hz, 1H), 7.20~7.54(m, 4H)

Example 8

Synthesis of 1-(2-chlorophenyl)-1-hydroxybutyl-2-carbamate(8)

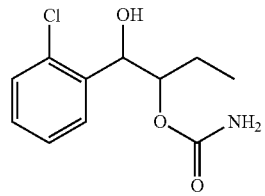 [SMILES: CCC(OC(N)=O)C(O)c1ccccc1Cl]

The substantially same method as described in Example 1 was conducted, except that 1-(2-chlorophenyl)-1,2-(Bis-trimethylsilanyloxy)butane (Preparation Example 76) was used instead of 1-(2-chlorophenyl)-(S,S)-1,2-(Bis-trimethylsilanyloxy) propane (Preparation example 69) to obtain the title compound (1.9 g, yield 60~90%).

¹H NMR(400 MHz, CDCl₃) δ0.97(t, J=7 Hz, 3H), 1.58~1.74(m, 2H), 2.94(d, J=6 Hz, 1H), 4.69(br s, 2H), 4.94~4.99(m, 1H), 5.24(t, J=6 Hz, 1H), 7.23~7.56(m, 4H)

Example 9

Synthesis of 1-(2-chlorophenyl)-(8)-1-hydroxy-3-methyl-butyl-(8)-2-carbamate(9)

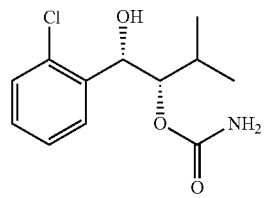 [SMILES: CC(C)[C@H](OC(N)=O)[C@@H](O)c1ccccc1Cl]

The substantially same method as described in Example 1 was conducted, except that 1-(2-chlorophenyl)-3-methyl-(S,S)-1,2-(Bis-trimethylsilanyloxy)butane (Preparation Example 77) was used instead of 1-(2-chlorophenyl)-(S,S)-1,2-(Bis-trimethylsilanyloxy) propane (Preparation example 69) to obtain the title compound (1.7 g, yield 60~90%).

$^1$H NMR(400 MHz, CDCl$_3$) δ1.01(d, J=6.4 Hz, 3H), 1.09(d, J=6.8 Hz, 3H), 2.06(m, 1H), 2.75(d, J=6.8 Hz, 1H), 4.58(br s, 2H), 4.85~4.88(m, 1H), 5.34~5.37(m, 1H), 7.22~7.33(m, 2H), 7.35~7.37(m, 1H), 7.51~7.53(m, 1H)

Example 10

Synthesis of 1-(2-chlorophenyl)-(R)-1-hydroxy-3-methyl-butyl-(R)-2-carbamate(10)

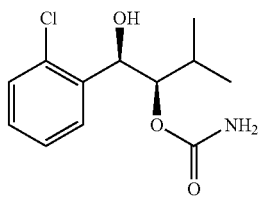 [SMILES: CC(C)[C@@H](OC(N)=O)[C@H](O)c1ccccc1Cl]

The substantially same method as described in Example 1 was conducted, except that 1-(2-chlorophenyl)-3-methyl-(R,R)-1,2-(Bis-trimethylsilanyloxy)butane (Preparation Example 78) was used instead of 1-(2-chlorophenyl)-(S,S)-1,2-(Bis-trimethylsilanyloxy) propane (Preparation example 69) to obtain the title compound (1.6 g, yield 60~90%).

$^1$H NMR(400 MHz, CDCl$_3$) δ1.01(d, J=6.8 Hz, 3H), 1.09(d, J=6.8 Hz, 3H), 2.06(m, 1H), 2.73(d, J=6.8 Hz, 1H), 4.57(br s, 2H), 4.85~4.88(m, 1H), 5.34~5.37(m, 1H), 7.24~7.30(m, 2H), 7.35~7.37(m, 1H), 7.51~7.53(m, 1H)

Example 11

Synthesis of 1-(2-chlorophenyl)-1-hydroxy-3-methyl-butyl-2-carbamate(11)

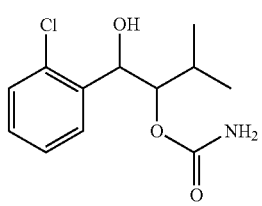 [SMILES: CC(C)C(OC(N)=O)C(O)c1ccccc1Cl]

The substantially same method as described in Example 1 was conducted, except that 1-(2-chlorophenyl)-3-methyl-1,2-(Bis-trimethylsilanyloxy)butane (Preparation Example 79) was used instead of 1-(2-chlorophenyl)-(S,S)-1,2-(Bis-trimethylsilanyloxy) propane (Preparation example 69) to obtain the title compound (1.7 g, yield 60~90%).

$^1$H NMR (400 MHz, CDCl$_3$) δ1.00(d, J=6.4 Hz, 3H), 1.09(d, J=6.4 Hz, 3H), 2.08(m, 1H), 2.76(d, J=6.0 Hz, 1H), 4.59(br s, 2H), 4.87(dd, J=7.2 Hz, 4.4 Hz, 1H), 5.36(t, J=4.6, 1H), 7.23~7.54(m, 4H)

Example 12

Synthesis of 1-(2-chlorophenyl)-(S)-1-hydroxy-hexyl-(S)-2-carbamate(12)

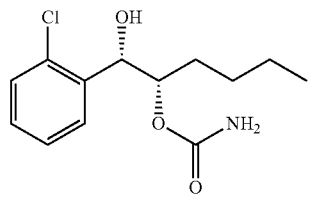 [SMILES: CCCC[C@H](OC(N)=O)[C@@H](O)c1ccccc1Cl]

The substantially same method as described in Example 1 was conducted, except that 1-(2-chlorophenyl)-(S,S)-1,2-(Bis-trimethylsilanyloxy)hexane (Preparation Example 80) was used instead of 1-(2-chlorophenyl)-(S,S)-1,2-(Bis-trimethylsilanyloxy) propane (Preparation example 69) to obtain the title compound (2.3 g, yield 60~90%).

$^1$H NMR (400 MHz, CDCl$_3$) δ0.88(t, J=7 Hz, 3H), 1.33~1.42(m, 4H), 1.53~1.71(m, 2H), 2.89(d, J=5.6 Hz, 1H) 4.64(br s, 2H), 5.04(dt, J=5.0, 9.0 Hz, 1H), J=5.6 Hz, 1H), 7.23~7.55(m, 4H)

Example 13

Synthesis of 1-(2-chlorophenyl)-(R)-1-hydroxy-hexyl-(R)-2-carbamate(13)

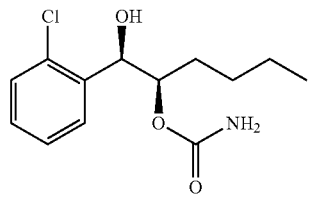 [SMILES: CCCC[C@@H](OC(N)=O)[C@H](O)c1ccccc1Cl]

The substantially same method as described in Example 1 was conducted, except that 1-(2-chlorophenyl)-(R,R)-1,2-(Bis-trimethylsilanyloxy)hexane (Preparation Example 81) was used instead of 1-(2-chlorophenyl)-(S,S)-1,2-(Bis-trimethylsilanyloxy) propane (Preparation example 69) to obtain the title compound (2.2 g, yield 60~90%).

$^1$H NMR(400 MHz, CDCl$_3$) δ 0.89(dd, J=5 Hz, 3H), 1.28~1.43(m, 4H), 1.52~1.58(m, 1H), 1.65~1.72(m, 1H), 2.90(d, J=6 Hz, 1H), 4.64(br s, 2H), 5.01~5.06(m, 1H), 5.22(t, J=6 Hz, 1H), 7.22~7.56(m, 4H)

Example 14

Synthesis of 1-(2-chlorophenyl)-1-hydroxyhexyl-2-carbamate(14)

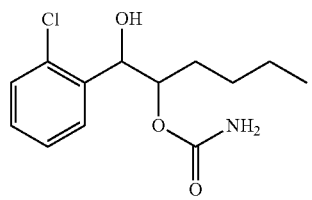 [SMILES: CCCCC(OC(N)=O)C(O)c1ccccc1Cl]

The substantially same method as described in Example 1 was conducted, except that 1-(2-chlorophenyl)-1,2-(Bis-trimethylsilanyloxy)hexane (Preparation Example 82) was used instead of 1-(2-chlorophenyl)-(S,S)-1,2-(Bis-trimethylsilanyloxy) propane (Preparation example 69) to obtain the title compound (2.1 g, yield 60~90%).

$^1$H NMR(400 MHz, CDCl$_3$) δ 0.88(dd, 1=5 Hz, 3H), 1.31~1.43(m, 4H), 1.63~1.70(m, 1H), 1.52~1.60(m, 1H), 3.06(d, J=6 Hz, 1H), 4.75(br s, 2H), 5.00~5.05(m, 1H), 5.21(t, J=6 Hz, 1H), 7.22~7.55(m, 4H)

Example 15

Synthesis of 1-(2-chlorophenyl)-(S)-1-hydroxypropyl-(S)-2-N-methylcarbamate(15)

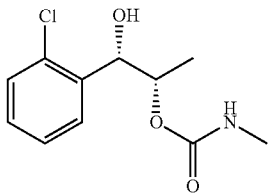 [SMILES: CNC(=O)O[C@@H](C)[C@@H](O)c1ccccc1Cl]

1-(2-chlorophenyl)-(S,S)-1,2-propanediol (2.4 g) obtained in Preparation Example 14, tetrahydrofuran (THF, 12 ml), and carbonyldiimidazole (CDI, 3.12 g) were put into a flask and stirred at the room temperature. After approximately 3 hours, methylamine solution (CH$_3$NH$_2$, 4 ml (33% in EtOH)) was added thereto. When the reaction was completed, the obtained product was washed with 1M HCl solution and ethylacetate (EA). The separated organic layer was dehydrated with anhydrous magnesium sulfate (MgSO$_4$), filtrated, and concented under reduced pressure. The concentrated residue was purified by a silica gel column chromatography, to obtain the title compound (1.6 g, yield 51%).

$^1$H NMR(400 MHz, CDCl$_3$) δ1.03~1.25(m, 3H), 2.76(s, 3H), 3.34(s, 1H), 4.80(br s 1H), 5.04(t, J=12.5 Hz, 1H), 5.14(s, 1H), 7.20~7.53(m, 4H)

Example 16

Synthesis of 1-(2-chlorophenyl)-(S)-1-hydroxypropyl-(S)-2-N-propylcarbamate(16)

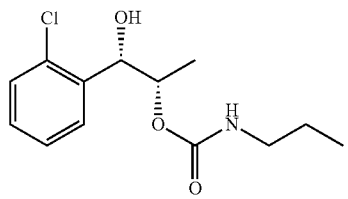 [SMILES: CCCNC(=O)O[C@@H](C)[C@@H](O)c1ccccc1Cl]

The substantially same method as described in Example 15 was conducted, except that propylamine was used instead of methylamine solution (CH$_3$NH$_2$ in EtOH), to obtain the title compound (0.79 g, yield 25%).

$^1$H NMR(400 MHz, CDCl$_3$) δ0.90(t, J=6.8 Hz, 3H), 1.20(d, J=5.96 Hz, 3H), 1.49(dd, J=14.2 Hz, 2H), 3.11(d, J=6.28 Hz, 2H), 3.34(s, 1H), 4.84(br s, 1H), 5.05(t, J=5.88 Hz, 1H), 5.14(s, 1H), 7.22~7.53(m, 4H)

Example 17

Synthesis of 1-(2-chlorophenyl)-(S)-1-hydroxypropyl-(R)-2-N-isopropylcarbamate(17)

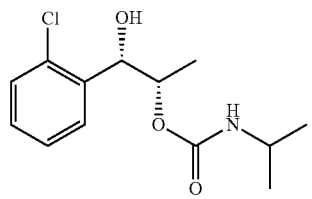 [SMILES: CC(C)NC(=O)O[C@@H](C)[C@@H](O)c1ccccc1Cl]

The substantially same method as described in Example 15 was conducted, except that isopropylamine was used instead of methylamine solution (CH$_3$NH$_2$ in EtOH), to obtain the title compound (1.5 g, yield 41%).

$^1$H NMR(400 MHz, CDCl$_3$) δ1.14(dd, J=6.5 Hz, 6H), 1.19(d, J=6.4 Hz, 3H), 3.21(s, 1H), 3.73~3.82(m, 1H), 4.59(br s, 1H), 5.01~5.07(m, 1H), 5.14(t, J=5.8 Hz, 1H), 7.20~7.53(m, 4H)

Example 18

Synthesis of 1-(2-chlorophenyl)-(S)-1-hydroxypropyl-(R)-2-N-cyclopropylcarbamate(18)

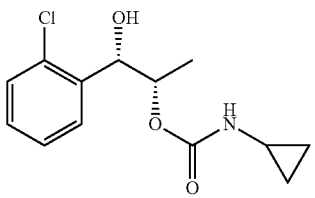 [SMILES: C[C@H](OC(=O)NC1CC1)[C@@H](O)c1ccccc1Cl]

The substantially same method as described in Example 15 was conducted, except that cyclopropylamine was used instead of methylamine solution (CH$_3$NH$_2$ in EtOH), to obtain the title compound (2.2 g, yield 43%).

$^1$H NMR(400 MHz, CDCl$_3$) δ0.50~0.56(m, 2H), 0.74(d, J=7.21 Hz, 2H), 1.25(s, 3H), 2.56~2.61(m, 1H), 3.72(s, 1H), 4.98(br s, 1H), 5.05~5.11(m, 1H), 7.16(s, 1H), 7.23~7.54(m, 4H)

Example 19

Synthesis of 1-(2-chlorophenyl)-(S)-1-hydroxypropyl-(R)-2-N-cyclohexyl carbamate(19)

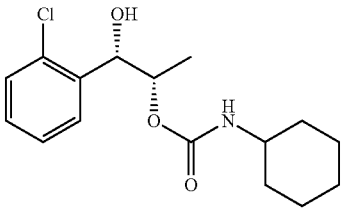 [SMILES: C[C@H](OC(=O)NC1CCCCC1)[C@@H](O)c1ccccc1Cl]

The substantially same method as described in Example 15 was conducted, except that cyclohexylamine was used instead of methylamine solution (CH$_3$NH$_2$ in EtOH), to obtain the title compound (1.1 g, yield 26%).

¹H NMR(400 MHz, CDCl₃) δ1.06~1.40(m, 7H), 1.56~1.61(m, 2H), 1.69~1.71(m, 2H), 1.87~1.94(m, 2H), 3.19(d, J=4.32 Hz, 1H), 3.45(s, 1H), 4.64(br s 1H), 5.02~5.07(m, 1H), 5.14(t, J=6.08 Hz, 1H) 7.20~7.53(m, 4H)

Example 20

Synthesis of 1-(2-chlorophenyl)-(S)-1-hydroxypropyl-(S)-2-N-benzyl carbamate(20)

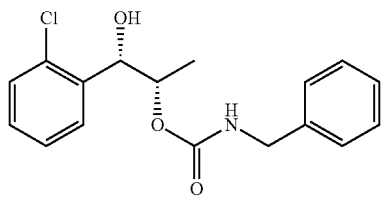 [SMILES: C[C@H](OC(=O)NCc1ccccc1)[C@@H](O)c1ccccc1Cl]

The substantially same method as described in Example 15 was conducted, except that benzylamine was used instead of methylamine solution (CH₃NH₂ in EtOH), to obtain the title compound (1.2 g, yield 18%).
¹H NMR(400 MHz, CDCl₃) δ 1.27(d, J=10 Hz, 3H), 3.12(d, J=5 Hz, 1H), 4.37(d, J=6 Hz, 2H), 5.12~5.19(m, 3H), 7.15~7.56(m, 9H)

Example 21

Synthesis of 1-(2-chlorophenyl)-(S)-1-hydroxypropyl-(S)-2-N-bicyclo[2,2,1]heptanescarbamate(21)

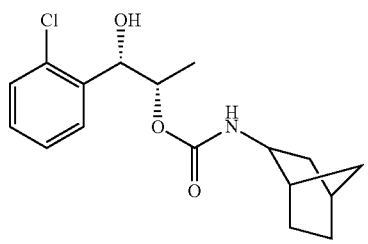 [SMILES: C[C@H](OC(=O)NC1CC2CCC1C2)[C@@H](O)c1ccccc1Cl]

The substantially same method as described in Example 15 was conducted, except that 2-aminonorbornane was used instead of methylamine solution (CH₃NH₂ in EtOH), to obtain the title compound (1.7 g, yield 32%).
¹H NMR(400 MHz, CDCl₃) δ1.08~1.35(m, 9H), 1.65(br s, 1H), 1.75~1.71(m, 1H), 2.14~2.24(m, 1H), 2.27~2.30(m, 1H), 3.23~3.29(m, 1H), 3.47~3.52(m, 1H), 4.67(br s, 1H), 5.01~5.09(m, 1H), 5.12~5.18(m, 1H), 7.22~7.55(m, 4H)

Example 22

Synthesis of 1-(2-chlorophenyl)-(R)-1-hydroxypropyl-(R)-2-N-methylcarbamate(22)

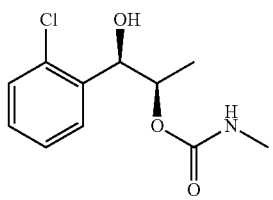 [SMILES: CNC(=O)O[C@H](C)[C@H](O)c1ccccc1Cl]

The substantially same method as described in Example 15 was conducted, except that 1-(2-chlorophenyl)-(R,R)-1,2-propanediol (Preparation example 15) was used instead of 1-(2-chlorophenyl)-(S,S)-1,2-propanediol (Preparation example 14), to obtain the title compound (3.36 g, yield 60%).
¹H NMR(400 MHz, CDCl₃) δ 1.20(d, J=6.8 Hz, 3H), 2.80(d, J=4.8 Hz, 3H), 3.20(d, J=4.4 Hz, 1H), 4.75(br s, 1H), 5.03~5.09(m, 1H), 5.14~5.17(m, 1H), 7.22~7.55(m, 4H)

Example 23

Synthesis of 1-(2-chlorophenyl)-(R)-1-hydroxypropyl-(R)-2-N-propylcarbamate(23)

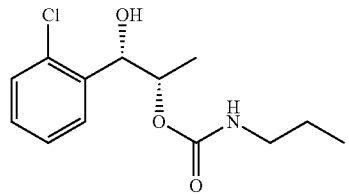 [SMILES: CCCNC(=O)O[C@@H](C)[C@@H](O)c1ccccc1Cl]

The substantially same method as described in Example 22 was conducted, except that propylamine was used instead of methylamine solution (CH₃NH₂ in EtOH), to obtain the title compound (3.1 g, yield 53%).
¹H NMR(400 MHz, CDCl₃) δ0.92(t, J=7.6 Hz, 3H), 1.21(d, J=6.4 Hz, 3H), 1.51(m, 2H), 3.09~3.14(m, 2H), 3.28(d, J=4.4 Hz, 1H), 4.82(br s, 1H), 5.03~5.09(m, 1H), 5.14~5.17(m, 1H), 7.22~7.55(m, 4H)

Example 24

Synthesis of 1-(2-chlorophenyl)-(R)-1-hydroxypropyl-(R)-2-N-isopropylcarbamate(24)

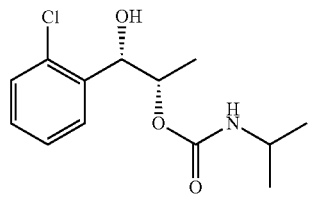 [SMILES: CC(C)NC(=O)O[C@@H](C)[C@@H](O)c1ccccc1Cl]

The substantially same method as described in Example 22 was conducted, except that isopropylamine was used instead of methylamine solution (CH₃NH₂ in EtOH), to obtain the title compound (0.16 g, yield 27%).
¹H NMR(400 MHz, CDCl₃) δ0.88~1.16(m, 6H), 1.19~1.26(m, 3H), 3.34(s, 1H), 3.71~3.78(m, 1H), 4.62(br s, 1H), 5.03(t, J=5.8 Hz, 1H), 5.13(d, J=4.9 Hz, 1H), 7.20~7.53 (m, 4H)

Example 25

Synthesis of 1-(2-chlorophenyl)-(R)-1-hydroxypropyl-(R)-2-N-cyclopropylcarbamate(25)

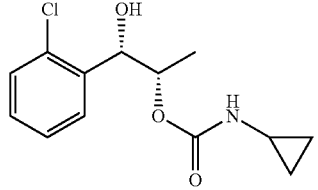 [SMILES: C[C@H](OC(=O)NC1CC1)[C@@H](O)c1ccccc1Cl]

The substantially same method as described in Example 22 was conducted, except that cyclopropylamine was used instead of methylamine solution (CH₃NH₂ in EtOH), to obtain the title compound (3.7 g, yield 60%).

¹H NMR(400 MHz, CDCl₃) δ0.49~0.54(m, 2H), 0.74(d, J=7.2 Hz, 2H), 1.22(s, 3H), 2.55~2.60(m, 1H), 3.16(s, 1H), 5.00(s, 1H), 5.04~5.11(m, 1H), 5.16(s, 1H), 7.23~7.54(m, 4H)

Example 26

Synthesis of 1-(2-chlorophenyl)-(R)-1-hydroxypropyl-(R)-2-N-cyclohexyl carbamate(26)

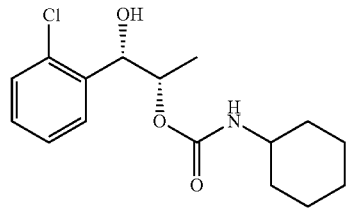 [SMILES: C[C@H](OC(=O)NC1CCCCC1)[C@@H](O)c1ccccc1Cl]

The substantially same method as described in Example 22 was conducted, except that cyclohexylamine was used instead of methylamine solution (CH₃NH₂ in EtOH), to obtain the title compound (1.9 g, yield 28%).

¹H NMR(400 MHz, CDCl₃) δ1.05~1.38(m, 8H), 1.58~1.70(m, 3H), 1.85~1.95(m, 2H), 3.39~3.47(m, 1H), 3.56(s, 1H), 4.79(br s, 1H), 5.01~5.07(m, 1H), 5.14(t, J=5.2 Hz, 1H), 7.20~7.54(m, 4H)

Example 27

Synthesis of 1-(2-chlorophenyl)-(R)-1-hydroxypropyl-(R)-2-N-benzylcarbamate(27)

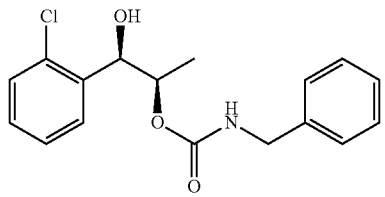 [SMILES: C[C@@H](OC(=O)NCc1ccccc1)[C@H](O)c1ccccc1Cl]

The substantially same method as described in Example 22 was conducted, except that benzylamine was used instead of methylamine solution (CH₃NH₂ in EtOH), to obtain the title compound (0.52 g, yield 19%).

¹H NMR(400 MHz, CDCl₃) δ1.25(d, J=6 Hz, 3H), 1.64(s, 1H), 3.13(d, J=4.4 Hz, 1H), 4.37(d, J=5.6 Hz, 2H), 5.12~5.19(m, 2H), 7.23~7.55(m, 9H)

Example 28

Synthesis of 1-(2-chlorophenyl)-(R)-1-hydroxypropyl-(R)-2-N-bicyclo[2,2,1]heptanecarbamate(28)

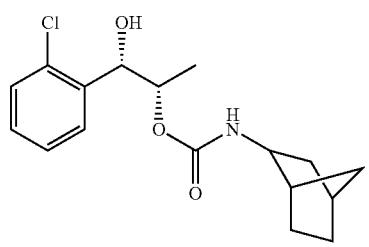 [SMILES: C[C@H](OC(=O)NC1CC2CCC1C2)[C@@H](O)c1ccccc1Cl]

The substantially same method as described in Example 22 was conducted, except that 2-aminonorbornane was used instead of methylamine solution (CH₃NH₂ in EtOH), to obtain the title compound (1.7 g, yield 20~50%).

¹H NMR(400 MHz, CDCl₃) δ1.08~1.35(m, 9H), 1.65(br s, 1H), 1.75~1.71(m, 1H), 2.14~2.24(m, 1H), 2.27~2.30(m, 1H), 3.23~3.29(m, 1H), 3.47~3.52(m, 1H), 4.67(br s, 1H), 5.01~5.09(m, 1H), 5.12~5.18(m, 1H), 7.22~7.55(m, 4H)

Example 29

Synthesis of 1-(2-chlorophenyl)-1-hydroxypropyl-2-N-methylcarbamate(29)

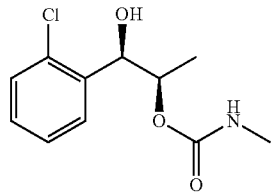 [SMILES: CNC(=O)O[C@H](C)[C@H](O)c1ccccc1Cl]

The substantially same method as described in Example 15 was conducted, except that 1-(2-chlorophenyl)-1,2-propanediol (Preparation example 16) was used instead of 1-(2-chlorophenyl)-(S,S)-1,2-propanediol (Preparation example 14), to obtain the title compound (2.6 g, yield 45%).

¹H NMR(400 MHz, CDCl₃) δ 1.21(d, J=6 Hz, 3H), 2.81(d, J=5 Hz, 3H), 3.14(d, J=4 Hz, 1H), 4.72(br s, 1H), 5.07(dd, J=6 Hz, 1H), 5.16(t, J=6 Hz, 1H), 7.22~7.56(m, 4H)

Example 30

Synthesis of 1-(2-chlorophenyl)-1-hydroxypropyl-2-N-propylcarbamate(30)

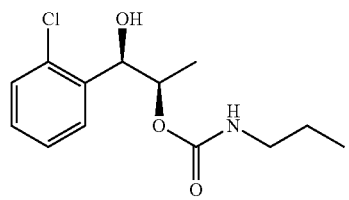 [SMILES: CCCNC(=O)O[C@H](C)[C@H](O)c1ccccc1Cl]

The substantially same method as described in Example 29 was conducted, except that propylamine was used instead of methylamine solution (CH₃NH₂ in EtOH), to obtain the title compound (1.0 g, yield 17%).

¹H NMR(400 MHz, CDCl₃) δ 0.92(t, J=7 Hz, 3H), 1.21(d, J=6 Hz, 3H), 1.53(dd, J=7 Hz, 2H), 3.13(dd, J=7 Hz, 2H), 3.28(d, 1H), 4.82(S, 1H), 5.06(dd, J=7 Hz, 1H), 5.16(t, J=5 Hz, 1H), 7.21~7.56(m, 4H)

Example 31

Synthesis of 1-(2-chlorophenyl)-1-hydroxypropyl-2-N-isopropylcarbamate(31)

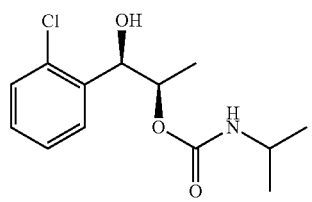 [SMILES: CC(C)NC(=O)O[C@H](C)[C@H](O)c1ccccc1Cl]

The substantially same method as described in Example 29 was conducted, except that isopropylamine was used instead of methylamine solution (CH₃NH₂ in EtOH), to obtain the title compound (0.54 g, yield 16%).

¹H NMR(400 MHz, CDCl₃) δ 1.16(dd, J=6 Hz, 6H), 1.21(d, J=6 Hz, 3H), 3.23(d, J=6 Hz, 1H), 3.75~3.84(m, 1H), 4.61(br s, 1H), 5.06(t, J=6 Hz, 1H), 5.16(t, J=6 Hz, 1H), 7.22~7.56(m, 4H)

Example 32

Synthesis of 1-(2-chlorophenyl)-1-hydroxypropyl-2-N-cyclopropylcarbamate(32)

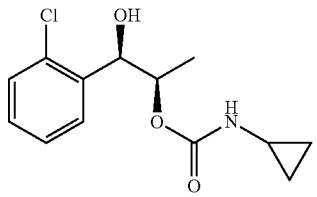 [SMILES: C[C@@H](OC(=O)NC1CC1)[C@H](O)c1ccccc1Cl]

The substantially same method as described in Example 29 was conducted, except that cyclopropylamine was used instead of methylamine solution (CH₃NH₂ in EtOH), to obtain the title compound (1.0 g, yield 17%).

¹H NMR(400 MHz, CDCl₃) δ 0.50(t, J=6 Hz, 2H), 0.77(t, J=3 Hz, 2H), 1.12(d, J=7 Hz, 3H), 2.53~2.59(m, 1H), 3.22(d, J=4 Hz, 1H), 5.08(dd, J=6 Hz, 1H), 5.15(S, 1H), 7.22~7.55(m, 4H)

Example 33

Synthesis of 1-(2-chlorophenyl)-1-hydroxypropyl-2-N-cyclohexylcarbamate(33)

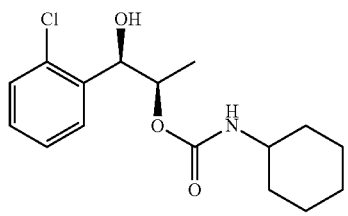 [SMILES: C[C@@H](OC(=O)NC1CCCCC1)[C@H](O)c1ccccc1Cl]

The substantially same method as described in Example 29 was conducted, except that cyclohexylamine was used instead of methylamine solution (CH₃NH₂ in EtOH), to obtain the title compound (2.2 g, yield 33%).

¹H NMR(400 MHz, CDCl₃) δ 1.07~1.17(m, 3H), 1.21(d, J=6 Hz, 3H), 1.29~1.42(m, 3H), 1.72(dd, J=6 Hz, 2H), 1.92(dd, J=6 Hz, 2H), 3.26(d, J=4 Hz, 1H), 3.46(t, J=4 Hz, 1H), 4.68(d, J=6 Hz, 1H), 5.07(dd, J=6 Hz, 1H), 5.16(t, J=6 Hz, 1H), 7.22~7.55(m, 4H)

Example 34

Synthesis of 1-(2-chlorophenyl)-1-hydroxypropyl-2-N-benzylcarbamate(34)

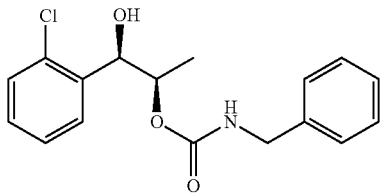 [SMILES: C[C@@H](OC(=O)NCc1ccccc1)[C@H](O)c1ccccc1Cl]

The substantially same method as described in Example 29 was conducted, except that benzylamine was used instead of methylamine solution (CH₃NH₂ in EtOH), to obtain the title compound (1.3 g, yield 19%).

¹H NMR(400 MHz, CDCl₃) δ 1.25(d, J=6 Hz, 3H), 3.16(d, J=4 Hz, 1H), 4.36(d, J=6 Hz, 2H), 5.14(dd, J=6 Hz, 3H), 7.23~7.56(m, 9H), yield: 19% (1.3 g)

Example 35

Synthesis of 1-(2-chlorophenyl)-1-hydroxypropyl-2-N-bicyclo[2,2,1]heptanecarbamate(35)

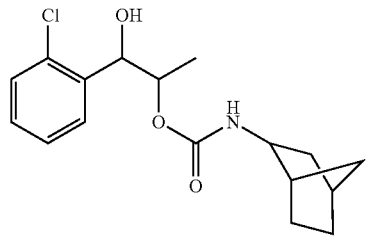 [SMILES: CC(OC(=O)NC1CC2CCC1C2)C(O)c1ccccc1Cl]

The substantially same method as described in Example 29 was conducted, except that 2-aminonorbornane was used instead of methylamine solution (CH₃NH₂ in EtOH), to obtain the title compound (1.7 g, yield 20~50%).

¹H NMR(400 MHz, CDCl₃) δ1.08~1.35(m, 9H), 1.65(br s, 1H), 1.75~1.71(m, 1H), 2.14~2.24(m, 1H), 2.27~2.30(m, 1H), 3.23~3.29(m, 1H), 3.47~3.52(m, 1H), 4.67(br s, 1H), 5.01~5.09(m, 1H), 5.12~5.18(m, 1H), 7.22~7.55(m, 4H)

Example 36

Synthesis of 1-(2,4-dichlorophenyl)-(S)-1-hydroxypropyl-(S)-2-carbamate(36)

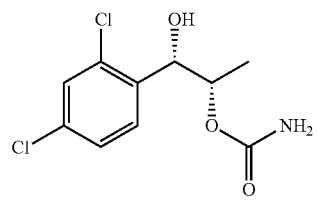 [SMILES: C[C@H](OC(N)=O)[C@@H](O)c1ccc(Cl)cc1Cl]

The substantially same method as described in Example 1 was conducted, except that 1-(2,4-dichlorophenyl)-(S,S)-1,2-(Bis-trimethylsilanyloxy)propane (Preparation Example 83) was used instead of 1-(2-chlorophenyl)-(S,S)-1,2-(Bis-trimethylsilanyloxy) propane (Preparation example 69) to obtain the title compound (1.8 g, yield 60~90%).

¹H NMR(400 MHz, CDCl₃) δ1.22(d, J=6.4 Hz, 3H), 4.16(br t, 1H) 4.96(br t, 3H), 5.07(t, J=4.8 Hz, 1H), 7.23~7.52(m, 3H)

Example 37

Synthesis of 1-(2,6-dichlorophenyl)-(S)-1-hydroxy-propyl-(S)-2-carbamate(37)

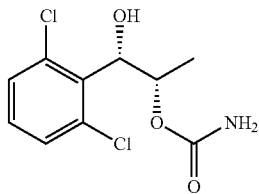 [SMILES: C[C@H](OC(N)=O)[C@@H](O)c1c(Cl)cccc1Cl]

The substantially same method as described in Example 1 was conducted, except that 1-(2,6-dichlorophenyl)-(S,S)-1,2-(Bis-trimethylsilanyloxy)propane (Preparation Example 84) was used instead of 1-(2-chlorophenyl)-(S,S)-1,2-(Bis-trimethylsilanyloxy) propane (Preparation example 69) to obtain the title compound (2.6 g, yield 60~90%)

Example 38

Synthesis of 1-(2,3-dichlorophenyl)-(S)-1-hydroxy-propyl-(S)-2-carbamate(38)

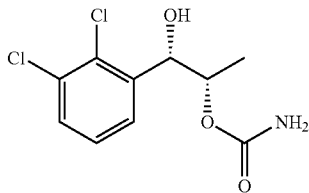 [SMILES: C[C@H](OC(N)=O)[C@@H](O)c1cccc(Cl)c1Cl]

The substantially same method as described in Example 1 was conducted, except that 1-(2,3-dichlorophenyl)-(S,S)-1,2-(Bis-trimethylsilanyloxy)propane (Preparation Example 85) was used instead of 1-(2-chlorophenyl)-(S,S)-1,2-(Bis-trimethylsilanyloxy) propane (Preparation example 69) to obtain the title compound (1.4 g, yield 60~90%)

¹H NMR(400 MHz, CDCl₃) δ1.15(d, J=6.4 Hz, 3H), 3.66(d, J=9.2 Hz, 1H), 4.73(br s, 2H), 5.43(t, J=9.0 Hz, 1H), 5.62~5.69(m, 1H), 7.18~7.22(m, 3H),

Example 39

Synthesis of 1-(2,4-dichlorophenyl)-(S)-1-hydroxy-butyl-(S)-2-carbamate(39)

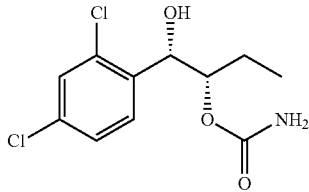 [SMILES: CC[C@H](OC(N)=O)[C@@H](O)c1ccc(Cl)cc1Cl]

The substantially same method as described in Example 1 was conducted, except that 1-(2,4-dichlorophenyl)-(S,S)-1,2-(Bis-trimethylsilanyloxy)butane (Preparation Example 86) was used instead of 1-(2-chlorophenyl)-(S,S)-1,2-(Bis-trimethylsilanyloxy) propane (Preparation example 69) to obtain the title compound (2.3 g, yield 60~90%).

¹H NMR(400 MHz, CDCl₃) δ0.96(t, J=7.4 Hz, 3H), 1.58~1.74(m, 2H), 2.98(d, J=5.6 Hz, 1H) 4.68(br s, 2H), 5.59(dt, J=5.2, 8.8 Hz, 1H), 5.19(t, J=5.4 Hz, 1H), 7.30~7.50 (m, 3H)

Example 40

Synthesis of 1-(2,6-dichlorophenyl)-(S)-1-hydroxy-butyl-(S)-2-carbamate(40)

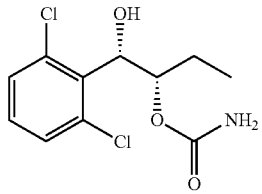 [SMILES: CC[C@H](OC(N)=O)[C@@H](O)c1c(Cl)cccc1Cl]

The substantially same method as described in Example 1 was conducted, except that 1-(2,6-dichlorophenyl)-(S,S)-1,2-(Bis-trimethylsilanyloxy)butane (Preparation Example 87) was used instead of 1-(2-chlorophenyl)-(S,S)-1,2-(Bis-trimethylsilanyloxy) propane (Preparation example 69) to obtain the title compound (1.7 g, yield 60~90%).

¹H NMR(400 MHz, CDCl₃) δ0.92(t, J=7.4 Hz, 3H), 1.30~1.38(m, 1H), 1.57~1.64(m, 1H), 3.74(d, J=9.2 Hz, 1H), 4.80(br s, 2H), 5.40~5.50(m, 2H), 7.17~7.34(m, 3H)

Example 41

Synthesis of 1-(2,4-dichlorophenyl)-(S)-1-hydroxy-3-methyl-butyl-(S)-2-carbamate(41)

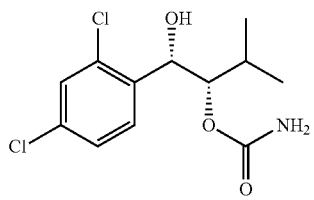

The substantially same method as described in Example 1 was conducted, except that 1-(2,4-dichlorophenyl)-3-methyl-(S,S)-1,2-(Bis-trimethylsilanyloxy)butane (Preparation Example 88) was used instead of 1-(2-chlorophenyl)-(S,S)-1,2-(Bis-trimethylsilanyloxy) propane (Preparation example 69) to obtain the title compound (1.9 g, yield 60~90%).

¹H NMR(400 MHz, CDCl₃) δ1.00(t, J=7.2 Hz, 6H), 1.73~1.79(m, 1H), 3.67~3.69(m, 1H), 4.85(br s, 2H), 5.40~5.43(m, 1H), 5.49~5.54(m, 1H), 7.30~7.50(m, 3H)

Example 42

Synthesis of 1-(2,6-dichlorophenyl)-(S)-1-hydroxy-3-methyl-butyl-(S)-2-carbamate(42)

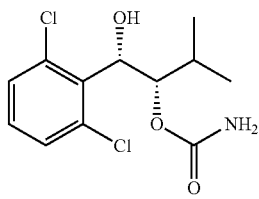 [SMILES: CC(C)[C@H](OC(N)=O)[C@@H](O)c1c(Cl)cccc1Cl]

The substantially same method as described in Example 1 was conducted, except that 1-(2,6-dichlorophenyl)-3-methyl-(S,S)-1,2-(Bis-trimethylsilanyloxy)butane (Preparation Example 89) was used instead of 1-(2-chlorophenyl)-(S,S)-1,2-(Bis-trimethylsilanyloxy) propane (Preparation example 69) to obtain the title compound (2.4 g, yield 60~90%).

$^1$H NMR(400 MHz, CDCl$_3$) δ1.00(t, J=7.2 Hz, 6H), 1.73~1.79(m, 1H), 3.67~3.69(m, 1H), 4.85(br s, 2H), 5.40~5.43(m, 1H), 5.49~5.54(m, 1H), 7.16~7.33(m, 3H)

Example 43

Synthesis of 1-(2,4-dichlorophenyl)-(S)-1-hydroxy-hexyl-(S)-2-carbamate(43)

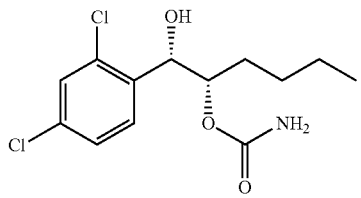 [SMILES: CCCC[C@H](OC(N)=O)[C@@H](O)c1ccc(Cl)cc1Cl]

The substantially same method as described in Example 1 was conducted, except that 1-(2,4-dichlorophenyl)-(S,S)-1,2-(Bis-trimethylsilanyloxy)hexane (Preparation Example 90) was used instead of 1-(2-chlorophenyl)-(S,S)-1,2-(Bis-trimethylsilanyloxy) propane (Preparation example 69) to obtain the title compound (2.2 g, yield 60~90%).

$^1$H NMR(400 MHz, CDCl$_3$) δ0.89(t, J=3.6 Hz, 3H), 1.28~1.42(m, 4H), 1.52~1.59(m, 1H), 1.64~1.71(m, 1H), 2.98(d, J=5.6 Hz, 1H), 4.67(br s, 2H), 4.96~5.00(m, 1H), 5.17(t, J=5.6 Hz, 1H), 7.30~7.49(m 3H)

Example 44

Synthesis of 1-(2,6-dichlorophenyl)-(S)-1-hydroxy-hexyl-(S)-2-carbamate(44)

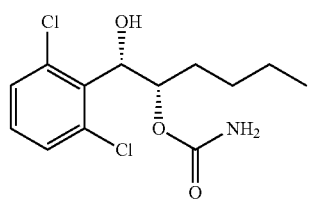 [SMILES: CCCC[C@H](OC(N)=O)[C@@H](O)c1c(Cl)cccc1Cl]

The substantially same method as described in Example 1 was conducted, except that 1-(2,6-dichlorophenyl)-(S,S)-1,2-(Bis-trimethylsilanyloxy)hexane (Preparation Example 91) was used instead of 1-(2-chlorophenyl)-(S,S)-1,2-(Bis-trimethylsilanyloxy) propane (Preparation example 69) to obtain the title compound (2.1 g, yield 60~90%)

$^1$H NMR(400 MHz, CDCl$_3$) δ0.84(t, J=7.0 Hz, 3H), 1.20~1.35(m, 4H), 1.36~1.41(m, 1H), 1.59~1.63(m, 1H), 3.71(d, J=10.0 Hz, 1H), 4.74(br s, 2H), 5.40~5.44(m, 1H), 5.52~5.57(m, 1H), 7.17~7.35(m, 3H)

Example 45

Synthesis of 1-(2,4-dichlorophenyl)-(R)-1-hydroxy-propyl-(R)-2-carbamate(45)

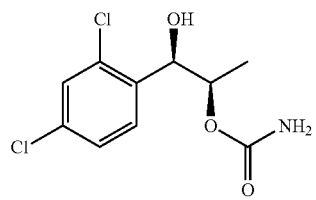 [SMILES: C[C@@H](OC(N)=O)[C@H](O)c1ccc(Cl)cc1Cl]

The substantially same method as described in Example 1 was conducted, except that 1-(2,4-dichlorophenyl)-(R,R)-1,2-(Bis-trimethylsilanyloxy)propane (Preparation Example 92) was used instead of 1-(2-chlorophenyl)-(S,S)-1,2-(Bis-trimethylsilanyloxy) propane (Preparation example 69) to obtain the title compound (1.2 g, yield 60~90%), $^1$H NMR(400 MHz, CDCl$_3$) δ1.22(d, J=6.4 Hz, 3H), 4.16(br t, 1H), 4.96(br t, 3H), 5.07(t, J=4.8 Hz, 1H), 7.23~7.52(m, 3H)

Example 46

Synthesis of 1-(2,6-dichlorophenyl)-(R)-1-hydroxy-propyl-(R)-2-carbamate(46)

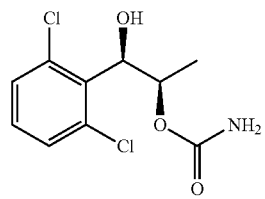 [SMILES: C[C@@H](OC(N)=O)[C@H](O)c1c(Cl)cccc1Cl]

The substantially same method as described in Example 1 was conducted, except that 1-(2,6-dichlorophenyl)-(R,R)-1,2-(Bis-trimethylsilanyloxy)propane (Preparation Example 93) was used instead of 1-(2-chlorophenyl)-(S,S)-1,2-(Bis-trimethylsilanyloxy) propane (Preparation example 69) to obtain the title compound (1.7 g, yield 60~90%), $^1$H NMR(400 MHz, CDCl$_3$) δ1.15(d, J=6.4 Hz, 3H), 3.66(d, J=9.2 Hz, 1H), 4.73(br s, 2H), 5.43(t, J=9.0 Hz, 1H), 5.62~5.69(m, 1H), 7.18~7.22(m, 3H),

Example 47

Synthesis of 1-(2,3-dichlorophenyl)-(R)-1-hydroxy-propyl-(R)-2-carbamate(47)

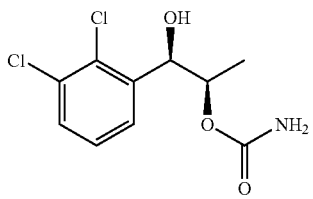 [SMILES: C[C@@H](OC(N)=O)[C@H](O)c1cccc(Cl)c1Cl]

The substantially same method as described in Example 1 was conducted, except that 1-(2,3-dichlorophenyl)-(R,R)-1,2-(Bis-trimethylsilanyloxy)propane (Preparation Example 94) was used instead of 1-(2-chlorophenyl)-(S,S)-1,2-(Bis-trimethylsilanyloxy) propane (Preparation example 69) to obtain the title compound (2.0 g, yield 60~90%)

$^1$H NMR(400 MHz, CDCl$_3$) δ1.15(d, J=6.4 Hz, 3H), 3.66(d, J=9.2 Hz, 1H), 4.73(br s, 2H), 5.43(t, J=9.0 Hz, 1H), 5.62~5.69(m, 1H), 7.18~7.22(m, 3H),

Example 48

Synthesis of 1-(2,4-dichlorophenyl)-(R)-1-hydroxy-butyl-(R)-2-carbamate(48)

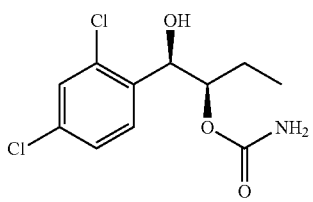 [SMILES: CC[C@@H](OC(N)=O)[C@H](O)c1ccc(Cl)cc1Cl]

The substantially same method as described in Example 1 was conducted, except that 1-(2,4-dichlorophenyl)-(R,R)-1,2-(Bis-trimethylsilanyloxy)butane (Preparation Example 95) was used instead of 1-(2-chlorophenyl)-(S,S)-1,2-(Bis-trimethylsilanyloxy) propane (Preparation example 69) to obtain the title compound (2.3 g, yield 60~90%).

$^1$H NMR(400 MHz, CDCl$_3$) δ0.96(t, J=7.4 Hz, 3H), 1.58~1.74(m, 2H), 2.98(d, J=5.6 Hz, 1H) 4.68(br s, 2H), 5.59(dt, J=5.2, 8.8 Hz, 1H), 5.19(t, J=5.4 Hz, 1H), 7.30~7.50 (m, 3H)

Example 49

Synthesis of 1-(2,6-dichlorophenyl)-(R)-1-hydroxy-butyl-(R)-2-carbamate(49)

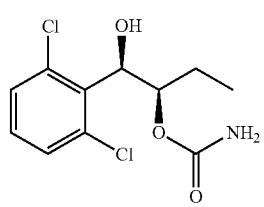 [SMILES: CC[C@@H](OC(N)=O)[C@H](O)c1c(Cl)cccc1Cl]

The substantially same method as described in Example 1 was conducted, except that 1-(2,6-dichlorophenyl)-(R,R)-1,2-(Bis-trimethylsilanyloxy)butane (Preparation Example 96) was used instead of 1-(2-chlorophenyl)-(S,S)-1,2-(Bis-trimethylsilanyloxy) propane (Preparation example 69) to obtain the title compound (2.5 g, yield 60~90%).

$^1$H NMR(400 MHz, CDCl$_3$) δ0.92(t, J=7.4 Hz, 3H), 1.30~1.38(m, 1H), 1.57~1.64(m, 1H), 3.74(d, J=9.2 Hz, 1H), 4.80(br s, 2H), 5.40~5.50(m, 2H), 7.17~7.34(m, 3H)

Example 50

Synthesis of 1-(2,4-dichlorophenyl)-(R)-1-hydroxy-3-methyl-butyl-(R)-2-carbamate(50)

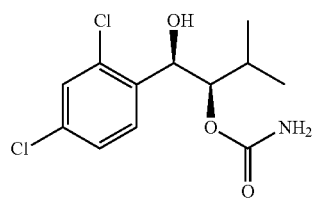 [SMILES: CC(C)[C@@H](OC(N)=O)[C@H](O)c1ccc(Cl)cc1Cl]

The substantially same method as described in Example 1 was conducted, except that 1-(2,4-dichlorophenyl)-3-methyl-(R,R)-1,2-(Bis-trimethylsilanyloxy)butane (Preparation Example 97) was used instead of 1-(2-chlorophenyl)-(S,S)-1,2-(Bis-trimethylsilanyloxy) propane (Preparation example 69) to obtain the title compound (2.8 g, yield 60~90%).

$^1$H NMR(400 MHz, CDCl$_3$) δ1.00(t, J=7.2 Hz, 6H), 1.73~1.79(m, 1H), 3.67~3.69(m, 1H), 4.85(br s, 2H), 5.40~5.43(m, 1H), 5.49~5.54(m, 1H), 7.30~7.50(m, 3H)

Example 51

Synthesis of 1-(2,6-dichlorophenyl)-(R)-1-hydroxy-3-methyl-butyl-(R)-2-carbamate(51)

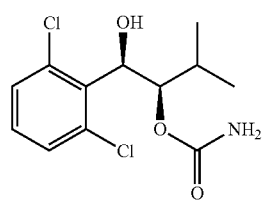 [SMILES: CC(C)[C@@H](OC(N)=O)[C@H](O)c1c(Cl)cccc1Cl]

The substantially same method as described in Example 1 was conducted, except that 1-(2,6-dichlorophenyl)-3-methyl-(R,R)-1,2-(Bis-trimethylsilanyloxy)butane (Preparation Example 98) was used instead of 1-(2-chlorophenyl)-(S,S)-1,2-(Bis-trimethylsilanyloxy) propane (Preparation example 69) to obtain the title compound (2.6 g, yield 60~90%).

$^1$H NMR(400 MHz, CDCl$_3$) δ1.00(t, J=7.2 Hz, 6H), 1.73~1.79(m, 1H), 3.67~3.69(m, 1H), 4.85(br s, 2H), 5.40~5.43(m, 1H), 5.49~5.54(m, 1H), 7.16~7.33(m, 3H)

Example 52

Synthesis of 1-(2,4-dichlorophenyl)-(R)-1-hydroxy-hexyl-(R)-2-carbamate(52)

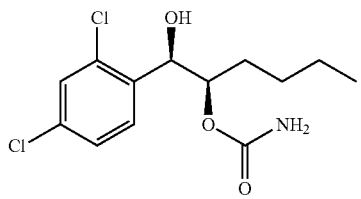 [SMILES: CCCC[C@@H](OC(N)=O)[C@H](O)c1ccc(Cl)cc1Cl]

The substantially same method as described in Example 1 was conducted, except that 1-(2,4-dichlorophenyl)-(R,R)-1,2-(Bis-trimethylsilanyloxy)hexane (Preparation Example 99) was used instead of 1-(2-chlorophenyl)-(S,S)-1,2-(Bis-trimethylsilanyloxy) propane (Preparation example 69) to obtain the title compound (2.5 g, yield 60~90%).

$^1$H NMR(400 MHz, CDCl$_3$) δ0.89(t, J=3.6 Hz, 3H), 1.28~1.42(m, 4H), 1.52~1.59(m, 1H), 1.64~1.71(m, 1H), 2.98(d, J=5.6 Hz, 1H), 4.67(br s, 2H), 4.96~5.00(m, 1H), 5.17(t, J=5.6 Hz, 1H), 7.30~7.49(m, 3H)

Example 53

Synthesis of 1-(2,6-dichlorophenyl)-(R)-1-hydroxy-hexyl-(R)-2-carbamate(53)

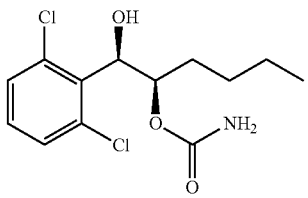 [SMILES: CCCC[C@@H](OC(N)=O)[C@H](O)c1c(Cl)cccc1Cl]

The substantially same method as described in Example 1 was conducted, except that 1-(2,6-dichlorophenyl)-(R,R)-1,2-(Bis-trimethylsilanyloxy)hexane (Preparation Example 100) was used instead of 1-(2-chlorophenyl)-(S,S)-1,2-(Bis-trimethylsilanyloxy) propane (Preparation example 69) to obtain the title compound (2.4 g, yield 60~90%).

$^1$H NMR(400 MHz, CDCl$_3$) δ0.84(t, J=7.0 Hz, 3H), 1.20~1.35(m, 4H), 1.36~1.41(m, 1H), 1.59~1.63(m, 1H), 3.71(d, J=10.0 Hz, 1H), 4.74(br s, 2H), 5.40~5.44(m, 1H), 5.52~5.57(m, 1H), 7.17~7.35(m, 3H)

Example 54

Synthesis of 1-(2,4-dichlorophenyl)-1-hydroxypro-pyl-2-carbamate(54)

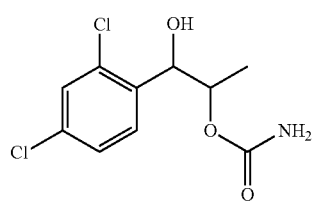 [SMILES: CC(OC(N)=O)C(O)c1ccc(Cl)cc1Cl]

The substantially same method as described in Example 1 was conducted, except that 1-(2,4-dichlorophenyl)-1,2-(Bis-trimethylsilanyloxy)propane (Preparation Example 101) was used instead of 1-(2-chlorophenyl)-(S,S)-1,2-(Bis-trimethylsilanyloxy) propane (Preparation example 69) to obtain the title compound (1.7 g, yield 60~90%).

$^1$H NMR(400 MHz, CDCl$_3$) δ1.22(d, J=6.4 Hz, 3H), 4.16(br t, 1H) 4.96(br t, 3H), 5.07(t, J=4.8 Hz, 1H), 7.23~7.52(m, 3H)

Example 55

Synthesis of 1-(2,6-dichlorophenyl)-1-hydroxypro-pyl-2-carbamate(55)

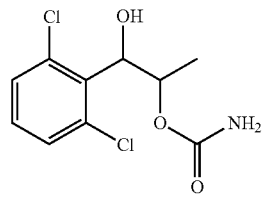 [SMILES: CC(OC(N)=O)C(O)c1c(Cl)cccc1Cl]

The substantially same method as described in Example 1 was conducted, except that 1-(2,6-dichlorophenyl)-1,2-(Bis-trimethylsilanyloxy)propane (Preparation Example 102) was used instead of 1-(2-chlorophenyl)-(S,S)-1,2-(Bis-trimethylsilanyloxy) propane (Preparation example 69) to obtain the title compound (2.4 g, yield 60~90%).

$^1$H NMR(400 MHz, CDCl$_3$) δ1.15(d, J=6.4 Hz, 3H), 3.66(d, J=9.2 Hz, 1H), 4.73(br s, 2H), 5.43(t, J=9.0 Hz, 1H), 5.62~5.69(m, 1H), 7.18~7.22(m, 3H),

Example 56

Synthesis of 1-(2,3-dichlorophenyl)-1-hydroxypro-pyl-2-carbamate(56)

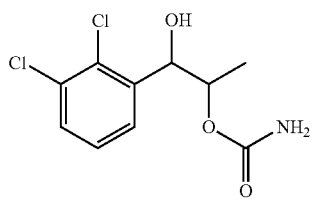 [SMILES: CC(OC(N)=O)C(O)c1cccc(Cl)c1Cl]

The substantially same method as described in Example 1 was conducted, except that 1-(2,3-dichlorophenyl)-1,2-(Bis-trimethylsilanyloxy)propane (Preparation Example 103) was used instead of 1-(2-chlorophenyl)-(S,S)-1,2-(Bis-trimethylsilanyloxy) propane (Preparation example 69) to obtain the title compound (1.6 g, yield 60~90%).

$^1$H NMR(400 MHz, CDCl$_3$) δ1.15(d, J=6.4 Hz, 3H), 3.66(d, J=9.2 Hz, 1H), 4.73(br s, 2H), 5.43(t, J=9.0 Hz, 1H), 5.62~5.69(m, 1H), 7.18~7.22(m, 3H),

Example 57

Synthesis of 1-(2,4-dichlorophenyl)-1-hydroxybutyl-2-carbamate(57)

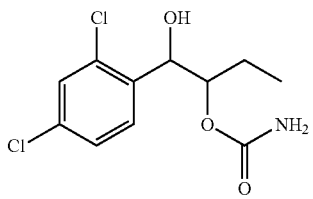 [SMILES: CCC(OC(N)=O)C(O)c1ccc(Cl)cc1Cl]

The substantially same method as described in Example 1 was conducted, except that 1-(2,4-dichlorophenyl)-1,2-(Bis-trimethylsilanyloxy)butane (Preparation Example 104) was used instead of 1-(2-chlorophenyl)-(S,S)-1,2-(Bis-trimethylsilanyloxy) propane (Preparation example 69) to obtain the title compound (1.7 g, yield 60~90%).

$^1$H NMR(400 MHz, CDCl$_3$) δ0.96(t, J=7.4 Hz, 3H), 1.58~1.74(m, 2H), 2.98(d, J=5.6 Hz, 1H) 4.68(br s, 2H), 5.59(dt, J=5.2, 8.8 Hz, 1H), 5.19(t, J=5.4 Hz, 1H), 7.30~7.50 (m, 3H)

Example 58

Synthesis of 1-(2,6-dichlorophenyl)-1-hydroxybutyl-2-carbamate(58)

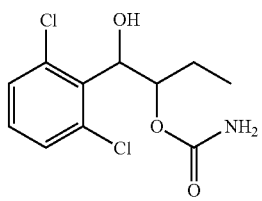 [SMILES: CCC(OC(N)=O)C(O)c1c(Cl)cccc1Cl]

The substantially same method as described in Example 1 was conducted, except that 1-(2,6-dichlorophenyl)-1,2-(Bis-trimethylsilanyloxy)butane (Preparation Example 105) was used instead of 1-(2-chlorophenyl)-(S,S)-1,2-(Bis-trimethylsilanyloxy) propane (Preparation example 69) to obtain the title compound (2.4 g, yield 60~90%).

$^1$H NMR(400 MHz, CDCl$_3$) δ0.92(t, J=7.4 Hz, 3H), 1.30~1.38(m, 1H), 1.57~1.64(m, 1H), 3.74(d, J=9.2 Hz, 1H), 4.80(br s, 2H), 5.40~5.50(m, 2H), 7.17~7.34(m, 3H)

Example 59

Synthesis of 1-(2,4-dichlorophenyl)-1-hydroxy-3-methyl-butyl-2-carbamate(59)

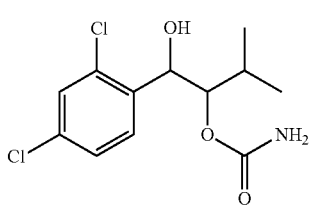 [SMILES: CC(C)C(OC(N)=O)C(O)c1ccc(Cl)cc1Cl]

The substantially same method as described in Example 1 was conducted, except that 1-(2,4-dichlorophenyl)-3-methyl-1,2-(Bis-trimethylsilanyloxy)butane (Preparation Example 106) was used instead of 1-(2-chlorophenyl)-(S,S)-1,2-(Bis-trimethylsilanyloxy) propane (Preparation example 69) to obtain the title compound (1.9 g, yield 60~90%).

$^1$H NMR(400 MHz, CDCl$_3$) δ1.00(t, J=7.2 Hz, 6H), 1.73~1.79(m, 1H), 3.67~3.69(m, 1H), 4.85(br s, 2H), 5.40~5.43(m, 1H), 5.49~5.54(m, 1H), 7.30~7.50(m, 3H)

Example 60

Synthesis of 1-(2,6-dichlorophenyl)-1-hydroxy-3-methyl-butyl-2-carbamate(60)

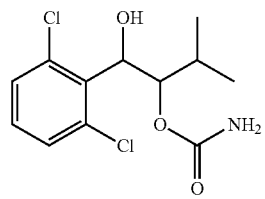 [SMILES: CC(C)C(OC(N)=O)C(O)c1c(Cl)cccc1Cl]

The substantially same method as described in Example 1 was conducted, except that 1-(2,6-dichlorophenyl)-3-methyl-1,2-(Bis-trimethylsilanyloxy)butane (Preparation Example 107) was used instead of 1-(2-chlorophenyl)-(S,S)-1,2-(Bis-trimethylsilanyloxy) propane (Preparation example 69) to obtain the title compound (1.7 g, yield 60~90%).

$^1$H NMR(400 MHz, CDCl$_3$) δ1.00(t, J=7.2 Hz, 6H), 1.73~1.79(m, 1H), 3.67~3.69(m, 1H), 4.85(br s, 2H), 5.40~5.43(m, 1H), 5.49~5.54(m, 1H), 7.16~7.33(m, 3H)

Example 61

Synthesis of 1-(2,4-dichlorophenyl)-1-hydroxy-hexyl-2-carbamate(61)

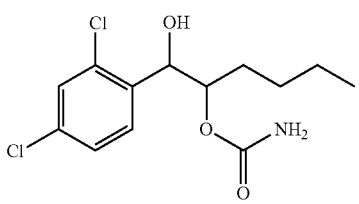 [SMILES: CCCCC(OC(N)=O)C(O)c1ccc(Cl)cc1Cl]

The substantially same method as described in Example 1 was conducted, except that 1-(2,4-dichlorophenyl)-1,2-(Bis-trimethylsilanyloxy)hexane (Preparation Example 108) was used instead of 1-(2-chlorophenyl)-(S,S)-1,2-(Bis-trimethylsilanyloxy) propane (Preparation example 69) to obtain the title compound (2.6 g, yield 60~90%).

$^1$H NMR(400 MHz, CDCl$_3$) δ0.89(t, J=3.6 Hz, 3H), 1.28~1.42(m, 4H), 1.52~1.59(m, 1H), 1.64~1.71(m, 1H), 2.98(d, J=5.6 Hz, 1H), 4.67(br s, 2H), 4.96~5.00(m, 1H), 5.17(t, J=5.6 Hz, 1H), 7.30~7.49(m, 3H)

Example 62

Synthesis of 1-(2,6-dichlorophenyl)-1-hydroxy-hexyl-2-carbamate(62)

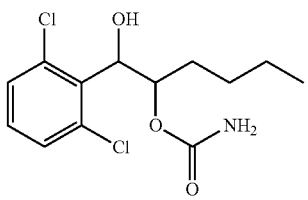 [SMILES: CCCCC(OC(N)=O)C(O)c1c(Cl)cccc1Cl]

The substantially same method as described in Example 1 was conducted, except that 1-(2,6-dichlorophenyl)-1,2-(Bis-trimethylsilanyloxy)hexane (Preparation Example 109) was used instead of 1-(2-chlorophenyl)-(S,S)-1,2-(Bis-trimethylsilanyloxy) propane (Preparation example 69) to obtain the title compound (2.5 g, yield 60~90%).

$^1$H NMR(400 MHz, CDCl$_3$) δ0.84(t, J=7.0 Hz, 3H), 1.20~1.35(m, 4H), 1.36~1.41(m, 1H), 1.59~1.63(m, 1H), 3.71(d, J=10.0 Hz, 1H), 4.74(br s, 2H), 5.40~5.44(m, 1H), 5.52~5.57(m, 1H), 7.17~7.35(m, 3H)

Example 63

Synthesis of 1-(2-fluorophenyl)-(S)-1-hydroxypropyl-(S)-2-carbamate(63)

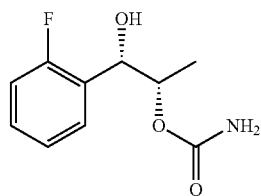

The substantially same method as described in Example 1 was conducted, except that 1-(2-fluorophenyl)-(S,S)-1,2-(Bis-trimethylsilanyloxy)propane (Preparation Example 110) was used instead of 1-(2-chlorophenyl)-(S,S)-1,2-(Bis-trimethylsilanyloxy) propane (Preparation example 69) to obtain the title compound (1.8 g, yield 60~90%).

$^1$H NMR(400 MHz, CDCl$_3$) δ1.19(d, J=5.2 Hz, 3H), 2.93(d, J=4.4 Hz, 1H), 4.71(br s, 2H), 4.99~5.06(m, H), 7.04~7.48(m, 4H)

Example 64

Synthesis of 1-(2-fluorophenyl)-(R)-1-hydroxypropyl-(R)-2-carbamate(64)

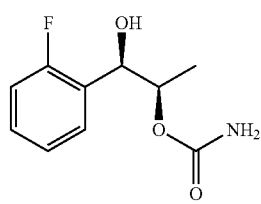

The substantially same method as described in Example 1 was conducted, except that 1-(2-fluorophenyl)-(R,R)-1,2-(Bis-trimethylsilanyloxy)propane (Preparation Example 111) was used instead of 1-(2-chlorophenyl)-(S,S)-1,2-(Bis-trimethylsilanyloxy) propane (Preparation example 69) to obtain the title compound (1.6 g, yield 60~90%).

$^1$H NMR(400 MHz, CDCl$_3$) δ1.19(d, J=5.2 Hz, 3H), 2.93(d, J=4.4 Hz, 1H), 4.71(br s, 2H), 4.99~5.06(m, H), 7.04~7.48(m, 4H)

Example 65

Synthesis of 1-(2-iodophenyl)-(S)-1-hydroxypropyl-(S)-2-carbamate(65)

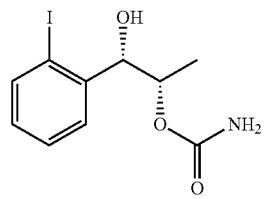

The substantially same method as described in Example 1 was conducted, except that 1-(2-iodophenyl)-(S,S)-1,2-(Bis-trimethylsilanyloxy)propane (Preparation Example 112) was used instead of 1-(2-chlorophenyl)-(S,S)-1,2-(Bis-trimethylsilanyloxy) propane (Preparation example 69) to obtain the title compound (2.2 g, yield 60~90%).

$^1$H NMR(400 MHz, CDCl$_3$) δ1.27(d, J=6.4 Hz, 3H), 3.09(br s, 1H), 4.83(br s, 2H), 5.00~5.10(m, 2H), 7.00~7.76(m, 4H)

Example 66

Synthesis of 1-(2-iodophenyl)-(R)-1-hydroxypropyl-(R)-2-carbamate(66)

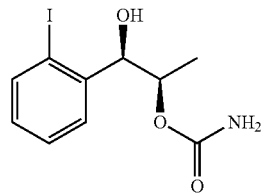

The substantially same method as described in Example 1 was conducted, except that 1-(2-iodophenyl)-(R,R)-1,2-(Bis-trimethylsilanyloxy)propane (Preparation Example 113) was used instead of 1-(2-chlorophenyl)-(S,S)-1,2-(Bis-trimethylsilanyloxy) propane (Preparation example 69) to obtain the title compound (1.7 g, yield 60~90%).

$^1$H NMR(400 MHz, CDCl$_3$) δ1.27(d, J=6.4 Hz, 3H), 2.95(d, J=3.6 Hz, 1H), 4.73(br s, 2H), 5.01~5.11(m, 2H), 7.01~7.86(m, 4H)

Example 67

Synthesis of 1-(2-iodophenyl)-(S)-1-hydroxybutyl-(S)-2-carbamate(67)

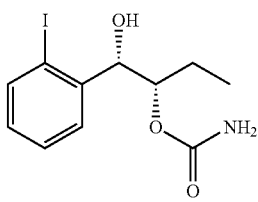 [SMILES: CC[C@H](OC(N)=O)[C@@H](O)c1ccccc1I]

The substantially same method as described in Example 1 was conducted, except that 1-(2-iodophenyl)-(S,S)-1,2-(Bis-trimethylsilanyloxy)butane (Preparation Example 114) was used instead of 1-(2-chlorophenyl)-(S,S)-1,2-(Bis-trimethylsilanyloxy) propane (Preparation example 69) to obtain the title compound (2.1 g, yield 60~90%).

$^1$H NMR(400 MHz, CDCl$_3$) δ1.27(d, J=6.4 Hz, 3H), 3.09(br s, 1H), 4.83(br s, 2H), 5.00~5.10(m, 2H), 7.00~7.76 (m, 4H)

Example 68

Synthesis of 1-(2-chlorophenyl)-(S)-2-hydroxypropyl-(S)-1-carbamate(68)

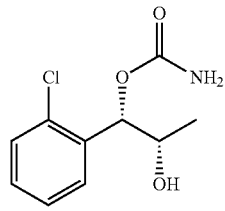

1-(2-chlorophenyl)-(S,S)-1,2-propanediol (2.33 g, Preparation example 14) obtained in Preparation Example 14, tetrahydrofuran (THF, 12 ml), and carbonyldiimidazole (CDI, 3.04 g) were put into a flask and stirred at the room temperature. After approximately 3 hours, ammonia solution (NH$_4$OH, 4 ml) was added thereto. When the reaction was completed, the obtained product was washed with 1M HCl solution and ethylacetate (EA). The separated organic layer was dehydrated with anhydrous magnesium sulfate (MgSO$_4$), filtrated, and concented under reduced pressure. The concentrated residue was purified by a silica gel column chromatography, to obtain the title compound (0.28 g, yield 10~30%).

$^1$H NMR(400 MHz, CDCl$_3$) δ1.24(d, J=6.8 Hz, 3H), 2.13(d, J=4.4 Hz, 1H), 4.12~4.16(m, 1H), 4.85(br s, 2H), 5.98(d, J=5.6 Hz, 1H), 7.24~7.43(m, 4H)

Example 69

Synthesis of 1-(2-chlorophenyl)-(R)-2-hydroxypropyl-(R)-1-carbamate(69)

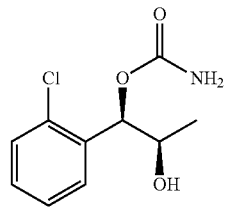

The substantially same method as described in Example 68 was conducted, except that 1-(2-chlorophenyl)-(R,R)-1,2-propanediol (Preparation Example 15) was used instead of 1-(2-chlorophenyl)-(S,S)-1,2-propanediol (Preparation example 14) to obtain the title compound (0.77 g, yield 16%).

$^1$H NMR(400 MHz, CDCl$_3$) δ1.24(d, J=6.4 Hz, 3H), 2.04(d, J=4.8 Hz, 1H), 4.11~4.18(m, 1H), 4.74(br s, 2H), 6.00(d, J=5.6 Hz, 1H), 7.24~7.43(m, 4H)

Example 70

Synthesis of 1-(2-chlorophenyl)-2-hydroxypropyl-1-carbamate(70)

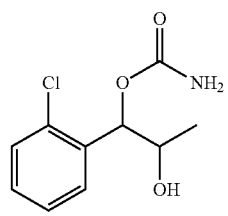

The substantially same method as described in Example 68 was conducted, except that 1-(2-chlorophenyl)-(R,R)-1, 2-propanediol (Preparation Example 16) was used instead of 1-(2-chlorophenyl)-(S,S)-1,2-propanediol (Preparation example 14) to obtain the title compound (0.16 g, yield 10~30%).

$^1$H NMR(400 MHz, CDCl$_3$) δ1.24(d, J=6.4 Hz, 3H), 2.04(d, J=4.8 Hz, 1H), 4.11~4.18(m, 1H), 4.74(br s, 2H), 6.00(d, J=5.6 Hz, 1H), 7.24~7.43(m, 4H)

Example 71

Synthesis of 1-(2-chlorophenyl)-(S)-2-hydroxypropyl-(S)-1-N-methylcarbamate(71)

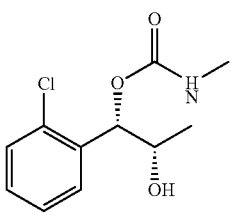 [SMILES: CNC(=O)O[C@@H](c1ccccc1Cl)[C@H](C)O]

A regioisomer of monocarbamate was separated and purified by conducting the silica gel column chromatography as described in Example 15, to obtain the title compound (0.70 g, yield 10~30%).

$^1$H NMR(400 MHz, CDCl$_3$) δ1.21(d, J=6.4 Hz, 3H), 2.80(d, J=4.8 Hz, 3H), 3.12(s, 1H), 4.09~4.16(m, 1H), 4.86(br s, 1H), 5.99(d, J=6.0 Hz, 1H), 7.23~7.40(m, 4H)

Example 72

Synthesis of 1-(2-chlorophenyl)-(R)-2-hydroxypropyl-(R)-1-N-methylcarbamate(72)

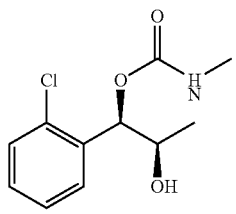 [SMILES: CNC(=O)O[C@H](c1ccccc1Cl)[C@@H](C)O]

A regioisomer of monocarbamate was separated and purified by conducting the silica gel column chromatography as described in Example 22, to obtain the title compound (0.69 g, yield 10~30%).

$^1$H NMR(400 MHz, CDCl$_3$) δ1.21(d, J=6.4 Hz, 3H), 2.80(d, J=4.8 Hz, 3H), 3.12(s, 1H), 4.09~4.16(m, 1H), 4.86(br s, 1H), 5.99(d, J=6.0 Hz, 1H), 7.23~7.40(m, 4H)

Example 73

Synthesis of 1-(2-chlorophenyl)-2-hydroxypropyl-1-N-methylcarbamate(73)

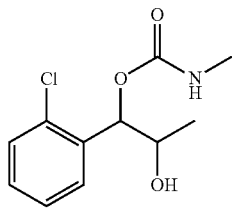 [SMILES: CNC(=O)OC(c1ccccc1Cl)C(C)O]

A regioisomer of monocarbamate was separated and purified by conducting the silica gel column chromatography as described in Example 29, to obtain the title compound (0.73 g, yield 10~30%).

$^1$H NMR(400 MHz, CDCl$_3$) δ 1.22(d, J=6 Hz, 3H), 2.15(d, J=4 Hz, 1H), 2.81(d, J=5 Hz, 3H), 4.12(dd, J=6 Hz, 1H), 4.83(br s, 1H), 6.00(d, J=6 Hz, 1H), 7.23~7.41(m, 4H)

Example 74

Synthesis of 1-(2-chlorophenyl)-(S)-2-hydroxypropyl-(S)-1-N-propylcarbamate(74)

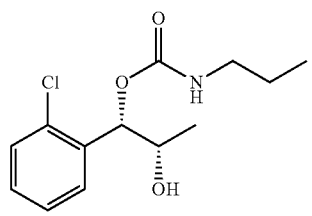 [SMILES: CCCNC(=O)O[C@@H](c1ccccc1Cl)[C@H](C)O]

A regioisomer of monocarbamate was separated and purified by conducting the silica gel column chromatography as described in Example 16, to obtain the title compound (0.15 g, yield 10~30%).

$^1$H NMR(400 MHz, CDCl$_3$) δ 0.91(t, J=7 Hz, 3H), 1.22(d, J=6 Hz, 3H), 1.52(dd, J=7 Hz, 2H), 2.23(d, J=4 Hz, 1H), 3.09~3.21(m, 2H), 4.09~4.17(m, 1H), 4.93(s, 1H), 5.99(d, J=6 Hz, 1H), 7.23~7.47(m, 4H)

Example 75

Synthesis of 1-(2-chlorophenyl)-(R)-2-hydroxypropyl-(R)-1-N-propylcarbamate(75)

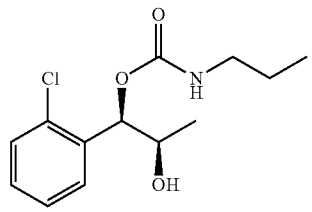 [SMILES: CCCNC(=O)O[C@H](c1ccccc1Cl)[C@@H](C)O]

A regioisomer of monocarbamate was separated and purified by conducting the silica gel column chromatography as described in Example 23, to obtain the title compound (0.04 g, yield 10~30%).

$^1$H NMR(400 MHz, CDCl$_3$) δ 0.91(t, J=7 Hz, 3H), 1.22(d, J=6 Hz, 3H), 1.52(dd, J=7 Hz, 2H), 2.23(d, J=4 Hz, 1H), 3.09~3.21(m, 2H), 4.09~4.17(m, 1H), 4.93(s, 1H), 5.99(d, J=6 Hz, 1H), 7.23~7.47(m, 4H)

Example 76

Synthesis of 1-(2-chlorophenyl)-2-hydroxypropyl-1-N-propylcarbamate(76)

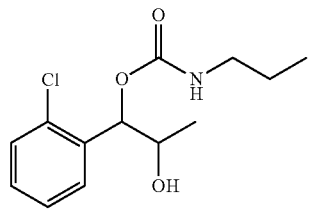 [SMILES: CCCNC(=O)OC(c1ccccc1Cl)C(C)O]

A regioisomer of monocarbamate was separated and purified by conducting the silica gel column chromatography as described in Example 30, to obtain the title compound (0.15 g, yield 10~30%).

$^1$H NMR(400 MHz, CDCl$_3$) δ 0.91(t, J=7 Hz, 3H), 1.22(d, J=6 Hz, 3H), 1.52(dd, J=7 Hz, 2H), 2.23(d, J=4 Hz, 1H), 3.09~3.21(m, 2H), 4.09~4.17(m, 1H), 4.93(s, 1H), 5.99(d, J=6 Hz, 1H), 7.23~7.47(m, 4H)

Example 77

Synthesis of 1-(2-chlorophenyl)-(S)-2-hydroxypropyl-(S)-1-N-isopropylcarbamate(77)

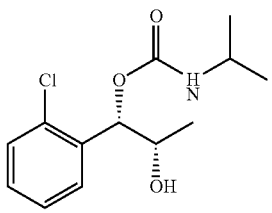 [SMILES: CC(C)NC(=O)O[C@@H](c1ccccc1Cl)[C@H](C)O]

A regioisomer of monocarbamate was separated and purified by conducting the silica gel column chromatography as described in Example 17, to obtain the title compound (0.42 g, yield 10~30%).

$^1$H NMR(400 MHz, CDCl$_3$) δ1.10(d, J=6.0 Hz, 3H), 1.15~1.19(m, 6H), 2.41(s, 1H), 3.76~4.08(m, 1H), 4.34(s, 1H), 4.83(br s 1H), 5.95(d, J=5.3 Hz, 1H), 7.19~7.39(m, 4H)

Example 78

Synthesis of 1-(2-chlorophenyl)-(R)-2-hydroxypropyl-(R)-1-N-isopropylcarbamate(78)

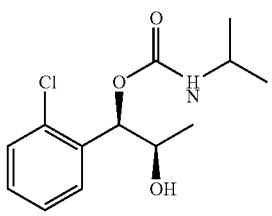 [SMILES: CC(C)NC(=O)O[C@H](c1ccccc1Cl)[C@@H](C)O]

A regioisomer of monocarbamate was separated and purified by conducting the silica gel column chromatography as described in Example 24, to obtain the title compound (0.5 g, yield 10~30%).

$^1$H NMR(400 MHz, CDCl$_3$) δ1.13(d, J=6 Hz, 3H), 1.20 (dd, J=9.2 Hz, 6H), 2.23(s, 1H), 3.77~3.82(m, 1H), 4.10(s, 1H), 4.76(br s, 1H), 5.98(d, J=5.6 Hz, 1H), 7.23~7.41(m, 4H)

Example 79

Synthesis of 1-(2-chlorophenyl)-2-hydroxypropyl-1-N-isopropylcarbamate(79)

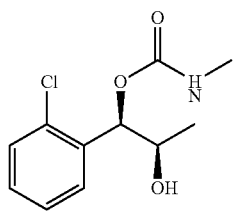 [SMILES: CNC(=O)O[C@H](c1ccccc1Cl)[C@@H](C)O]

A regioisomer of monocarbamate was separated and purified by conducting the silica gel column chromatography as described in Example 31, to obtain the title compound (0.09 g, yield 10~30%).

$^1$H NMR(400 MHz, CDCl$_3$) δ 1.14(d, J=6 Hz, 3H), 1.21(dd, J=6 Hz, 6H), 2.16(d, J=5 Hz, 1H), 3.81(t, J=6 Hz, 1H), 4.11(d, J=5 Hz, 1H), 4.73(br s, 1H), 5.98(d, J=5 Hz, 1H), 7.24~7.41(m, 4H)

Example 80

Synthesis of 1-(2-chlorophenyl)-(S)-2-hydroxypropyl-(S)-1-N-cyclopropylcarbamate(80)

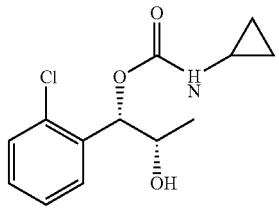 [SMILES: C[C@H](O)[C@@H](OC(=O)NC1CC1)c1ccccc1Cl]

A regioisomer of monocarbamate was separated and purified by conducting the silica gel column chromatography as described in Example 18, to obtain the title compound (0.53 g, yield 10~30%).

$^1$H NMR(400 MHz, CDCl$_3$) δ0.53~0.60(m, 2H), 0.74(s, 2H), 1.21(d, J=6.0 Hz, 3H), 2.19(s, 1H), 2.59(s, 1H), 4.11~4.15(m, 1H), 5.13(br s, 1H), 5.99(d, J=5.20 Hz, 1H), 7.23~7.40(m, 4H)

Example 81

Synthesis of 1-(2-chlorophenyl)-(R)-2-hydroxypropyl-(R)-1-N-cyclopropylcarbamate(81)

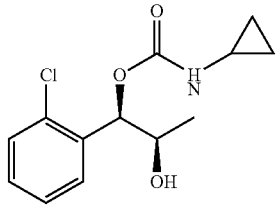 [SMILES: C[C@@H](O)[C@H](OC(=O)NC1CC1)c1ccccc1Cl]

A regioisomer of monocarbamate was separated and purified by conducting the silica gel column chromatography as described in Example 25, to obtain the title compound (0.58 g, yield 10%).

$^1$H NMR(400 MHz, CDCl$_3$) δ0.53~0.60(m, 2H), 0.74(s, 2H), 1.21(d, J=6.0 Hz, 3H), 2.19(s, 1H), 2.59(s, 1H), 4.11~4.15(m, 1H), 5.13(br s, 1H), 5.99(d, J=5.20 Hz, 1H), 7.23~7.40(m, 4H)

Example 82

Synthesis of 1-(2-chlorophenyl)-2-hydroxypropyl-1-N-cyclopropylcarbamate(82)

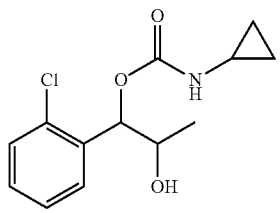 [SMILES: CC(O)C(OC(=O)NC1CC1)c1ccccc1Cl]

A regioisomer of monocarbamate was separated and purified by conducting the silica gel column chromatography as described in Example 32, to obtain the title compound (0.38 g, yield 14%).

$^1$H NMR(400 MHz, CDCl$_3$) δ 0.71(s, 2H), 1.19(d, J=6 Hz, 3H), 2.45(S, 1H), 2.57(S, 1H), 4.08~4.12(m, 1H), 5.26(s, 1H), 5.97(d, J=4 Hz, 1H), 7.22~7.54(m, 4H)

Example 83

Synthesis of 1-(2-chlorophenyl)-(S)-2-hydroxypropyl-(S)-1-N-cyclohexylcarbamate(83)

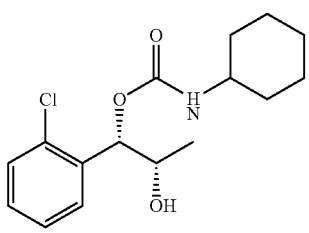 [SMILES: C[C@H](O)[C@@H](OC(=O)NC1CCCCC1)c1ccccc1Cl]

A regioisomer of monocarbamate was separated and purified by conducting the silica gel column chromatography as described in Example 19, to obtain the title compound (0.24 g, yield 10~30%).

$^1$H NMR(400 MHz, CDCl$_3$) δ1.10~1.39(m, 7H), 1.61(s, 3H), 1.71~1.74(m, 2H), 1.87(d, J=11.2 Hz, 1H), 2.48(d, J=10.8 Hz, 1H), 3.46(t, J=4 Hz, 1H), 4.10~4.11(m, 1H), 4.80(br s 1H), 5.97(d, J=5.6 Hz, 1H), 7.23~7.41(m, 4H)

Example 84

Synthesis of 1-(2-chlorophenyl)-(R)-2-hydroxypropyl-(R)-1-N-cyclohexylcarbamate(84)

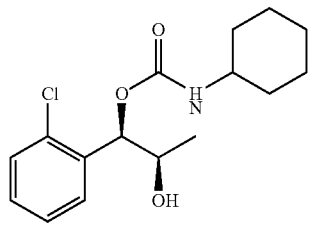 [SMILES: C[C@@H](O)[C@H](OC(=O)NC1CCCCC1)c1ccccc1Cl]

A regioisomer of monocarbamate was separated and purified by conducting the silica gel column chromatography as described in Example 26, to obtain the title compound (0.35 g, yield 10%).

$^1$H NMR(400 MHz, CDCl$_3$) δ1.10~1.39(m, 7H), 1.61(s, 3H), 1.71~1.74(m, 2H), 1.87(d, J=11.2 Hz, 1H), 2.48(d, J=10.8 Hz, 1H), 3.46(t, J=4 Hz, 1H), 4.10~4.11(m, 1H), 4.80(br s 1H), 5.97(d, J=5.6 Hz, 1H), 7.23~7.41(m, 4H)

Example 85

Synthesis of 1-(2-chlorophenyl)-2-hydroxypropyl-1-N-cyclohexylcarbamate(85)

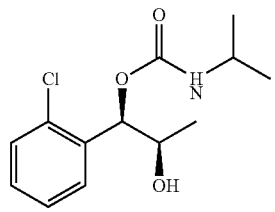 [SMILES: CC(C)NC(=O)O[C@H](c1ccccc1Cl)[C@@H](C)O]

A regioisomer of monocarbamate was separated and purified by conducting the silica gel column chromatography as described in Example 33, to obtain the title compound (0.26 g, yield 10%).

$^1$H NMR(400 MHz, CDCl$_3$) δ 1.12~1.19(m, 3H), 1.22(d, J=6 Hz, 3H), 1.27~1.37(m, 1H), 1.71(t, J=6 Hz, 2H), 1.86~1.88(m, 1H), 1.97~2.00(m, 1H), 2.18(d, J=4 Hz, 1H), 3.47(S, 1H), 4.12(t, J=6 Hz, 1H), 4.78(S, 1H), 5.97(d, J=6 Hz, 1H), 7.23~7.40(m, 4H)

Example 86

Synthesis of 1-(2-chlorophenyl)-(S)-2-hydroxypropyl-(S)-1-N-benzylcarbamate(86)

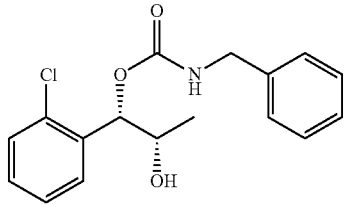 [SMILES: C[C@H](O)[C@@H](OC(=O)NCc1ccccc1)c1ccccc1Cl]

A regioisomer of monocarbamate was separated and purified by conducting the silica gel column chromatography as described in Example 20, to obtain the title compound (0.19 g, yield 10~30%).

¹H NMR(400 MHz, CDCl₃) δ 1.23(d, J=6 Hz, 3H), 2.16(d, J=4 Hz, 1H), 4.12(t, J=6 Hz, 1H), 4.31~4.44(m, 2H), 5.22(br S, 1H), 6.04(d, J=6 Hz, 1H), 7.27~7.42(m, 9H)

Example 87

Synthesis of 1-(2-chlorophenyl)-(R)-2-hydroxypropyl-(R)-1-N-benzylcarbamate(87)

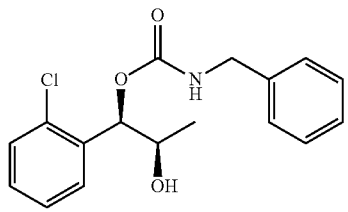 [SMILES: C[C@@H](O)[C@H](OC(=O)NCc1ccccc1)c1ccccc1Cl]

A regioisomer of monocarbamate was separated and purified by conducting the silica gel column chromatography as described in Example 27, to obtain the title compound (0.07 g, yield 10~30%).
¹H NMR(400 MHz, CDCl₃) δ 1.23(d, J=6 Hz, 3H), 2.16(d, J=4 Hz, 1H), 4.12(t, J=6 Hz, 1H), 4.31~4.44(m, 2H), 5.22(br S, 1H), 6.04(d, J=6 Hz, 1H), 7.27~7.42(m, 9H)

Example 88

Synthesis of 1-(2-chlorophenyl)-2-hydroxypropyl-1-N-benzylcarbamate(88)

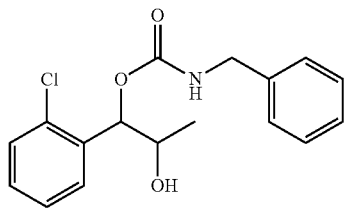 [SMILES: CC(O)C(OC(=O)NCc1ccccc1)c1ccccc1Cl]

A regioisomer of monocarbamate was separated and purified by conducting the silica gel column chromatography as described in Example 34, to obtain the title compound (0.21 g, yield 14%).
¹H NMR(400 MHz, CDCl₃) δ 1.23(d, J=6 Hz, 3H), 2.16(d, J=4 Hz, 1H), 4.12(t, J=6 Hz, 1H), 4.31~4.44(m, 2H), 5.22(br S, 1H), 6.04(d, J=6 Hz, 1H), 7.27~7.42(m, 9H)

Example 89

Synthesis of 1-(2,4-dichlorophenyl)-(S)-2-hydroxypropyl-(S)-1-carbamate(89)

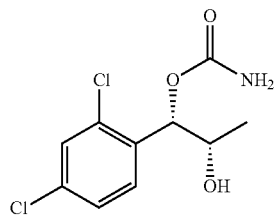 [SMILES: C[C@H](O)[C@@H](OC(N)=O)c1ccc(Cl)cc1Cl]

The substantially same method as described in Example 68 was conducted, except that 1-(2,4-dichlorophenyl)-(S,S)-1,2-propanediol (Preparation example 26) was used instead of 1-(2-chlorophenyl)-(S,S)-1,2-propanediol (Preparation example 14), to obtain the title compound (0.05 g, yield 10~30%).
¹H NMR(400 MHz, CDCl₃) δ1.13(d, J=6.8 Hz, 3H), 2.49(d, J=4.0 Hz, 1H), 4.66~4.74(m, 1H), 4.76(br s, 2H), 6.20(d, J=8.8 Hz, 1H), 7.30(d, J=8.4 Hz, 1H), 7.39(d, J=2.0 Hz, 2H), 7.50(dd, J=8.4 Hz, 2.0 Hz, 1H)

Example 90

Synthesis of 1-(2,6-dichlorophenyl)-(S)-2-hydroxypropyl-(S)-1-carbamate(90)

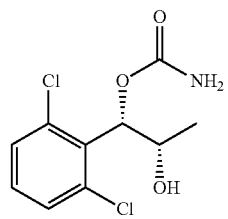 [SMILES: C[C@H](O)[C@@H](OC(N)=O)c1c(Cl)cccc1Cl]

The substantially same method as described in Example 68 was conducted, except that 1-(2,6-dichlorophenyl)-(S,S)-1,2-propanediol (Preparation example 38) was used instead of 1-(2-chlorophenyl)-(S,S)-1,2-propanediol (Preparation example 14), to obtain the title compound (0.07 g, yield 24%).
¹H NMR(400 MHz, CDCl₃) δ1.13(d, J=6.8 Hz, 3H), 2.49(d, J=4.0 Hz, 1H), 4.66~4.74(m, 1H), 4.76(br s, 2H), 6.20(d, J=8.8 Hz, 1H), 7.25~7.40(m, 3H)

Example 91

Synthesis of 1-(2,3-dichlorophenyl)-(S)-2-hydroxypropyl-(S)-1-carbamate(91)

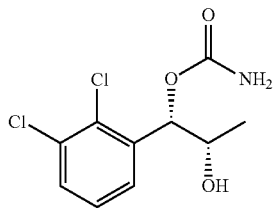 [SMILES: C[C@H](O)[C@@H](OC(N)=O)c1cccc(Cl)c1Cl]

The substantially same method as described in Example 68 was conducted, except that 1-(2,3-dichlorophenyl)-(S,S)-1,2-propanediol (Preparation example 57) was used instead of 1-(2-chlorophenyl)-(S,S)-1,2-propanediol (Preparation example 14), to obtain the title compound (0.08 g, yield 10~30%).
¹H NMR(400 MHz, CDCl₃) δ1.15(d, J=6.4 Hz, 3H), 3.66(d, J=9.2 Hz, 1H), 4.73(br s, 2H), 5.43(t, J=9.0 Hz, 1H), 5.62~5.69(m, 1H), 7.18~7.22(m, 3H),

Example 92

Synthesis of 1-(2,4-dichlorophenyl)-(S)-2-hydroxy-butyl-(S)-1-carbamate(92)

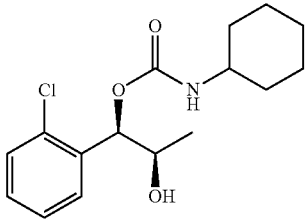 [SMILES: C[C@@H](O)[C@H](OC(=O)NC1CCCCC1)c1ccccc1Cl]

The substantially same method as described in Example 68 was conducted, except that 1-(2,4-dichlorophenyl)-(S,S)-1,2-butanediol (Preparation example 29) was used instead of 1-(2-chlorophenyl)-(S,S)-1,2-propanediol (Preparation example 14), to obtain the title compound (0.07 g, yield 10~30%).

$^1$H NMR(400 MHz, CDCl$_3$) δ0.77(t, J=7.4 Hz, 3H), 0.92~1.01(m, 1H), 1.18~1.28(m, 1H), 4.06~4.13(m, 1H), 4.96(d, J=6.0 Hz, 1H), 5.91(d, J=8.8 Hz, 1H), 6.4(br s, 2H), 7.30~7.50(m, 3H)

Example 93

Synthesis of 1-(2,6-dichlorophenyl)-(S)-2-hydroxy-butyl-(S)-1-carbamate(93)

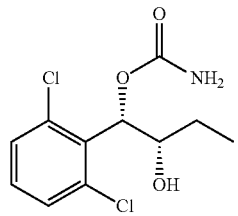 [SMILES: CC[C@H](O)[C@@H](OC(N)=O)c1c(Cl)cccc1Cl]

The substantially same method as described in Example 68 was conducted, except that 1-(2,6-dichlorophenyl)-(S,S)-1,2-butanediol (Preparation example 41) was used instead of 1-(2-chlorophenyl)-(S,S)-1,2-propanediol (Preparation example 14), to obtain the title compound (0.11 g, yield 29%).

$^1$H NMR(400 MHz, CDCl$_3$) δ0.77(t, J=7.4 Hz, 3H), 0.92~1.01(m, 1H), 1.18~1.28(m, 1H), 4.06~4.13(m, 1H), 4.96(d, J=6.0 Hz, 1H), 5.91(d, J=8.8 Hz, 1H), 6.4(br s, 2H), 7.25~7.40(m, 3H)

Example 94

Synthesis of 1-(2,4-dichlorophenyl)-(S)-2-hydroxy-3-methyl-butyl-(S)-1-carbamate(94)

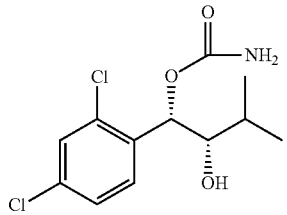 [SMILES: CC(C)[C@H](O)[C@@H](OC(N)=O)c1ccc(Cl)cc1Cl]

The substantially same method as described in Example 68 was conducted, except that 1-(2,4-dichlorophenyl)-3-methyl-(S,S)-1,2-butanediol (Preparation example 32) was used instead of 1-(2-chlorophenyl)-(S,S)-1,2-propanediol (Preparation example 14), to obtain the title compound (0.01 g, yield 10~30%).

$^1$H NMR(400 MHz, CDCl$_3$) δ1.00(t, J=7.2 Hz, 6H), 1.73~1.79(m, 1H), 3.67~3.69(m, 1H), 4.96(d, J=6.0 Hz, 1H), 5.91(d, J=8.8 Hz, 1H), 6.42(br s, 2H), 7.30~7.50(m, 3H)

Example 95

Synthesis of 1-(2,6-dichlorophenyl)-(S)-2-hydroxy-3-methyl-butyl-(S)-1-carbamate(95)

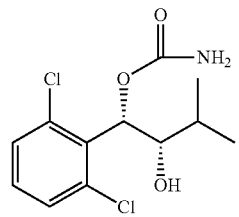 [SMILES: CC(C)[C@H](O)[C@@H](OC(N)=O)c1c(Cl)cccc1Cl]

The substantially same method as described in Example 68 was conducted, except that 1-(2,6-dichlorophenyl)-3-methyl-(S,S)-1,2-butanediol (Preparation example 44) was used instead of 1-(2-chlorophenyl)-(S,S)-1,2-propanediol (Preparation example 14), to obtain the title compound (0.03 g, yield 10~30%).

$^1$H NMR(400 MHz, CDCl$_3$) δ1.00(t, J=7.2 Hz, 6H), 1.73~1.79(m, 1H), 3.67~3.69(m, 1H), 4.96(d, J=6.0 Hz, 1H), 5.91(d, J=8.8 Hz, 1H), 6.42(br s, 2H), 7.25~7.40(m, 3H)

Example 96

Synthesis of 1-(2,4-dichlorophenyl)-(S)-2-hydroxy-hexyl-(S)-1-carbamate(96)

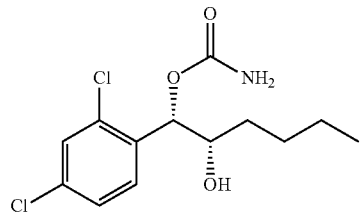 [SMILES: CCCC[C@H](O)[C@@H](OC(N)=O)c1ccc(Cl)cc1Cl]

The substantially same method as described in Example 68 was conducted, except that 1-(2,4-dichlorophenyl)-(S,S)-1,2-hexanediol (Preparation example 35) was used instead of 1-(2-chlorophenyl)-(S,S)-1,2-propanediol (Preparation example 14), to obtain the title compound (0.21 g, yield 10~30%).

$^1$H NMR(400 MHz, CDCl$_3$) δ0.85(t, J=7.2 Hz, 3H), 1.18~1.33(m, 4H), 1.48~1.55(m, 2H), 2.35(d, J=4.4 Hz, 1H), 4.45~4.50(m, 1H), 4.76(br s, 2H), 6.21(d, J=8.4 Hz, 1H), 7.30~7.50(m, 3H)

Example 97

Synthesis of 1-(2,6-dichlorophenyl)-(S)-2-hydroxy-hexyl-(S)-1-carbamate(97)

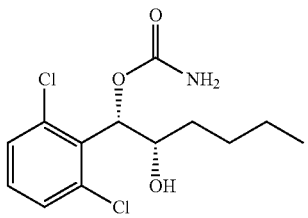

The substantially same method as described in Example 68 was conducted, except that 1-(2,6-dichlorophenyl)-(S,S)-1,2-hexanediol (Preparation example 47) was used instead of 1-(2-chlorophenyl)-(S,S)-1,2-propanediol (Preparation example 14), to obtain the title compound (0.06 g, yield 29%).

$^1$H NMR(400 MHz, CDCl$_3$) δ0.85(t, J=7.2 Hz, 3H), 1.18~1.33(m, 4H), 1.48~1.55(m, 2H), 2.35(d, J=4.4 Hz, 1H), 4.45~4.50(m, 1H), 4.76(br s, 2H), 6.21(d, J=8.4 Hz, 1H), 7.16~7.34(m, 3H)

Example 98

Synthesis of 1-(2,4-dichlorophenyl)-(R)-2-hydroxy-propyl-(R)-1-carbamate(98)

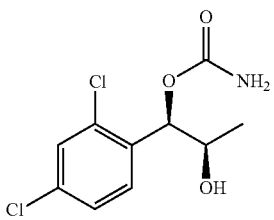 [SMILES: C[C@@H](O)[C@H](OC(N)=O)c1ccc(Cl)cc1Cl]

The substantially same method as described in Example 68 was conducted, except that 1-(2,4-dichlorophenyl)-(R,R)-1,2-propanediol (Preparation example 27) was used instead of 1-(2-chlorophenyl)-(S,S)-1,2-propanediol (Preparation example 14), to obtain the title compound (0.04 g, yield 10~30%).

$^1$H NMR(400 MHz, CDCl$_3$) δ1.13(d, J=6.8 Hz, 3H), 2.49(d, J=4.0 Hz, 1H), 4.66~4.74(m, 1H), 4.76(br s, 2H), 6.20(d, J=8.8 Hz, 1H), 7.30~7.50(m, 3H)

Example 99

Synthesis of 1-(2,6-dichlorophenyl)-(R)-2-hydroxy-propyl-(R)-1-carbamate(99)

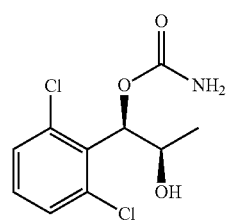 [SMILES: C[C@@H](O)[C@H](OC(N)=O)c1c(Cl)cccc1Cl]

The substantially same method as described in Example 68 was conducted, except that 1-(2,6-dichlorophenyl)-(R,R)-1,2-propanediol (Preparation example 39) was used instead of 1-(2-chlorophenyl)-(S,S)-1,2-propanediol (Preparation example 14), to obtain the title compound (0.09 g, yield 10~30%).

$^1$H NMR(400 MHz, CDCl$_3$) δ1.13(d, J=6.8 Hz, 3H), 2.49(d, J=4.0 Hz, 1H), 4.66~4.74(m, 1H), 4.76(br s, 2H), 6.20(d, J=8.8 Hz, 1H), 7.25~7.40(m, 3H)

Example 100

Synthesis of 1-(2,3-dichlorophenyl)-(R)-2-hydroxy-propyl-(R)-1-carbamate(100)

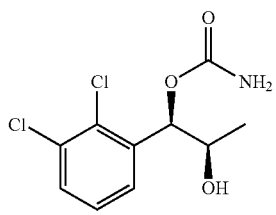 [SMILES: C[C@@H](O)[C@H](OC(N)=O)c1cccc(Cl)c1Cl]

The substantially same method as described in Example 68 was conducted, except that 1-(2,3-dichlorophenyl)-(R,R)-1,2-propanediol (Preparation example 58) was used instead of 1-(2-chlorophenyl)-(S,S)-1,2-propanediol (Preparation example 14), to obtain the title compound (0.25 g, yield 10~30%).

$^1$H NMR(400 MHz, CDCl$_3$) δ1.15(d, J=6.4 Hz, 3H), 3.66(d, J=9.2 Hz, 1H), 4.73(br s, 2H), 5.43(t, J=9.0 Hz, 1H), 5.62~5.69(m, 1H), 7.18~7.22(m, 3H),

Example 101

Synthesis of 1-(2,4-dichlorophenyl)-(R)-2-hydroxy-butyl-(R)-1-carbamate(101)

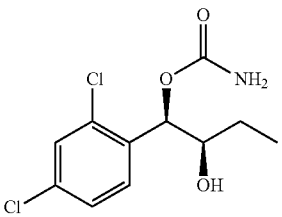 [SMILES: CC[C@@H](O)[C@H](OC(N)=O)c1ccc(Cl)cc1Cl]

The substantially same method as described in Example 68 was conducted, except that 1-(2,4-dichlorophenyl)-(R,R)-1,2-butanediol (Preparation example 30) was used instead of 1-(2-chlorophenyl)-(S,S)-1,2-propanediol (Preparation example 14), to obtain the title compound (0.08 g, yield 10~30%).

$^1$H NMR(400 MHz, CDCl$_3$) δ0.77(t, J=7.4 Hz, 3H), 0.92~1.01(m, 1H), 1.18~1.28(m, 1H), 4.06~4.13(m, 1H), 4.96(d, J=6.0 Hz, 1H), 5.91(d, J=8.8 Hz, 1H), 6.4(br s, 2H), 7.30~7.50(m, 3H)

Example 102

Synthesis of 1-(2,6-dichlorophenyl)-(R)-2-hydroxy-butyl-(R)-1-carbamate(102)

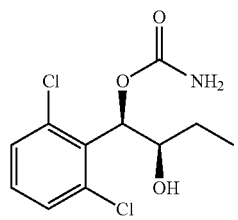 [SMILES: CC[C@@H](O)[C@H](OC(N)=O)c1c(Cl)cccc1Cl]

The substantially same method as described in Example 68 was conducted, except that 1-(2,6-dichlorophenyl)-(R,R)-1,2-butanediol (Preparation example 42) was used instead of 1-(2-chlorophenyl)-(S,S)-1,2-propanediol (Preparation example 14), to obtain the title compound (0.09 g, yield 10~30%). $^1$H NMR(400 MHz, CDCl$_3$) δ0.77(t, J=7.4 Hz, 3H), 0.92~1.01(m, 1H), 1.18~1.28(m, 1H), 4.06~4.13(m, 1H), 4.96(d, J=6.0 Hz, 1H), 5.91(d, J=8.8 Hz, 1H), 6.4(br s, 2H), 7.25~7.40(m, 3H)

Example 103

Synthesis of 1-(2,4-dichlorophenyl)-(R)-2-hydroxy-3-methyl-butyl-(R)-1-carbamate(103)

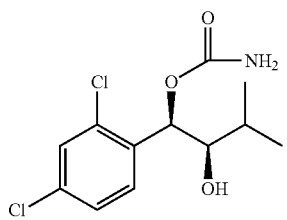 [SMILES: CC(C)[C@@H](O)[C@H](OC(N)=O)c1ccc(Cl)cc1Cl]

The substantially same method as described in Example 68 was conducted, except that 1-(2,4-dichlorophenyl)-3-methyl-(R,R)-1,2-propanediol (Preparation example 33) was used instead of 1-(2-chlorophenyl)-(S,S)-1,2-propanediol (Preparation example 14), to obtain the title compound (0.01 g, yield 10~30%).

$^1$H NMR(400 MHz, CDCl$_3$) δ1.00(t, J=7.2 Hz, 6H), 1.73~1.79(m, 1H), 3.67~3.69(m, 1H), 4.96(d, J=6.0 Hz, 1H), 5.91(d, J=8.8 Hz, 1H), 6.42(br s, 2H), 7.30~7.50(m, 3H)

Example 104

Synthesis of 1-(2,6-dichlorophenyl)-(R)-2-hydroxy-3-methyl-butyl-(R)-1-carbamate(104)

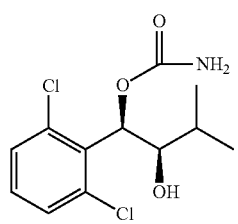 [SMILES: CC(C)[C@@H](O)[C@H](OC(N)=O)c1c(Cl)cccc1Cl]

The substantially same method as described in Example 68 was conducted, except that 1-(2,6-dichlorophenyl)-3-methyl-(R,R)-1,2-propanediol (Preparation example 45) was used instead of 1-(2-chlorophenyl)-(S,S)-1,2-propanediol (Preparation example 14), to obtain the title compound (0.01 g, yield 10~30%).

$^1$H NMR(400 MHz, CDCl$_3$) δ1.00(t, J=7.2 Hz, 6H), 1.73~1.79(m, 1H), 3.67~3.69(m, 1H), 4.96(d, J=6.0 Hz, 1H), 5.91(d, J=8.8 Hz, 1H), 6.42(br s, 2H), 7.25~7.40(m, 3H)

Example 105

Synthesis of 1-(2,4-dichlorophenyl)-(R)-2-hydroxy-hexyl-(R)-1-carbamate(105)

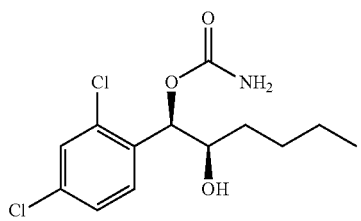 [SMILES: CCCC[C@@H](O)[C@H](OC(N)=O)c1ccc(Cl)cc1Cl]

The substantially same method as described in Example 68 was conducted, except that 1-(2,4-dichlorophenyl)-(R,R)-1,2-hexanediol (Preparation example 36) was used instead of 1-(2-chlorophenyl)-(S,S)-1,2-propanediol (Preparation example 14), to obtain the title compound (0.21 g, yield 10~30%).

$^1$H NMR(400 MHz, CDCl$_3$) δ0.85(t, J=7.2 Hz, 3H), 1.18~1.33(m, 4H), 1.48~1.55(m, 2H), 2.35(d, J=4.4 Hz, 1H), 4.45~4.50(m, 1H), 4.76(br s, 2H), 6.21(d, J=8.4 Hz, 1H), 7.30~7.50(m, 3H)

Example 106

Synthesis of 1-(2,6-dichlorophenyl)-(R)-2-hydroxy-hexyl-(R)-1-carbamate(106)

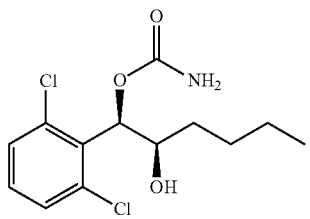 [SMILES: CCCC[C@@H](O)[C@H](OC(N)=O)c1c(Cl)cccc1Cl]

The substantially same method as described in Example 68 was conducted, except that 1-(2,6-dichlorophenyl)-(R,R)-1,2-hexanediol (Preparation example 48) was used instead of 1-(2-chlorophenyl)-(S,S)-1,2-propanediol (Preparation example 14), to obtain the title compound (0.12 g, yield 10~30%).

$^1$H NMR(400 MHz, CDCl$_3$) δ0.85(t, J=7.2 Hz, 3H), 1.18~1.33(m, 4H), 1.48~1.55(m, 2H), 2.35(d, J=4.4 Hz, 1H), 4.45~4.50(m, 1H), 4.76(br s, 2H), 6.21(d, J=8.4 Hz, 1H), 7.16~7.34(m, 3H)

Example 107

Synthesis of 1-(2,4-dichlorophenyl)-2-hydroxypropyl-1-carbamate(107)

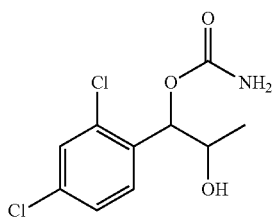 [SMILES: CC(O)C(OC(N)=O)c1ccc(Cl)cc1Cl]

The substantially same method as described in Example 68 was conducted, except that 1-(2,4-dichlorophenyl)-1,2-propanediol (Preparation example 28) was used instead of 1-(2-chlorophenyl)-(S,S)-1,2-propanediol (Preparation example 14), to obtain the title compound (0.05 g, yield 10~30%).

$^1$H NMR(400 MHz, CDCl$_3$) δ1.13(d, J=6.8 Hz, 3H), 2.49(d, J=4.0 Hz, 1H), 4.66~4.74(m, 1H), 4.76(br s, 2H), 6.20(d, J=8.8 Hz, 1H), 7.30~7.50(m, 3H)

Example 108

Synthesis of 1-(2,6-dichlorophenyl)-2-hydroxypropyl-1-carbamate(108)

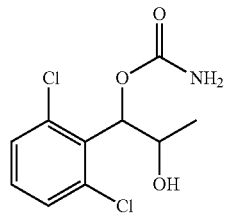 [SMILES: CC(O)C(OC(N)=O)c1c(Cl)cccc1Cl]

The substantially same method as described in Example 68 was conducted, except that 1-(2,6-dichlorophenyl)-1,2-propanediol (Preparation example 40) was used instead of 1-(2-chlorophenyl)-(S,S)-1,2-propanediol (Preparation example 14), to obtain the title compound (0.06 g, yield 10~30%).

$^1$H NMR(400 MHz, CDCl$_3$) δ1.13(d, J=6.8 Hz, 3H), 2.49(d, J=4.0 Hz, 1H), 4.66~4.74(m, 1H), 4.76(br s, 2H), 6.20(d, J=8.8 Hz, 1H), 7.25~7.40(m, 3H)

Example 109

Synthesis of 1-(2,3-dichlorophenyl)-(R)-2-hydroxypropyl-(R)-1-carbamate(109)

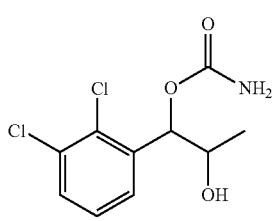 [SMILES: CC(O)C(OC(N)=O)c1cccc(Cl)c1Cl]

The substantially same method as described in Example 68 was conducted, except that 1-(2,3-dichlorophenyl)-1,2-propanediol (Preparation example 59) was used instead of 1-(2-chlorophenyl)-(S,S)-1,2-propanediol (Preparation example 14), to obtain the title compound (0.02 g, yield 10~30%).

$^1$H NMR(400 MHz, CDCl$_3$) δ1.15(d, J=6.4 Hz, 3H), 3.66(d, J=9.2 Hz, 1H), 4.73(br s, 2H), 5.43(t, J=9.0 Hz, 1H), 5.62~5.69(m, 1H), 7.18~7.22(m, 3H),

Example 110

Synthesis of 1-(2,4-dichlorophenyl)-2-hydroxybutyl-1-carbamate(110)

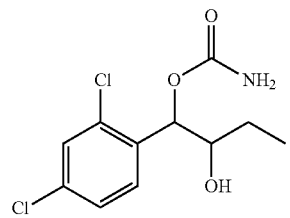 [SMILES: CCC(O)C(OC(N)=O)c1ccc(Cl)cc1Cl]

The substantially same method as described in Example 68 was conducted, except that 1-(2,4-dichlorophenyl)-1,2-butanediol (Preparation example 31) was used instead of 1-(2-chlorophenyl)-(S,S)-1,2-propanediol (Preparation example 14), to obtain the title compound (0.07 g, yield 10~30%).

$^1$H NMR(400 MHz, CDCl$_3$) δ0.77(t, J=7.4 Hz, 3H), 0.92~1.01(m, 1H), 1.18~1.28(m, 1H), 4.06~4.13(m, 1H), 4.96(d, J=6.0 Hz, 1H), 5.91(d, J=8.8 Hz, 1H), 6.4(br s, 2H), 7.30~7.50(m, 3H)

Example 111

Synthesis of 1-(2,6-dichlorophenyl)-2-hydroxybutyl-1-carbamate(111)

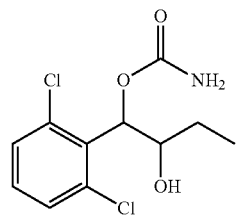 [SMILES: CCC(O)C(OC(N)=O)c1c(Cl)cccc1Cl]

The substantially same method as described in Example 68 was conducted, except that 1-(2,6-dichlorophenyl)-1,2-butanediol (Preparation example 43) was used instead of 1-(2-chlorophenyl)-(S,S)-1,2-propanediol (Preparation example 14), to obtain the title compound (0.10 g, yield 10~30%).

$^1$H NMR(400 MHz, CDCl$_3$) δ0.77(t, J=7.4 Hz, 3H), 0.92~1.01(m, 1H), 1.18~1.28(m, 1H), 4.06~4.13(m, 1H), 4.96(d, J=6.0 Hz, 1H), 5.91(d, J=8.8 Hz, 1H), 6.4(br s, 2H), 7.25~7.40(m, 3H)

Example 112

Synthesis of 1-(2,4-dichlorophenyl)-2-hydroxy-3-methyl-butyl-1-carbamate(112)

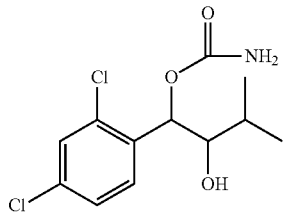 [SMILES: CC(C)C(O)C(OC(N)=O)c1ccc(Cl)cc1Cl]

The substantially same method as described in Example 68 was conducted, except that 1-(2,4-dichlorophenyl)-3-methyl-1,2-propanediol (Preparation example 34) was used instead of 1-(2-chlorophenyl)-(S,S)-1,2-propanediol (Preparation example 14), to obtain the title compound (0.04 g, yield 10~30%).

$^1$H NMR(400 MHz, CDCl$_3$) δ1.00(t, J=7.2 Hz, 6H), 1.73~1.79(m, 1H), 3.67~3.69(m, 1H), 4.96(d, J=6.0 Hz, 1H), 5.91(d, J=8.8 Hz, 1H), 6.42(br s, 2H), 7.30~7.50(m, 3H)

Example 113

Synthesis of 1-(2,6-dichlorophenyl)-2-hydroxy-3-methyl-butyl-1-carbamate(113)

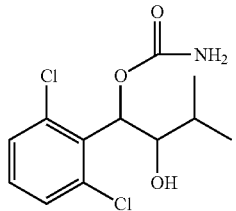 [SMILES: CC(C)C(O)C(OC(N)=O)c1c(Cl)cccc1Cl]

The substantially same method as described in Example 68 was conducted, except that 1-(2,6-dichlorophenyl)-3-methyl-1,2-propanediol (Preparation example 46) was used instead of 1-(2-chlorophenyl)-(S,S)-1,2-propanediol (Preparation example 14), to obtain the title compound (0.01 g, yield 10~30%).

$^1$H NMR(400 MHz, CDCl$_3$) δ1.00(t, J=7.2 Hz, 6H), 1.73~1.79(m, 1H), 3.67~3.69(m, 1H), 4.96(d, J=6.0 Hz, 1H), 5.91(d, J=8.8 Hz, 1H), 6.42(br s, 2H), 7.25~7.40(m, 3H)

Example 114

Synthesis of 1-(2,4-dichlorophenyl)-2-hydroxy-hexyl-1-carbamate(114)

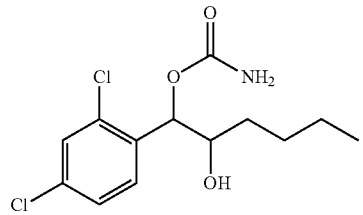

The substantially same method as described in Example 68 was conducted, except that 1-(2,4-dichlorophenyl)-1,2-hexanediol (Preparation example 37) was used instead of 1-(2-chlorophenyl)-(S,S)-1,2-propanediol (Preparation example 14), to obtain the title compound (0.21 g, yield 10~30%).

$^1$H NMR(400 MHz, CDCl$_3$) δ0.85(t, J=7.2 Hz, 3H), 1.18~1.33(m, 4H), 1.48~1.55(m, 2H), 2.35(d, J=4.4 Hz, 1H), 4.45~4.50(m, 1H), 4.76(br s, 2H), 6.21(d, J=8.4 Hz, 1H), 7.30~7.50(m, 3H)

Example 115

Synthesis of 1-(2,6-dichlorophenyl)-2-hydroxy-hexyl-1-carbamate(115)

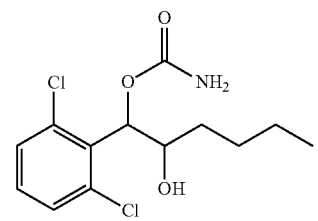

The substantially same method as described in Example 68 was conducted, except that 1-(2,6-dichlorophenyl)-1,2-hexanediol (Preparation example 49) was used instead of 1-(2-chlorophenyl)-(S,S)-1,2-propanediol (Preparation example 14), to obtain the title compound (0.12 g, yield 10~30%).

$^1$H NMR(400 MHz, CDCl$_3$) δ0.85(t, J=7.2 Hz, 3H), 1.18~1.33(m, 4H), 1.48~1.55(m, 2H), 2.35(d, J=4.4 Hz, 1H), 4.45~4.50(m, 1H), 4.76(br s, 2H), 6.21(d, J=8.4 Hz, 1H), 7.16~7.34(m, 3H)

Compounds 1 to 115 produced in Examples 1 to 115 were summarized in following Tables 1 and 2.

TABLE 1

Compounds 1 to 67 having the structure of Chemical Formula 1 where 'A' is a carbamoyl derivative and 'B' is H

| No. | X | n (position) | $1^{st}$ Chiral | $2^{nd}$ Chiral | $R^1$ | A<br>A = carbamoyl<br>derivative $R^2$ = | B<br>B = H |
|---|---|---|---|---|---|---|---|
| 1 | Cl | 1(2-) | S | S | Me | H | H |
| 2 | Cl | 1(2-) | R | R | Me | H | H |
| 3 | Cl | 1(2-) | Rac. | Rac. | Me | H | H |
| 4 | Cl | 1(2-) | S | R | Me | H | H |

TABLE 1-continued

Compounds 1 to 67 having the structure of Chemical Formula 1 where 'A' is a carbamoyl derivative and 'B' is H

| No. | X | n (position) | 1st Chiral | 2nd Chiral | $R^1$ | A<br>A = carbamoyl<br>derivative $R^2$ = | B<br>B = H |
|---|---|---|---|---|---|---|---|
| 5 | Cl | 1(2-) | R | S | Me | H | H |
| 6 | Cl | 1(2-) | S | S | Et | H | H |
| 7 | Cl | 1(2-) | R | R | Et | H | H |
| 8 | Cl | 1(2-) | Rac. | Rac. | Et | H | H |
| 9 | Cl | 1(2-) | S | S | Isopropyl | H | H |
| 10 | Cl | 1(2-) | R | R | Isopropyl | H | H |
| 11 | Cl | 1(2-) | Rac. | Rac. | Isopropyl | H | H |
| 12 | Cl | 1(2-) | S | S | butyl | H | H |
| 13 | Cl | 1(2-) | R | R | butyl | H | H |
| 14 | Cl | 1(2-) | Rac. | Rac. | butyl | H | H |
| 15 | Cl | 1(2-) | S | S | Me | Me | H |
| 16 | Cl | 1(2-) | S | S | Me | Propyl | H |
| 17 | Cl | 1(2-) | S | S | Me | Isopropyl | H |
| 18 | Cl | 1(2-) | S | S | Me | Cyclopropyl | H |
| 19 | Cl | 1(2-) | S | S | Me | Cyclohexyl | H |
| 20 | Cl | 1(2-) | S | S | Me | Benzyl | H |
| 21 | Cl | 1(2-) | S | S | Me | Bicyclo[2.2.1]heptane | H |
| 22 | Cl | 1(2-) | R | R | Me | Me | H |
| 23 | Cl | 1(2-) | R | R | Me | Propyl | H |
| 24 | Cl | 1(2-) | R | R | Me | Isopropyl | H |
| 25 | Cl | 1(2-) | R | R | Me | Cyclopropyl | H |
| 26 | Cl | 1(2-) | R | R | Me | Cyclohexyl | H |
| 27 | Cl | 1(2-) | R | R | Me | Benzyl | H |
| 28 | Cl | 1(2-) | R | R | Me | Bicyclo[2.2.1]heptane | H |
| 29 | Cl | 1(2-) | Rac. | Rac. | Me | Me | H |
| 30 | Cl | 1(2-) | Rac. | Rac. | Me | Propyl | H |
| 31 | Cl | 1(2-) | Rac. | Rac. | Me | Isopropyl | H |
| 32 | Cl | 1(2-) | Rac. | Rac. | Me | Cyclopropyl | H |
| 33 | Cl | 1(2-) | Rac. | Rac. | Me | Cyclohexyl | H |
| 34 | Cl | 1(2-) | Rac. | Rac. | Me | Benzyl | H |
| 35 | Cl | 1(2-) | Rac, | Rac. | Me | Bicyclo[2.2.1]heptane | H |
| 36 | Cl | 2(2,4-) | S | S | Me | H | H |
| 37 | Cl | 2(2,6-) | S | S | Me | H | H |
| 38 | Cl | 2(2,3-) | S | S | Me | H | H |
| 39 | Cl | 2(2,4-) | S | S | Et | H | H |
| 40 | Cl | 2(2,6-) | S | S | Et | H | H |
| 41 | Cl | 2(2,4-) | S | S | Isopropyl | H | H |
| 42 | Cl | 2(2,6-) | S | S | Isopropyl | H | H |
| 43 | Cl | 2(2,4-) | S | S | butyl | H | H |
| 44 | Cl | 2(2,6-) | S | S | butyl | H | H |
| 45 | Cl | 2(2,4-) | R | R | Me | H | H |
| 46 | Cl | 2(2,6-) | R | R | Me | H | H |
| 47 | Cl | 2(2,3-) | R | R | Me | H | H |
| 48 | Cl | 2(2,4-) | R | R | Et | H | H |
| 49 | Cl | 2(2,6-) | R | R | Et | H | H |
| 50 | Cl | 2(2,4-) | R | R | Isopropyl | H | H |
| 51 | Cl | 2(2,6-) | R | R | Isopropyl | H | H |
| 52 | Cl | 2(2,4-) | R | R | butyl | H | H |
| 53 | Cl | 2(2,6-) | R | R | butyl | H | H |
| 54 | Cl | 2(2,4-) | Rac, | Rac. | Me | H | H |
| 55 | Cl | 2(2,6-) | Rac, | Rac. | Me | H | H |
| 56 | Cl | 2(2,3-) | Rac, | Rac. | Me | H | H |
| 57 | Cl | 2(2,4-) | Rac, | Rac. | Et | H | H |
| 58 | Cl | 2(2,6-) | Rac, | Rac. | Et | H | H |
| 59 | Cl | 2(2,4-) | Rac, | Rac. | Isopropyl | H | H |
| 60 | Cl | 2(2,6-) | Rac, | Rac. | Isopropyl | H | H |
| 61 | Cl | 2(2,4-) | Rac, | Rac. | butyl | H | H |
| 62 | Cl | 2(2,6-) | Rac, | Rac. | butyl | H | H |
| 63 | F | 1(2-) | S | S | Me | H | H |
| 64 | F | 1(2-) | R | R | Me | H | H |
| 65 | I | 1(2-) | S | S | Me | H | H |
| 66 | I | 1(2-) | R | R | Me | H | H |
| 67 | I | 1(2-) | S | S | Et | H | H |

TABLE 2

Compounds 68 to 115 having the structure of Chemical Formula 1 where 'A' is H and 'B' is a carbamoyl derivative

| No. | X | n (position) | 1st Chiral | 2nd Chiral | R¹ | A A = H | B B = carbamoyl derivative R³ = |
|-----|-----|-----|-----|-----|-----|-----|-----|
| 68 | Cl | 1(2-) | S | S | Me | H | H |
| 69 | Cl | 1(2-) | R | R | Me | H | H |
| 70 | Cl | 1(2-) | Rac. | Rac. | Me | H | H |
| 71 | Cl | 1(2-) | S | S | Me | H | Me |
| 72 | Cl | 1(2-) | R | R | Me | H | Me |
| 73 | Cl | 1(2-) | Rac. | Rac. | Me | H | Me |
| 74 | Cl | 1(2-) | S | S | Me | H | Propyl |
| 75 | Cl | 1(2-) | R | R | Me | H | Propyl |
| 76 | Cl | 1(2-) | Rac. | Rac. | Me | H | Propyl |
| 77 | Cl | 1(2-) | S | S | Me | H | Isopropyl |
| 78 | Cl | 1(2-) | R | R | Me | H | Isopropyl |
| 79 | Cl | 1(2-) | Rac. | Rac. | Me | H | Isopropyl |
| 80 | Cl | 1(2-) | S | S | Me | H | Cyclopropyl |
| 81 | Cl | 1(2-) | R | R | Me | H | Cyclopropyl |
| 82 | Cl | 1(2-) | Rac. | Rac. | Me | H | Cyclopropyl |
| 83 | Cl | 1(2-) | S | S | Me | H | Cyclohexyl |
| 84 | Cl | 1(2-) | R | R | Me | H | Cyclohexyl |
| 85 | Cl | 1(2-) | Rac. | Rac. | Me | H | Cyclohexyl |
| 86 | Cl | 1(2-) | S | S | Me | H | Benzyl |
| 87 | Cl | 1(2-) | R | R | Me | H | Benzyl |
| 88 | Cl | 1(2-) | Rac. | Rac. | Me | H | Benzyl |
| 89 | Cl | 2(2,4-) | S | S | Me | H | H |
| 90 | Cl | 2(2,6-) | S | S | Me | H | H |
| 91 | Cl | 2(2,3-) | S | S | Me | H | H |
| 92 | Cl | 2(2,4-) | S | S | Et | H | H |
| 93 | Cl | 2(2,6-) | S | S | Et | H | H |
| 94 | Cl | 2(2,4-) | S | S | Isopropyl | H | H |
| 95 | Cl | 2(2,6-) | S | S | Isopropyl | H | H |
| 96 | Cl | 2(2,4-) | S | S | Butyl | H | H |
| 97 | Cl | 2(2,6-) | S | S | Butyl | H | H |
| 98 | Cl | 2(2,4-) | R | R | Me | H | H |
| 99 | Cl | 2(2,6-) | R | R | Me | H | H |
| 100 | Cl | 2(2,3-) | R | R | Me | H | H |
| 101 | Cl | 2(2,4-) | R | R | Et | H | H |
| 102 | Cl | 2(2,6-) | R | R | Et | H | H |
| 103 | Cl | 2(2,4-) | R | R | Isopropyl | H | H |
| 104 | Cl | 2(2,6-) | R | R | Isopropyl | H | H |
| 105 | Cl | 2(2,4-) | R | R | Butyl | H | H |
| 106 | Cl | 2(2,6-) | R | R | Butyl | H | H |
| 107 | Cl | 2(2,4-) | Rac. | Rac. | Me | H | H |
| 108 | Cl | 2(2,6-) | Rac. | Rac. | Me | H | H |
| 109 | Cl | 2(2,3-) | Rac. | Rac. | Me | H | H |
| 110 | Cl | 2(2,4-) | Rac. | Rac. | Et | H | H |
| 111 | Cl | 2(2,6-) | Rac. | Rac. | Et | H | H |
| 112 | Cl | 2(2,4-) | Rac. | Rac. | Isopropyl | H | H |
| 113 | Cl | 2(2,6-) | Rac. | Rac. | Isopropyl | H | H |
| 114 | Cl | 2(2,4-) | Rac. | Rac. | Butyl | H | H |
| 115 | Cl | 2(2,6-) | Rac. | Rac. | Butyl | H | H |

Example 116

Lithium-Pilocarpine Induced Status Epilepticus Model

Prevention Study

Male Sprague-Dawley rats (purchased from Orient Bio Inc. Korea) of body weight 200-230 g were used for these studies and housed 4-5 rats per a cage for 4-5 days. On the day prior to status epilepsy (SE), rats received 127 mg/kg lithium chloride (Sigma, St. Louis, Mo., U.S.A.) intraperitoneally (i.p.). Approximately 18-20 h following this treatment, the rats were given 43 mg/kg pilocarpine (Sigma) intraperitoneally. An i.p. injection of 2 mg/kg methyl-scopolamine (Sigma) was administered 30 min prior to pilocarpine to block the effects of the muscarinic agonist on peripheral cholinergic receptors. The test drug was administered intraperitoneally (i.p.) in a volume of 2 ul/g body weight. Pharmacological effects of all the test materials were evaluated to compare the test groups (n=6) with a control group (n=6). Control group was administered vehicle, only. The peak time was determined by administration test material's random dose for 0.5, 1, 2, 4 hour. The time that the most protect was defined peak time and ED50 was determined by other dose administration at peak time. The animals were then transferred to observation cages and observed continuously for 90 min. The seizure activity was elicited in approximately 95% of control group. Protection was defined as a complete absence of seizure grade 4~5 based on Racine scale (Racine, 1972) over the 90-min observation period. The effective dose of compound necessary to protect against seizures to 50% of controls (i.e. ED50) was determined by log probit analysis using SPSS software program (SPSS Inc.). The obtained results are shown in following Table 3.

Intervention Study

Male Sprague-Dawley rats (purchased from Orient Bio Inc. Korea) of body weight 200-230 g were used for these studies and housed 4-5 rats per a cage for 4-5 days. On the day prior to SE, rats received 127 mg/kg lithium chloride (Sigma, St. Louis, Mo., U.S.A.) intraperitoneally (i.p.). Approximately 18-20 h following this treatment, the rats were given 43 mg/kg pilocarpine (Sigma) intraperitoneally. An i.p. injection of 2 mg/kg methyl-scopolamine (Sigma) was administered 30 min prior to pilocarpine to block the effects of the muscarinic agonist on peripheral cholinergic receptors. The effects of the test compounds dissolved in 30% Poly Ethylene Glycol 400(Acros Organics, Geel, Belgium) or 20% Tween80 were studied at various times or 30 min after the occurrence of the first motor seizure or SE onset. The drug was administered intraperitoneally in a volume of 2 ul/g body weight. Pharmacological effects was evaluated to compare the test groups with a control group (n=8). Control group was administered vehicle, only. The obtained results are shown in following Table 4. (Reference; Racine R. J. (1972). Modification of seizure activity by electrical stimulation: II Motor seizure. Electroenceph. Clin. Neurophysiol. 32: 281-294.)

TABLE 3

Measurement results of Lithium-pilocarpine induced status epilepticus of compounds in the test (Rats)

| Compound (Example) No. | Therapeutic effect Prevention(rat, ip) | |
|---|---|---|
| | ED50(mg/kg) | Peak Time(h) |
| 1 | 18.0 | 2 |
| 2 | 71.9 | 0.5 |
| 3 | 31.7 | 0.5 |
| 4 | $^a$60 (50%) | — |
| 6 | $^a$60 (100%) | — |
| 8 | $^a$60 (83.3%) | — |
| 9 | $^a$60 (83.3%) | — |
| 25 | $^a$60 (100%) | — |
| 29 | $^a$60 (100%) | — |
| 30 | $^a$73.6 (50%) | — |
| 32 | $^a$60 (100%) | — |
| 36 | $^a$73.6 (100%) | — |
| 37 | $^a$35 (100%) | — |
| 38 | $^a$73.6 (100%) | — |
| 42 | $^a$60 (83.3%) | — |
| 46 | $^a$60 (66.7%) | — |
| 63 | 49.3 | 0.25 |

TABLE 3-continued

Measurement results of Lithium-pilocarpine induced status epilepticus of compounds in the test (Rats)

| Compound (Example) No. | Therapeutic effect Prevention(rat, ip) | |
| --- | --- | --- |
| | ED50(mg/kg) | Peak Time(h) |
| 65 | 15.3 | 2 |
| 67 | 28.2 | 0.5 |

[a]Injection amount (mg/kg),
Protection % = the percentage of prevention activity compared to the vehicle only, respectively.

TABLE 4

Measurement results of Lithium-pilocarpine induced status epilepticus of compounds in the test (Rats)

| Compound (Example) No. | Intervention(rat, iv) ED50(mg/kg) |
| --- | --- |
| 1 | 22.6 |
| 2 | [a]46 (50%) |
| 3 | [a]46 (83.3%) |
| 4 | [a]46 (100%) |
| 5 | [a]46 (66.7%) |
| 6 | [a]46 (100%) |
| 8 | [a]46 (50%) |
| 9 | [a]46 (66.7%) |
| 15 | [a]46 (100%) |
| 16 | [a]46 (100%) |
| 18 | [a]46 (66.7%) |
| 23 | [a]46 (100%) |
| 25 | [a]46 (100%) |
| 30 | [a]46 (83.3%) |
| 31 | [a]46 (100%) |
| 32 | [a]46 (100%) |
| 36 | [a]46 (66.7%) |
| 37 | [a]46 (100%) |
| 38 | [a]46 (50%) |
| 40 | [a]46 (100%) |
| 42 | [a]46 (66.7%) |
| 43 | [a]46 (16.7%) |
| 44 | [a]46 (83.3%) |
| 45 | [a]46 (33.3%) |
| 46 | [a]46 (50%) |
| 63 | [a]46 (50%) |
| 65 | [a]46 (100%) |
| 67 | [a]46 (100%) |

[a]Injection amount (mg/kg),
Protection % = the percentage of prevention activity compared to the vehicle only, respectively.

Example 117

Potential Pharmacological Therapies for Benzodiazepine-Resistant Status Epilepticus The lithium-pilocarpine model is used to study the effects of test compounds on the electrographic properties of benzodiazepine-resistant SE. Adult rats are implanted for electroencephalogram (EEG) recordings, and then pretreated with lithium chloride (127 mg/kg, 24 h) and scopolamine bromide (1 mg/kg; 30 min) prior to the administration of pilocarpine (50 mg/kg). Either thirty or sixty minutes after the development of the first motor seizure, the animals receive diazepam (10 mg/kg). Ten minutes after diazepam, the experimental group is given the test compound and the control group given vehicle. Typically, 8 animals comprise a "Trial" where 2 animals are controls (i.e., vehicle only) and 6 animals receive the test compound, although this varies depending on the number animals that actually experience SE. In order to have an adequate number of replications, two (or even more) Trials are conducted. When needed, additional control animals are derived from other temporally adjacent Trials using the same protocol. The obtained results are shown in following FIG. 1 and Table 5.

FIG. 1 showed the measurement results of benzodiazepine-resistant electrographic status epilepsy model of 1-(2-chlorophenyl)-(S)-1-hydroxypropyl-(S)-2-carbamate (compound 1) in the test (Rats). A graph summarizing the percent change in EEG power over time. Only animals that underwent pilocarpine-induced status epilepticus and had an acceptable EEG signal were included in the analysis. In addition, the vehicle group includes historical controls derived from other temporally adjacent trials. The data are the mean (solid line) and 95% confidence intervals (shaded) of model predictions for each of the treatments normalized to the power at the time of the injection of test compound/vehicle. Differences between the groups were assessed using the non-parametric Mann-Whitney U-teat. The dashed lines represent the time points at which a significant difference was found between the two groups ($p<0.05$).

TABLE 5

Measurement results of benzodiazepine-resistant status epilepticus of 1-(2-chlorophenyl)-(S)-1-hydroxypropyl-(S)-2-carbamate (compound 1) in the test

| Assay | Benzodiazepine-resistant status epilepticus (ip) |
| --- | --- |
| ED50(mg/kg) | 96.86 |

Example 118

Lamotrigene-Resistant Amygdala Kindled Model

Two group (n=8~10 group) of rats (i.e., vehicle- and LTG-treated) are kindled according to the following protocol. A bipolar stimulating electrode is stereotactically implanted into the left amygdale (AP+5.7 mm, ML+4.5, dv+2.0 from intra-aural zero) of adult male Sprague-Dawley rats (250~300 g) under ketamine-xylazine anesthesia. Three anchor screws are attached to the skull and the electrode assembly anchored to the skull with dental acrylic cement. After the incision is closed with sutures, the animal receives a single dose of Bicillin (60,000 unit, i.m.) and is returned to animal's home cage in the animal quarters. Animals are kindled according to the procedure described by Postma et. al. (LTG treatment during amygdale-kindled seizure development fails to inhibit seizures and diminishes subsequent anticonvulsant efficacy. *Epilepsia* 41:1514-21, 2000). Briefly, after one week, animals are stimulated at an initial stimulation intensity of 100 μAmps. The stimulus intensity increases in 50 μAmp increments until an afterdischarge (AD) of 4 sec or greater is elicited.

The kindling stimulus necessary to evoke an AD is then administered daily until all animals in both treatment groups display consistent stage 4 or 5 seizures on the Racine scale (Racine RJ Modification of seizure activity by electrical stimulation. II. Motor seizure. *Electroencephalogr Clin Neurophysiol* 32:281-94, 1972). Prior to each kindling stimulation rats receive a single dose of either vehicle (0.5% methylcellulose) or LTG (5 mg/kg of LTG suspended in vehicle) by intraperitoneal (i.p.) administration. Previous studies have shown that this dose of LTG dose not modify the development of kindling (Postma et al. 2000; Srivastava, AKea Proceedings of the AES Annual Meeting, Boston, Mass., *Epilepsia* 44 Suppl 9:42, 2003) but does lead to a LTG-resistant state. One week after all animals are kindled, both groups will receive a challenge dose of LTG (15 mg/kg) to confirm LTG sensitivity (vehicle-treated control animals) and LTG resistance (LTG-treated experimental group). After a washout period of 3~4 days, both groups are challenged with a single dose (demonstrated to produce minimal behavioral impairment) of an investigational AED. Rats in both treatment groups are then challenged with the kindling stimulus at the predetermined time-to-peak effect of the investigational AED. The obtained results are shown in following Table 6.

TABLE 6

Measurement results of lamotrigene-resistant amygdala kindled rat of 1-(2-chlorophenyl)-(S)-1-hydroxypropyl-(S)-2-carbamate (compound 1) in the test

| Assay | lamotrigene-resistant amygdala kindled model(ip) |
|---|---|
| ED50(mg/kg) | 16.99 |
| Seizure Score | 2.0 ± 0.7(Control: 5.0 ± 0.0) |

Example 119

Minimal Clonic Seizure (6 Hz) Test

Some clinically useful AEDs are ineffective in the standard MES and scPTZ tests but still have anticonvulsant activities in vivo. In order to identify potential AEDs with this profile, compounds may be tested in the minimal clonic seizure (6 Hz or 'psychomotor') test (Barton et al., 2001). Like the maximal electroshock (EMS) test, the minimal clonic seizure (6 Hz) test is used to assess a compound's efficacy against electrically induced seizures but used a lower frequency (6 Hz) and longer duration of stimulation (3 s).

Test compound was pre-administrated to mice via i.p. injection. At varying times, individual mice (four per time point) are challenged with sufficient current delivered through corneal electrodes to elicit a psychomotor seizure in 97% of animals (32 mA or 44 mA for 3 s) (Toman et al., 1952). Untreated mice will display seizures characterized by a minimal clonic phase followed by stereotyped, automatistic behaviors described originally as being similar to the aura of human patients with partial seizures. Animals not displaying this behavior are considered protected. The test may be evaluated quantitatively by measuring the response at varying doses at a determined time of peak effect (TPE). The obtained results are shown in following Table 5(Reference; Barton M. E., Klein B. D., Wolf H. H. and White H. S. (2001) Pharmacological characterization of the 6 Hz psychomotor seizure model of partial epilepsy, Epilepsy Res. 47: 217-227./Toman J. E., Everett G. M. and Richards R. K. (1952), The search for new drugs against epilepsy. Tex. Rep. Biol. Med. 10: 96-104.)

when the current is increased to twice the CC97(i.e., 44 mA), most AEDs loose their efficacy, and only few AEDs, including levetiracetam (at high doses), valproate, and novel AEDs such as brivaracetam and retigabine, allow complete protection against the 6-Hz seizures. Based on these observations, it was suggested that the 6-Hz stimulation may provide a useful and rather inexpensive model of therapy-resistant limbic seizures (Critical review of current animal models of seizures and epilepsy used in the discovery and development of new antiepileptic drugs (2011), Seizure 20, 359-368, Wolfgang Loscher).

TABLE 7

Measurement results of 6 Hz-induced seizure of 1-(2-chlorophenyl)-(S)-1-hydroxypropyl-(S)-2-carbamate (Compound 1) in the test(Mice)

| Assay | 6Hz | | |
|---|---|---|---|
| | 32 mA | 44 mA | Peak Time(h) |
| ED50(mg/kg) | 14.6 | 13.66 | 0.25 |

Example 120

MES (Maximal Electroshock Seizure) Test

In the MES test (Ref., G. Villetti et al. Neuropharmacology 40(2001) 866-878), an electrical stimulus (mice; 50 mA, 60 Hz, 0.2 sec and rats; 150 mA 60 Hz, 0.2 sec in the test animal) supplied by 11A Shocker (IITC Life Science Company) was delivered through corneal electrodes. All mice assigned to any electroshock at peak time (0.25, 0.5, 1, 2, 4 hr) were treated with each test compound sample which was dissolved in 30% PEG400 or 20% Tween80 prepared by saline solvent applied to oral before the test. If the test animal stretching their hind limb in a straight line weren't observed in the MES test, the results indicate that the test sample had an anti-excitation activity. Three doses of the test sample were administered orally to over 18 mice (6 mice per dose) for evaluating the respective doses at which 50% of the animals are protected from seizure (ED50). The value of ED50 (median effective dose) is calculated by Litchfield and Wicoxon log-probit method which is a dose-response relationship. Then, the test results are shown in following Table 3. Experimental animal, male ICR mice and male SD rats, were purchased from OrientBio or Nara biotech, Korea, and housed 4-5 mice per a cage for 4-5 days. The range of mice body weight was used between 19 and 26 grams. The obtained results are shown in following Table 8.

Neurotoxicity

The measurement of neurotoxicity of the test compounds was conducted by the method of Dunham and Miya [Dunham, N. W. and Miya, T. S. 1957. A note on a simple apparatus for detecting neurological deficit in rats and mice. *J. Am. Pharm. Assoc.* (Baltimore) 46: 208-209]. In the method, motor abilities of the test animals can be determined by observing whether the test animals can walk without falling from a rotator, thereby determining the value of neurotoxicity of each compound. Term "TD50" means the respective dose of the test compound at which 50% of the test animal exhibit neurotoxicity. They were pre-trained on the rotarod (Rotarod; Columbus instrument, rota-max, USA) at 6 rpm for 5 min 24 hr prior to the test. The peak time was determined by administration test material's random dose for 0.5, 1, 2, 4 hour. To evaluate the minimal neurotoxicity of the compound, the mice were placed on the Rotarod (rod circle; 3Cm) at 6 rpm and the test animal fails to maintain walking once or more during 1 minute, it can be regarded that the test animal exhibits neurotoxicity. The ratio of TD50 to ED50(TD50/ED50) is called as a protective index, and useful as a parameter for comparison of pharmaceutical efficacy and neurotoxicity. The obtained results are shown in following Tables 8 and 9.

[Statistical Analysis]

The obtained results are shown as mean±sem. The difference between the groups was statistically analyzed by ANOVA, and then, further examined by Dunnett's test or Bonferroni test. If p is less than 0.05, it was determined that the difference between the groups had statistical significance.

TABLE 8

Measurement results of anti-epilepsy activity of compounds in the test animals (Mice)

| Compound No. | MES test(po) | |
|---|---|---|
| | ED50(mg/kg) | Peak Time(h) |
| 1 | 13.0 | 2 |
| 2 | 51.0 | 0.25 |
| 3 | 31.4 | 2 |
| 4 | 82.4 | 0.5 |
| 5 | 84.1 | 0.5 |
| 6 | 22.2 | 1 |
| 8 | 100 $^a$(100%) | — |
| 9 | 67.1 | 0.5 |
| 12 | 100 $^a$(75%) | — |
| 13 | 200 $^a$(75%) | — |
| 14 | 200 $^a$(100%) | — |
| 15 | 100 $^a$(75%) | — |
| 16 | 200 $^a$(25%) | — |
| 18 | 200 $^a$(100%) | — |
| 23 | 200 $^a$(25%) | — |
| 25 | 200 $^a$(25%) | — |
| 29 | 200 $^a$(75%) | — |
| 30 | 200 $^a$(25%) | — |
| 31 | 200 $^a$(25%) | — |
| 32 | 200 $^a$(100%) | — |
| 36 | 82.8 | — |
| 37 | 25.8 | 0.25 |
| 38 | 91.4 | 2 |
| 39 | 41.2 | 1 |
| 40 | 46.9 | — |
| 42 | 35.2 | 0.5 |
| 43 | 100 $^a$(25%) | — |
| 44 | 100 $^a$(75%) | — |
| 46 | 35.2 | 1 |
| 63 | 50 $^a$(100%) | — |
| 65 | 50 $^a$(100%) | — |
| 67 | 100 $^a$(100%) | — |

$^a$ Injection amount(mg/kg),
Protection % = the percentage of activity compared to the vehicle only.

TABLE 9

Measurement results of neurotoxicity of compounds in the test animals (Mice)

| Compound No. | TD50 (mg/kg po) | PI(TD50/ED50 in MES) |
|---|---|---|
| 1 | 218.1 | 16.8 |
| 2 | 372.0 | 7.3 |
| 3 | 378.3 | 12.0 |
| 5 | 275.2 | 3.3 |
| 37 | 131.6 | 5.1 |

Example 121

PTZ (Pentylenetetrazol) Test

The obtained results are shown in following Tables 8 and 9. In this experiment, administered intraperitoneally (i.p.) or orally to test animals (Mouse; ICR, and Rats; SD); Experimental animal, male SD rats, were purchased from Orient-Bio or Nara biotech, Korea, and housed 4-5 mice per a cage for 4-5 days. The range of mice body weight was used between 19 and 26 grams and range of rats body weight was used between 100 and 130 grams. After Peak time (0.5, 1, 2 and 4 hr) from the administration, from the administration, PTZ (Pentylenetetrazol) was administered subcutaneously in the concentration capable of inducing 97% intermittent convulsions (mice & rats: 90~110 mg/kg·bw, 2 μl/g). If clonic seizure was not observed for at least 3 seconds in the PTZ administered animal, it can be considered that the test compound has nonconvulsive seizure activity. The median effective dose (ED50) is determined using 6 animals per a concentration (total three different concentrations), and calculated by Litchfield and Wicoxon log-probit method which is a dose-response relationship. The obtained results are shown in following Tables 10 and 11.

TABLE 10

Measurement results of anti-nonconvulsive seizure activity of compounds in the test animals (Mice)

| Compound No. | PTZ test (ip) in Mice | |
|---|---|---|
| | ED50(mg/kg) | Peak Time (h) |
| 1 | 15.8 | 2 |
| 2 | 38.8 | 0.5 |
| 3 | 15.3 | 0.5 |
| 4 | 26.7 | 0.5 |
| 5 | 15.0 | 0.5 |
| 6 | 17.9 | 0.5 |
| 8 | $^a$20.4 (50%) | — |
| 9 | $^a$20.4 (33.3%) | — |
| 12 | $^a$20.4 (33.3%) | — |
| 13 | $^a$20.4 (50%) | — |
| 14 | $^a$20.4 (16.7%) | — |
| 23 | $^a$20.4 (50%) | — |
| 25 | $^a$20.4 (66.7%) | — |
| 29 | $^a$20.4 (33.3%) | — |
| 30 | $^a$20.4 (33.3%) | — |
| 31 | $^a$20.4 (83.3%) | — |
| 32 | $^a$20.4 (16.7%) | — |
| 36 | $^a$20.4 (33.3%) | — |
| 37 | 25.7 | 0.25 |
| 38 | $^a$20.4 (50%) | — |
| 39 | 24.3 | 0.5 |
| 40 | $^a$20.4 (33.3%) | — |
| 42 | $^a$20.4 (50%) | — |
| 44 | $^a$20.4 (33.3%) | — |
| 45 | $^a$20.4 (16.7%) | — |
| 46 | $^a$20.4 (50%) | — |
| 63 | $^a$20.4 (50%) | — |
| 65 | $^a$20.4 (100%) | — |
| 67 | 23.1 | 0.5 |

$^a$Injection amount (mg/kg),
Protection % (Mice)
* Peak Time (h)

TABLE 11

Measurement results of anti-nonconvulsive seizure activity of compounds in the test animals (Rats)

| Compound No. | PTZ test (ip) in Rats ED50 (mg/kg) |
|---|---|
| 2 | 51.9(*1) |
| 3 | 18.9(*0.5) |
| 4 | $^b$30 (50%) |
| 6 | $^b$30 (50%) |
| 15 | $^b$25 (33.3%) |
| 16 | $^b$30 (33.3%) |
| 18 | $^b$30 (16.7%) |
| 37 | $^b$30 (50%) |
| 43 | $^b$25 (33.3%) |

TABLE 11-continued

Measurement results of anti-nonconvulsive seizure activity of compounds in the test animals (Rats)

| Compound No. | PTZ test (ip) in Rats ED50 (mg/kg) |
|---|---|
| 45 | [b]50 (16.7%) |
| 67 | [b]30 (33.3%) |

[b]Injection amount (mg/kg), Protection % (Rats)
*Peak Time (h)

What is claimed is:

1. A method of treating intractable epilepsy or an epilepsy-related syndrome in a subject, comprising administering to the subject a therapeutically effective amount of a compound of formula 1 or a pharmaceutically acceptable salt thereof, to a subject in need of treatment:

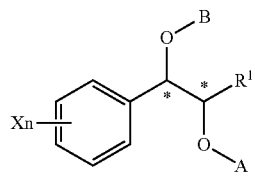

(chemical formula 1),
wherein,
X is a halogen,
n is an integer from 1 to 5,
R1 is a linear or branched alkyl group of C1-C4,
A is hydrogen or a carbamoyl group represented by

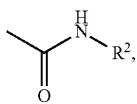

B is hydrogen or a carbamoyl group represented by

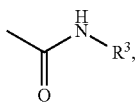

A and B are not carbamoyl derivatives at same time, and
R2 and R3 are selected from the group consisting of hydrogen, a linear or branched alkyl group of C1-C4, a cycloalkyl group of C3-C8, and benzyl group.

2. The method according to claim 1, wherein the phenyl carbamate compound is in the form of racemate, enantiomer, diastereomer, a mixture of enantiomer, or a mixture of diastereomer.

3. The method according to claim 2, wherein X is chlorine, fluorine, iodine, or bromine; n is 1 or 2; and R2 and R3 are the same as or different from each other, and independently selected from the group consisting of hydrogen, methyl, propyl, isopropyl, cyclopropyl, cyclohexyl, bicycloheptane, or benzyl.

4. The method according to claim 1, wherein the compound is:
1-(2-chlorophenyl)-1-hydroxypropyl-2-carbamate,
1-(2-chlorophenyl)-1-hydroxy-3-methyl-butyl-2-carbamate,
1-(2-chlorophenyl)-1-hydroxyhexyl-2-carbamate,
1-(2-chlorophenyl)-1-hydroxypropyl-2-N-methylcarbamate,
1-(2-chlorophenyl)-1-hydroxypropyl-2-N-propylcarbamate,
1-(2-chlorophenyl)-1-hydroxypropyl-2-N-isopropylcarbamate,
1-(2-chlorophenyl)-1-hydroxypropyl-2-N-cyclopropylcarbamate,
1-(2-chlorophenyl)-1-hydroxypropyl-2-N-cyclohexylcarbamate,
1-(2-chlorophenyl)-1-hydroxypropyl-2-N-benzylcarbamate,
1-(2-chlorophenyl)-1-hydroxypropyl-2-N-bicyclo[2,2,1]heptanecarbamate,
1-(2,4-dichlorophenyl)-1-hydroxypropyl-2-carbamate,
1-(2,6-dichlorophenyl)-1-hydroxypropyl-2-carbamate,
1- 2,4-dichlorophenyl)-1-hydroxybutyl-2-carbamate,
1-(2,4-dichlorophenyl)-1-hydroxy-3-methyl-butyl-2-carbamate,
1-(2,6-dichlorophenyl)-1-hydroxy-3-methyl-butyl-2-carbamate,
1-(2,4-dichlorophenyl)-1-hydroxyhexyl-2-carbamate,
1-(2,6-dichlorophenyl)-1-hydroxyhexyl-2-carbamate,
1-(2-chlorophenyl)-2-hydroxypropyl-1-carbamate,
1-(2-chlorophenyl)-2-hydroxypropyl-1-N-methylcarbamate,
1-(2-chlorophenyl)-2-hydroxypropyl-1-N-propylcarbamate,
1-(2-chlorophenyl)-2-hydroxypropyl-1-N-isopropylcarbamate,
1-(2-chlorophenyl)-2-hydroxypropyl-1-N-cyclopropylcarbamate,
1-(2-chlorophenyl)-2-hydroxypropyl-1-N-cyclohexylcarbamate,
1-(2-chlorophenyl)-2-hydroxypropyl-1-N-benzylcarbamate,
1-(2,4-dichlorophenyl)-2-hydroxypropyl-1-carbamate,
1-(2,6-dichlorophenyl)-2-hydroxypropyl-1-carbamate,
1-(2,4-dichlorophenyl)-2-hydroxybutyl-1-carbamate,
1-(2,6-dichlorophenyl)-2-hydroxybutyl-1-carbamate,
1-(2,4-dichlorophenyl)-2-hydroxy-3-methyl-butyl-1-carbamate,
1-(2,6-dichlorophenyl)-2-hydroxy-3-methyl-butyl-1-carbamate,
1-(2,4-dichlorophenyl)-2-hydroxyhexyl-1-carbamate,
1-(2,6-dichlorophenyl)-2-hydroxyhexyl-1-carbamate,
1-(2-fluorophenyl)-1-hydroxypropyl-2-carbamate,
1-(2-iodophenyl)-1-hydroxypropyl-2-carbamate,
1-(2-iodophenyl)-1-hydroxybutyl-2-carbamate,
1-(2,3-dichlorophenyl)-1-hydroxypropyl-2-carbamate, or
1-(2,3-dichlorophenyl)-2-hydroxypropyl-1-carbamate, or
a pharmaceutically acceptable salt thereof.

5. The method according to claim 1, wherein the compound is:
1-(2-chlorophenyl)-(S)-1-hydroxypropyl-(S)-2-carbamate,
1-(2-chlorophenyl)-(R)-1-hydroxypropyl-(R)-2-carbamate, racemate of 1-(2-chlorophenyl)-(S)-1-hydroxypropyl-(S)-2-carbamate and 1-(2chlorophenyl)-(R)-1-hydroxypropyl-(R)-2-carbamate, 1-(2-chlorophenyl)-(R)-1-hydroxypropyl-(S)-2-carbamate,
1-(2-chlorophenyl)-(S)-1-hydroxypropyl-(R)-2-carbamate,
1-(2-chlorophenyl)-(S)-1-hydroxybutyl-(S)-2-carbamate, racemate of 1-(2-chlorophenyl)-(S)-1-hydroxybutyl-(S)-2-carbamate and 1-(2chlorophenyl)-(R)-1-hydroxybutyl-(R)-2-carbamate,
1- (2-chlorophenyl)-(S)-1-hydroxy-3-methyl-butyl-(S)-2-carbamate, racemate of 1- (2-chlorophenyl)-(S)-1-hydroxy-3-methyl-butyl-(S)-2-carbamate and 1- (2chlorophenyl)-(R)-1-hydroxy-3-methyl-butyl-(R)-2-carbamate,
1-(2-chlorophenyl)-(S)-1-hydroxypropyl-(S)-2-N-methylcarbamate,
1-(2-chlorophenyl)-(S)-1-hydroxypropyl-(S)-2-N-propylcarbamate,
1-(2-chlorophenyl)-(S)-1-hydroxypropyl-(R)-2-N-isopropylcarbamate,
1-(2-chlorophenyl)-(S)-1-hydroxypropyl-(R)-2-N-cyclopropylcarbamate,
1-(2-chlorophenyl)-(S)-1-hydroxypropyl-(R)-2-N-cyclohexyl carbamate,
1-(2-chlorophenyl)-(R)-1-hydroxypropyl-(R)-2-N-methylcarbamate,
1-(2-chlorophenyl)-(R)-1-hydroxypropyl-(R)-2-N-propylcarbamate,
1-(2-chlorophenyl)-(R)-1-hydroxypropyl-(R)-2-N-isopropylcarbamate,
1-(2-chlorophenyl)-(R)-1-hydroxypropyl-(R)-2-N-cyclopropylcarbamate,
1-(2-chlorophenyl)-(R)-1-hydroxypropyl-(R)-2-N-cyclohexyl carbamate, racemate of 1- (2-chlorophenyl)-(S)-1-hydroxypropyl-(S)-2-N-methylcarbamate and 1-(2chlorophenyl)-(R)-1-hydroxypropyl-(R)-2-N-methylcarbamate racemate of 1- (2-chlorophenyl)-(S)-1-hydroxypropyl-(S)-2-N-propylcarbamate and 1-(2chlorophenyl)-(R)-1-hydroxypropyl-(R)-2-N-propylcarbamate, racemate of 1- (2-chlorophenyl)-(S)-1-hydroxypropyl-(S)-2-N-isopropylcarbamate and 1-(2-chlorophenyl) -(R)-1-hydroxypropyl-(R)-2-N-isopropylcarbamate, racemate of 1- (2-chlorophenyl)-(S)-1-hydroxypropyl-(S)-2-N-cyclopropylcarbamate and 1- (2-chlorophenyl)-(R)-1-hydroxypropyl-(R)-2-N-cyclopropylcarbamate, racemate of 1- (2-chlorophenyl)-(S)-1-hydroxypropyl-(S)-2-N-cyclohexylcarbamate and 1-(2-chlorophenyl) -(R)-1-hydroxypropyl-(R)-2-N-cyclohexylcarbamate,
1-(2-fluorophenyl)-(S)-1-hydroxypropyl-(S)-2-carbamate,
1-(2-fluorophenyl)-(R)-1-hydroxypropyl-(R)-2-carbamate,
1-(2-iodophenyl)-(S)-1-hydroxypropyl-(S)-2-carbamate,
1-(2-iodophenyl)-(R)-1-hydroxypropyl-(R)-2-carbamate, or
1-(2-iodophenyl)-(S)-1-hydroxybutyl-(S)-2-carbamate,
or a pharmaceutically acceptable salt thereof.

6. The method according to claim 1, wherein the intractable epilepsy is localization-related epilepsy, generalized epilepsy or syndromes thereof.

7. The method according to claim 6, wherein the localization-related epilepsy is cortical epilepsy or temporal lobe epilepsy.

8. The method according to claim 7, wherein the cortical epilepsy is frontal lobe epilepsy, parietal lobe epilepsy, or occipital lobe epilepsy.

9. The method according to claim 1, wherein the epilepsy-related syndrome is an epileptic seizure.

10. The method according to claim 9, wherein the epileptic seizure is an intractable localization-related epilepsy, an intractable secondary generalized seizure, an intractable complex partial seizure or an intractable status epilepticus.

* * * * *